(12) United States Patent
Luo et al.

(10) Patent No.: US 7,355,058 B2
(45) Date of Patent: *Apr. 8, 2008

(54) HALOALUMINOXANE COMPOSITIONS, THEIR PREPARATION, AND THEIR USE IN CATALYSIS

(75) Inventors: Lubin Luo, Baton Rouge, LA (US); Samuel A. Sangokoya, Baton Rouge, LA (US); Steven P. Diefenbach, Baton Rouge, LA (US); Jamie R. Strickler, Baton Rouge, LA (US); Christopher G. Bauch, Prairieville, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/509,938

(22) Filed: Aug. 25, 2006

(65) Prior Publication Data

US 2006/0287448 A1    Dec. 21, 2006

Related U.S. Application Data

(63) Continuation-in-part of application No. 10/751,144, filed on Dec. 31, 2003, now Pat. No. 7,193,100.

(51) Int. Cl.
   *C07F 5/06*     (2006.01)
   *C08F 4/602*    (2006.01)

(52) U.S. Cl. .................. 556/179; 556/180; 526/165

(58) Field of Classification Search .......... 556/179, 556/180; 526/165, 160
   See application file for complete search history.

(56) References Cited

U.S. PATENT DOCUMENTS

| 5,120,696 | A  | 6/1992  | Tsutsui et al. |
| 5,235,081 | A  | 8/1993  | Sangokoya |
| 5,329,032 | A  | 7/1994  | Tran et al. |
| 5,416,229 | A  | 5/1995  | Tran et al. |
| 5,556,821 | A  | 9/1996  | Aida et al. |
| 5,731,253 | A  | 3/1998  | Sangokoya |
| 5,831,109 | A  | 11/1998 | Smith et al. |
| 5,936,060 | A  | 8/1999  | Schmiegel |
| 6,046,347 | A  | 4/2000  | Jones et al. |
| 6,060,418 | A  | 5/2000  | Sangokoya |
| 6,063,726 | A  | 5/2000  | Kioka et al. |
| 6,153,550 | A  | 11/2000 | Kissin |
| 6,153,551 | A  | 11/2000 | Kissin et al. |
| 6,194,340 | B1 | 2/2001  | Sangokoya |
| 6,211,111 | B1 | 4/2001  | Chen et al. |
| 6,306,986 | B1 | 10/2001 | Teasley |
| 6,437,205 | B1 | 8/2002  | Miller et al. |

FOREIGN PATENT DOCUMENTS

| JP | 49293/1992      | 2/1992  |
| SU | 464602          | 9/1975  |
| WO | WO-03/082466 A1 | 10/2003 |
| WO | WO-03/082879 A1 | 10/2003 |

OTHER PUBLICATIONS

Sato et al., "Studies on Nickel-Containing Ziegler-Type Catalysts. I. New Catalysts for High-*cis*-1,4-polybutadiene", Bull. Chem. Soc. Jpn., 1992, pp. 1299-1306, vol. 65.

Siergiejczyk et al., "Reactions of Methylaluminium Halides With Lead Oxide", Polimery, 1986, p. 397-398.

*Primary Examiner*—Caixia Lu
(74) *Attorney, Agent, or Firm*—Frank C. Eymard

(57) ABSTRACT

Novel haloaluminoxane compositions have been formed. The halogen is fluorine, chlorine, and/or bromine, and the amount of halogen atoms present in said composition is in the range of about 0.5 mole % to about 15 mole % relative to aluminum atoms. Processes for producing haloaluminoxane compositions are also provided.

26 Claims, 1 Drawing Sheet

HALOALUMINOXANE COMPOSITIONS, THEIR PREPARATION, AND THEIR USE IN CATALYSIS

REFERENCE TO RELATED APPLICATION

This application is a Continuation-in-Part of commonly-owned U.S. application Ser. No. 10/751,144, filed Dec. 31, 2003, now U.S. Pat. No. 7,193,100, issued on Mar. 20, 2007.

The work leading to the invention described in this patent application was performed pursuant to a contract with an agency of the United States Government. The contract is Cooperative Agreement No. 70NANB0H3049 between Albemarle Corporation and the National Institute of Standards and Technology of the United States Department of Commerce (Advanced Technology Program).

TECHNICAL FIELD

This invention relates to new fluoroaluminoxane compositions, new chloroaluminoxane compositions, and new bromoaluminoxane compositions that are of particular utility in the formation of new catalyst systems, to methods for the preparation of these haloaluminoxane compositions and catalyst systems, to the use of such catalyst systems in the polymerization (homopolymerization and copolymerization) of olefins, dienes, or the like.

BACKGROUND

Partially hydrolyzed aluminum alkyl compounds known as aluminoxanes (a.k.a. alumoxanes) are effective in activating metallocenes for polymerization of olefins. Methylaluminoxane (a.k.a. methylalumoxane) has become the aluminum co-catalyst of choice in the industry. It is available commercially in the form of 10 to 30 wt % solutions in an aromatic solvent, typically toluene.

Modifications to methylaluminoxane have been reported. For example, U.S. Pat. No. 5,329,032 discloses the use of organic groups having electron-rich heteroatoms, such as oxygen or nitrogen, in methylaluminoxane to increase the stability of methylaluminoxane. The organic groups attached to the heteroatom were believed to provide the observed increases in solubility of the methylaluminoxane.

Fluorine species have been reported in aluminoxanes; again, these fluorine species are part of an organic group, which organic group is attached to the aluminum site. See U.S. Pat. No. 6,153,550, where pentafluorophenyl moieties are attached to the aluminoxane, and see U.S. Pat. No. 6,211,111 B1 for additional fluoroaromatic moieties attached to aluminoxanes.

Chlorinated hydrocarbons, particularly dichlorobenzene, have been reported to minimize gel formation when mixed with aluminoxanes. No reaction of the chlorinated hydrocarbons with the aluminoxanes was contemplated or reported; see Japanese Laid-open Patent 49293 (1992).

Halogenated aluminoxanes have been reported in U.S. Pat. No. 6,306,986 B1 (referred to therein as alkylhaloaluminoxanes). These halogenated aluminoxanes are required to have a high degree of halogenation, and are not derived from a pre-made aluminoxane.

SUMMARY OF THE INVENTION

Pursuant to this invention, simple, rapid, and low cost process technology is provided for producing novel fluoroaluminoxane compositions, novel chloroaluminoxane compositions, and novel bromoaluminoxane compositions. Such compositions typically have considerable stability under inert, anhydrous conditions, while maintaining their solubility in hydrocarbon solvents, especially aromatic hydrocarbon solvents. In addition to these desirable features, the novel compositions of the invention also perform as well as, if not better than, nonhalogenated aluminoxanes when used as cocatalysts in the polymerization of olefins. In the haloaluminoxane compositions of the invention, one or more halogen atoms are believed to be bonded directly to the aluminoxane.

The fluoroaluminoxane compositions of this invention, the chloroaluminoxane compositions of this invention, and the bromoaluminoxane compositions of this invention show improved characteristics as compared to certain aluminoxanes. The fluoroaluminoxane compositions are more preferred because the fluoroaluminoxanes show a greater degree of enhancement than do the chloroaluminoxanes and bromoaluminoxanes, when compared to the properties of corresponding nonhalogenated aluminoxanes. However, it is to be understood that the degree of enhancement in the characteristics of the chloroaluminoxanes and bromoaluminoxanes of this invention is also desirable.

Unlike certain aluminoxanes which often tend to haze or form gels during storage especially when at elevated temperatures, the fluoroaluminoxane compositions of this invention, chloroaluminoxane compositions of this invention, and bromoaluminoxane compositions of this invention have significantly reduced tendencies toward gel formation when in solution in an aromatic solvent.

These new fluoroaluminoxane compositions, chloroaluminoxane compositions, and bromoaluminoxane compositions are useful as activators or cocatalysts with a wide variety of transition metal catalysts for forming olefin homopolymers or copolymers. Because the fluoroaluminoxanes, chloroaluminoxanes, and bromoaluminoxanes of this invention are used as cocatalysts, the fluoroaluminoxanes, chloroaluminoxanes, and bromoaluminoxanes are sometimes referred to as cocatalysts in this document. Hereinafter, the fluoroaluminoxanes, chloroaluminoxanes, and bromoaluminoxanes are referred to collectively as haloaluminoxanes, with the understanding that the halogen may be fluorine, chlorine, and/or bromine. The invention also includes haloaluminoxane compositions that have mixtures of two or more halogens, in which there at least two different elements of halogen present in the haloaluminoxane composition.

Aluminoxanes are also called alumoxanes. Thus, the terms fluoroalumoxane and fluoroalumoxane are considered to be synonymous with the term fluoroaluminoxane. Analogously for the chloroaluminoxanes, the terms chloroalumoxane and chloro alumoxane are considered to be synonymous with the term chloroaluminoxane. Similarly for the bromoaluminoxanes, the terms bromoalumoxane and bromo alumoxane are considered to be synonymous with the term bromoaluminoxane.

This invention provides two novel types of species. One of these species is a haloaluminoxane complex, which, without wishing to be bound by theory, is believed to be an ionic complex comprised of an organic cation and an aluminum anion site of the aluminoxane, where one of the species coordinated to the aluminum anion site is a halogen atom. It is to be understood that the haloaluminoxane complexes are thought to exist only at the small number of aluminum anion sites of the aluminoxane, in particular those aluminum sites to which a halogen atom is coordinated. For simplicity, the entire species containing these complexes is referred to as a haloaluminoxane complex.

The other novel species of this invention is a partially halogenated aluminoxane, which is believed to be comprised of a neutral aluminoxane where halogen atoms are coordinated to some of the aluminum atoms of the aluminoxane. The term haloaluminoxane is used to refer to both haloaluminoxane complexes and to partially halogenated aluminoxanes.

In one of its embodiments this invention provides a haloaluminoxane composition wherein the halogen is fluorine, chlorine, and/or bromine. The amount of halogen atoms present in the haloaluminoxane composition is in the range of about 0.5 mole % to about 15 mole % relative to aluminum atoms. These haloaluminoxane compositions can be formed from components comprising (a) at least one aluminoxane and (b) at least one halogenation agent. The halogenation agent is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or (vi) mixtures of any two or more of (i)-(v).

An alternative method for forming the compositions of the invention is to have the halogenation agent present during the formation of the desired aluminoxane, i.e., during the hydrolysis of the aluminum hydrocarbyl(s) used to form the aluminoxane.

In still another embodiment, this invention provides process technology by which such haloaluminoxanes can be prepared. Such a process comprises mixing, in an inert, anhydrous environment, (a) at least one aluminoxane and (b) at least one halogenation agent which is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or (vi) mixtures of any two or more of (i)-(v), wherein the amount of halogen atoms is in the range of about 0.5 mole % to about 15 mole % relative to aluminum atoms, such that a haloaluminoxane composition is formed.

Another process for preparing haloaluminoxanes of the invention comprises contacting at least one aluminum hydrocarbyl with at least one halogenation agent during the hydrolysis of the aluminum hydrocarbyl. Again, the amount of halogen atoms is in the range of about 0.5 mole % to about 15 mole % relative to aluminum atoms, such that a haloaluminoxane composition is formed.

Another embodiment of this invention is a composition formed from interaction between components comprising (I) either a haloaluminoxane wherein the amount of halogen atoms is in the range of about 0.5 mole % to about 15 mole % relative to aluminum atoms, or (a) at least one aluminoxane and (b) at least one halogenation agent, wherein the amount of halogen atoms is in the range of about 0.5 mole % to about 15 mole % relative to aluminum atoms;

and (II) at least one catalyst compound or complex of a transition metal of Groups 3 to 11 including the lanthanide series and the actinide series. Other embodiments relate to polymerization processes in which a haloaluminoxane composition of this invention is employed as an activator or co-catalyst.

This invention also involves, inter alia, as especially preferred embodiments thereof, a catalyst composition comprised of a reaction product of a halide or pseudohalide (alkoxide, oxyhalide, etc.), or other Ziegler-Natta transition metal catalyst compound and a haloaluminoxane composition of this invention.

Methods for producing such catalyst compositions and methods of polymerizing or copolymerizing olefinic monomers using such catalyst compositions form still further embodiments of this invention.

These and other embodiments and features of this invention will be still further apparent from the ensuing description and appended claims.

FURTHER DETAILED DESCRIPTION OF THIS INVENTION

Figure 1:
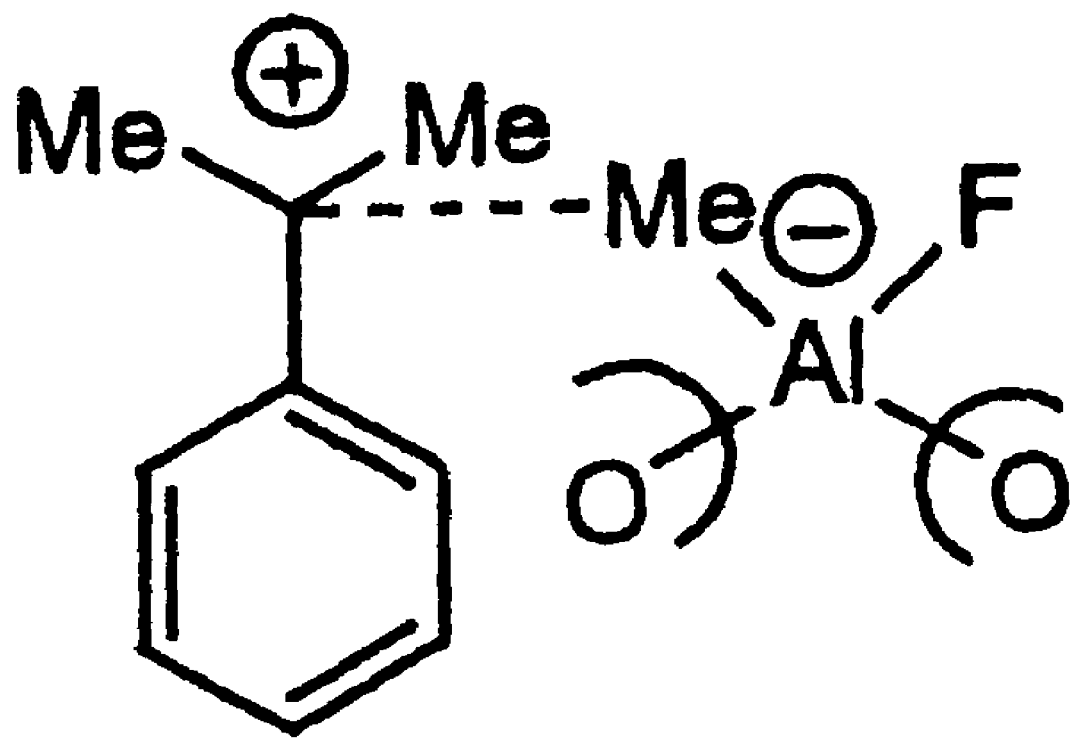
FIG. 1 is an enlarged schematic representation of a proposed structure of one of the preferred blue-colored fluoroaluminoxane complexes of this invention, which is postulated to be ionic.

To form the novel fluoroaluminoxane, chloroaluminoxane, and/or bromoaluminoxane compositions of this invention, an aluminoxane is reacted with at least one halogenation agent. Such halogenation agent is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_n SiX_{4-n}$, where n=1-3, X is, independently, fluorine, chlorine or bromine, and where R' is, independently, a hydrocarbyl group having from one to about twenty carbon atoms; or (iv) at least one tin compound of the formula $R'_n SnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_m AlX_{3-m}$, where m=1 or 2, where X is, independently, fluorine, chlorine or bromine, and where R" is, independently, a hydrocarbyl group having from one to about twenty carbon atoms; or (vi) mixtures of any two or more of (i)-(v).

The amount of halogen atoms is in the range of about 0.5 mole % to about 15 mole % relative to aluminum atoms. The reaction is conducted in an inert, anhydrous environment such as in an anhydrous liquid aromatic hydrocarbon solvent, such as one or more of benzene, toluene, xylene, mesitylene, ethylbenzene, diethylbenzene, 1,2,4-triethylbenzene, 1,3,5-triethylbenzene, amylbenzene, tetrahydronaphthalene, and the like.

As mentioned above, the compositions of the invention may also be formed by having the halogenation agent present during the hydrolysis of the aluminum hydrocarbyl(s) used to form the aluminoxane.

Increased stability is tested on a sample as a 30 wt % solution in toluene. The sample is stored indoors for 18 days at about 25° C., followed by outdoor storage at about 20-50° C. for 12 days. If gel formation has increased by five-fold or less, based on the weight percent gel found on the 30th day (in comparison to the amount of gel present initially), the haloaluminoxane is generally considered to be of increased stability.

It is preferred that the haloaluminoxane components as well as the resultant haloaluminoxane compositions be handled in an inert, moisture-free, oxygen free environment such as argon, nitrogen or helium because of the sensitivity of such components and compositions to moisture and oxygen.

Compounds of the Invention

This invention makes possible the preparation of certain fluoroaluminoxane complexes, which appear to be fluoroaluminoxane ion pairs, which complexes are believed to be intermediates in the synthesis of partially fluorinated aluminoxanes. Similarly, this invention also makes possible the preparation of certain chloroaluminoxane complexes, which appear to be chloroaluminoxane ion pairs, which complexes are intermediates in the synthesis of partially chlorinated aluminoxanes. Additionally, this invention makes possible the preparation of bromoaluminoxane complexes, which appear to be bromoaluminoxane ion pairs, which complexes are intermediates in the synthesis of partially brominated aluminoxanes.

Fluoroaluminoxane complexes which are believed to be ionic have been observed. At least some of these fluoroaluminoxane complexes are stable, at least in the absence of light and heat. It is possible that a few of these fluoroaluminoxane complexes can be isolated as solids. Chloroaluminoxane complexes which are believed to be ionic have been observed. A bromoaluminoxane complex which is believed to be ionic has been observed. Without being bound by theory, it is believed that the halogenation agent acts as the cationic counterpart to the anionic aluminum center in the haloaluminoxane complex. The available experimental evidence, especially proton and fluorine NMR, suggests that the fluoroaluminoxane complexes of this invention are composed of a fluoroaluminoxane monovalent anion site complexed or coordinated to a univalent cation formed from the halogenation agent. One of these fluoroaluminoxane complexes has been observed to be blue in toluene solution; a proposed but unconfirmed structure of the complex is depicted in FIG. 1. It is believed that fluorine is transferred to aluminum, forming a fluorine-aluminum bond, and an alkyl group is transferred to the fluorination agent. In the same manner, again without wishing to be bound by theory, the available experimental evidence for the chloroaluminoxane complexes also indicates a chloroaluminoxane monovalent anion site complexed or coordinated to a univalent cation formed from the chlorination agent. Again, it is believed that chlorine is transferred to aluminum, forming a chlorine-aluminum bond, and an alkyl group is transferred to the aromatic compound. Similarly for bromine, the experimental evidence suggests a bromoaluminoxane monovalent anion site complexed or coordinated to a univalent cation formed from the bromination agent.

Some of these haloaluminoxane complexes which are believed to be ionic have been observed to be thermal and light sensitive. Under ambient conditions without exclusion of light, the blue color of some of these complexes lasts from hours to days, depending on the halogen content. The blue color faded away faster at higher temperature, with exposure to light, or in contact with a polar solvent such as tetrahydrofuran (THF). Some of these haloaluminoxane complexes show decreased solubility in aromatic hydrocarbons, presumably due to the ionic character of the complex.

In experimental work conducted to date, haloaluminoxane complexes which are believed to be ionic and are formed from siloxanes, silanes, and tin compounds have not been isolated, nor have attempts been made to isolate such complexes. It is theorized that ionic haloaluminoxane complexes are formed as intermediates in the synthesis of partially halogenated aluminoxanes in the case of siloxanes, silanes, and tin compounds, but that the haloaluminoxane complexes proceed to the end product because the respective cations formed are unstable (relative to some of the carbon cations formed when a halohydrocarbon is the halogenation agent). However, it is contemplated that haloaluminoxane complexes formed from siloxanes, silanes, and tin compounds, if isolatable, probably require carefully controlled conditions, e.g., low temperatures (for example, circa −78° C.) and/or careful selection of a solvent that would stabilize a complex having ionic character. The existence of complexes which may be ionic is supported by the yellow color observed during the synthesis of the partially fluorinated aluminoxanes utilizing a siloxane, which yellow color is believed to be an ionic haloaluminoxane complex. It is not known whether hydrocarbyl aluminum halides form ionic haloaluminoxane complexes.

Mixing of an aluminoxane with at least one halogenation agent in an inert, anhydrous environment such as in an anhydrous liquid aromatic hydrocarbon solvent, preferably in the absence of heat, is generally sufficient to form a haloaluminoxane complex which is believed to be ionic.

These mixtures, containing complexes of the invention, are also deemed compositions of the invention.

Another type of haloaluminoxane of this invention is a partially halogenated aluminoxane. These compositions have been observed to be clear yellow, clear green, or colorless in toluene solution. This type of haloaluminoxane is believed to be an aluminoxane in which fluorine, chlorine, or bromine is bound to some of the aluminum atoms. Partially halogenated aluminoxanes can be formed by heating or aging a mixture containing a haloaluminoxane complex. For the halogenation agents for which a haloaluminoxane complex is not observed as an intermediate, the aluminoxane and halogenation agent are contacted to form the partially halogenated aluminoxane. For at least some siloxanes, silanes, and tin compounds, heating or aging is unnecessary. When the halogenation agent is a halohydrocarbon, silane, or tin compound, the major by-product of the formation of a partially halogenated aluminoxane is normally an organic compound analogous to that of the halogenation agent, in which it appears that the sites of the halogenation agent formerly having halogen atoms now contain hydrocarbyl groups, presumably from the aluminoxane.

It appears that the by-products formed during preparation of the partially halogenated aluminoxane do not bind to the partially halogenated aluminoxane when halohydrocarbons, silanes, or tin compounds are used in the preparation of the partially halogenated aluminoxanes.

When siloxanes are used in the preparation of the partially halogenated aluminoxanes, the siloxane by-product appears to remain associated with the partially halogenated aluminoxane. An advantage to this is that the presence of this siloxane by-product increases the solubility of the partially halogenated aluminoxane. The siloxane by-product does not appear to adversely affect the properties of the partially halogenated aluminoxane.

When the halogenation agent is a hydrocarbyl aluminum halide, the "hydrocarbyl aluminum" portion of the molecule becomes bound to, and part of, the aluminoxane moiety. The aluminum from the hydrocarbyl aluminum halide that becomes part of the aluminoxane is indistinguishable from the aluminum already present as part of the aluminoxane, and is thus an inexpensive method for increasing the aluminum content of an aluminoxane while halogenating the aluminoxane.

As previously mentioned, the amount of halogen atoms in the haloaluminoxane is in the range of about 0.5 mole % to about 15 mole % relative to aluminum atoms. At a mole ratio of less than about 0.5%, the formed haloaluminoxanes have properties similar to aluminoxanes. Above a mole ratio of about 15 mole %, solid formation tendencies increase. Preferred mole ratios of halogen atoms to aluminum atoms are in the range of about 2 mole percent to about 10 mole percent halogen (relative to aluminum). More preferred is ratio of about 2 mole percent to about 6 mole percent halogen atoms to aluminum atoms. The optimum mole ratio may vary with the particular haloaluminoxane. Experimental results indicate that the reaction of the halogenation agent with the aluminoxane is stoichiometric, i.e., most or all of the labile halogen atoms appear to transfer to the aluminoxane.

Partially halogenated aluminoxanes of this invention include, but are not limited to, partially fluorinated methylaluminoxane, partially fluorinated ethylaluminoxane, partially fluorinated n-propylaluminoxane, partially fluorinated n-butylaluminoxane, partially fluorinated isobutylaluminoxane, partially fluorinated n-hexylaluminoxane, partially fluorinated n-octylaluminoxane, partially fluorinated phenylaluminoxane, partially chlorinated methylaluminoxane, partially chlorinated ethylaluminoxane, partially chlorinated n-propylaluminoxane, partially chlorinated n-butylaluminoxane, partially chlorinated isobutylaluminoxane, partially chlorinated n-hexylaluminoxane, partially chlorinated n-octylaluminoxane, partially chlorinated phenylaluminoxane, partially brominated methylaluminoxane, partially brominated ethylaluminoxane, partially brominated n-propylaluminoxane, partially brominated n-butylaluminoxane, partially brominated isobutylaluminoxane, partially brominated n-hexylaluminoxane, partially brominated n-octylaluminoxane, and partially brominated phenylaluminoxane. Also included as partially halogenated aluminoxanes are those that have two or more different elements of halogen (e.g., fluorine and chlorine; fluorine and bromine; chlorine and bromine; fluorine, chlorine, and bromine).

Aluminoxane compositions are generally obtained by hydrolyzing aluminum compounds such as alkyl aluminum compounds with water e.g., by direct water addition, contact with a water-wet material such as a solvent containing water or a solid substrate such as a porous catalyst support wet with or soaked in water, or via salt hydrate addition. The resulting products, depending on the amount of added water, are dimeric or complex mixtures of oligomeric aluminoxanes.

Non-limiting examples of aluminoxanes that can be used to make the haloaluminoxanes of this invention include methylaluminoxane, ethylaluminoxane, n-propylaluminoxane, n-butylaluminoxane, isobutylaluminoxane, n-hexylaluminoxane, n-octylaluminoxane, decylaluminoxane, dodecylaluminoxane, tetradecylaluminoxane, hexadecylaluminoxane, octadecylaluminoxane, phenylaluminoxane, tolylaluminoxane, and the like. Mixtures of aluminoxanes may also be used.

Preferred aluminoxanes are those in which the hydrocarbyl groups are saturated, particularly those aluminoxanes in which the hydrocarbyl groups have from one to about twenty carbon atoms. More preferred are aluminoxanes in which the saturated hydrocarbyl groups have from one to about six carbon atoms. Even more preferred are methylaluminoxane, ethylaluminoxane, n-butylaluminoxane, and iso-butylaluminoxane. Highly preferred are methylaluminoxane and ethylaluminoxane. The most highly preferred aluminoxane is methylaluminoxane.

The methylaluminoxane may contain up to about 15 mole percent (based on aluminum) of moieties formed from amines, alcohols, ethers, esters, phosphoric and carboxylic acids, thiols, alkyl disiloxanes, and the like to improve their activity, solubility, and/or stability. A preferred type of moiety is a bulky phenol. Suitable bulky phenols include 2,6-dimethyl-4-(1,1-dimethylpropyl)phenol, 2,6-diisobutyl-4-methylphenol, 2,6-diisopropylphenol, 2,4,6-triisopropylphenol, 2,6-diisobutylphenol, 2,4,6-triisobutylphenol, 2,6-di-tert-butylphenol, 2,4,6-tri-tert-butylphenol, and the like. It is preferred that such phenols are reacted with the trialkylaluminum compound prior to the formation of the aluminoxane.

Concentrations of aluminoxanes are typically in the range of about 10 wt % aluminoxane to about 50 wt % aluminoxane. Preferably, the concentration of the aluminoxane solution is in the range of about 10 wt % to about 30 wt %. Usually, the aluminoxane is in a hydrocarbon solvent, preferably an aromatic hydrocarbon solvent. Most preferably, the aluminoxane is in toluene.

The halogenation agents that can be used in forming the haloaluminoxanes of the invention contain labile halogen atoms, i.e., halogen atoms that can react with aluminum sites in the aluminoxane. Non-labile halogen atoms may also be present in the halogenation agent. For example, halogen atoms directly bound to aromatic rings have been observed to be non-labile, i.e., such halogen atoms remain bound to the aromatic-ring when a halogenation agent containing such a moiety is brought into contact with an aluminoxane. Only those halogen atoms that are labile are considered in determining the mole percent of halogen atoms relative to aluminum atoms in the partially halogenated aluminoxane.

When R of the halohydrocarbon, R' of the silane or tin compound, or R'' of the hydrocarbyl aluminum halide is an aryl group, and the aryl group has a —OH, —SH, or —NH$_2$ group as a substituent on the aromatic ring, the —OH, —SH, or —NH$_2$ group will react with the aluminoxane before the labile halogen atoms do, resulting in the binding of the halogenation agent to the aluminoxane, followed by the reaction of the labile halogen atoms with the aluminoxane. This may be advantageous when the presence of such species improves the solubility and/or stability of the product haloaluminoxane and/or the activity imparted to a polymerization by the use of such a haloaluminoxane as a cocatalyst. The need for labile halogen atoms in the halogenation agent excludes such moieties as pentafluorophenol, which does not have labile halogen atoms.

Haloaluminoxanes having two or more different types (elements) of halogen can be prepared. One way to obtain such haloaluminoxanes is to use a mixture of halogenation agents, where at least one halogenation agent has labile halogen atom(s) of one element, and at least one halogenation agent has labile halogen atom(s) of another element. Another method for preparing haloaluminoxanes having two or more different halogen elements is to use one or more halogenation agents in which there are halogen atoms of two or more different elements of halogen. Labile fluorine atoms normally react faster with the aluminoxane than do labile chlorine or bromine atoms.

One type of halogenation agent that can be used to form the haloaluminoxanes of this invention is a halohydrocarbon of the formula R$_n$CX$_{4-n}$, where n=1-3, X is, independently, fluorine, chlorine or bromine, and where R is, independently, a hydrogen atom or a hydrocarbyl group having from one to about twenty carbon atoms. R can be a straight chain, branched, cycloalkyl, aryl, or araalkyl group. When only one R is a hydrocarbyl group, the hydrocarbyl group is preferably an aryl group. Halohydrocarbons in which all R are hydrogen atoms are not preferred, because such halohydrocarbons tend to react slowly with the aluminoxane, and frequently the reaction does not go to completion, i.e., the yields are low.

A preferred type of halohydrocarbon is a tertiary halohydrocarbon; a more preferred type of halohydrocarbon is that in which at least one R is an aryl group. Less preferred are secondary and primary halohydrocarbons, because it is believed that they provide less stability to the intermediate in the formation of the partially halogenated aluminoxane, or to the postulated cationic species of the haloaluminoxane complexes.

A highly preferred type of halohydrocarbon is one in which at least one R is an aryl group, especially a phenyl group. When at least one R is an aryl group, tertiary halohydrocarbons are not especially preferred, i.e., a primary halohydrocarbon in which one R is an aryl group and the other R(s) are hydrogen atoms, or all of the other substituents are halogen atoms, are also highly preferred. In particular, this highly preferred group of halohydrocarbons can be represented by the formula:

ArG$_n$ where Ar is an aromatic hydrocarbon ring system, which typically contains up to about 25 carbon atoms, preferably up to about 12 carbon atoms, and most preferably 6 carbon atoms in the ring system (i.e., excluding X and excluding any substituents that may be present on the ring(s)); G is —CX$_3$, —CX$_2$R, or —CXR$_2$, in which X is, independently, a fluorine atom, chlorine atom, or bromine atom, and in which R is, independently, a hydrogen atom or C$_{1-4}$ alkyl group; and n is 1 to 5, preferably 1 to 3, more preferably 1 or 2, and most preferably 1. G is preferably a trihalomethyl group.

When there are substituents on the aromatic ring(s) other than hydrogen and the group(s) containing labile halogen atom(s), it is preferred that these other such substituents are electron-donating substituents. Halogenation agents containing aromatic groups having electron-withdrawing substituents on the ring, such as fluorine, were observed to have slower reaction rates than halogenation agents with aromatic groups having only hydrogen atoms as substituents. In turn, halogenation agents containing aromatic groups having electron-donating substituents were observed to have faster reaction rates than halogenaton agents in which there were only hydrogen atoms on the aromatic ring. Typical electron-donating substituents include hydrocarbyloxy groups and hydrocarbyl groups.

Suitable halohydrocarbons having an aryl group include α,α,α-trifluorotoluene, α,α-difluorotoluene, α-fluorotoluene, octafluorotoluene, 1,2-di(fluoromethyl)benzene, 1,3-di(fluoromethyl)benzene, 1,4-di(fluoromethyl)benzene, 1,2-bis(difluoromethyl)benzene, 1,3-bis(difluoromethyl)benzene, 1,4-bis(difluoromethyl)benzene, 1,3-bis(trifluoromethyl)benzene, 1,3,5-tris(trifluoromethyl)benzene, 4-methyl-1-(trifluoromethyl)benzene, 3-methyl-1-(trifluoromethyl)benzene, 1,3-bis(trifluoromethyl)-4-methylbenzene, 1,4-bis(trifluoromethyl)-2-methylbenzene, 1-ethyl-3,5-bis(trifluoromethyl)benzene, 1-isopropyl-4-(trifluoromethyl)benzene, 1-(fluoromethyl)-4-fluoro-2-(trifluoromethyl)benzene, 1-(fluoromethyl)-2,4-bis(trifluoromethyl)benzene, 1-(1-fluoroethyl)benzene, 1,2-difluoroethylbenzene, 3,3'-bis(trifluoromethyl)biphenyl, 4,4'-bis(trifluoromethyl)biphenyl, 2,2'-bis(fluoromethyl)biphenyl, 3-(difluoromethyl)biphenyl, 1-(trifluoromethyl)naphthalene, 2-(trifluoromethyl)naphthalene, 1-(difluoromethyl)naphthalene, 2-(difluoromethyl)naphthalene, 1-(fluoromethyl)naphthalene, 1,8-bis(fluoromethyl)naphthalene, 1-(fluoromethyl)-2-(methyl)naphthalene, 1-isobutyl-2-trifluoromethyl-naphthalene, 1-methyl-4-trifluoromethyl-naphthalene, 1-n-butyl-5-trifluoromethyl-naphthalene, 1-(trifluoromethyl)anthracene, 2-(difluoromethyl)anthracene, 9-(fluoromethyl)anthracene, 9,10-bis(trifluoromethyl)anthracene, 9-(trifluoromethyl)-phenanthrene, triphenylfluoromethane, difluorodiphenylmethane, α,α,α-trichlorotoluene, α,α-dichlorotoluene, α-chlorotoluene, 1,3-bis(trichloromethyl)-4-methylbenzene, 1,4-bis(trichloromethyl)-2-methylbenzene, 4-methyl-1-(trichloromethyl)benzene, 3-methyl-1-(trichloromethyl)benzene, octachlorotoluene, 1,2-di(chloromethyl)benzene, 1,3-di(chloromethyl)benzene, 1,4-di(chloromethyl)benzene, 1,3,5-tris(trichloromethyl)benzene, 1-ethyl-3,5-bis(trichloromethyl)benzene, 1-isopropyl-4-(trichloromethyl)benzene, 1-(chloromethyl)-4-chloro-2-(trichloromethyl)benzene, 1-(chloromethyl)-2,4-bis(trichloromethyl)benzene, 1-(1- chloroethyl)benzene, 1,2-dichloroethylbenzene, 3,3'-bis(trichloromethyl)biphenyl, 4,4'-bis(trichloromethyl)biphenyl, 2,2'-bis(chloromethyl)-biphenyl, 3-(dichloromethyl)biphenyl, 1-(trichloromethyl)naphthalene, 2-(trichloromethyl)naphthalene, 1-(dichloromethyl)naphthalene, 2-(dichloromethyl)-naphthalene, 1-(chloromethyl)naphthalene, 1,8-bis(chloromethyl)-naphthalene, 1-(chloromethyl)-2-(methyl)naphthalene, 1-isobutyl-2-trichloromethylnaphthalene, 1-methyl-4-trichloromethylnaphthalene, 1-n-butyl-5-trichloromethyl-naphthalene, 1-(trichloromethyl)-anthracene, 2-(dichloromethyl)anthracene, 9-(chloromethyl)anthracene, 9,10-bis(trichloromethyl)anthracene, 9-(trichloromethyl)phenanthrene, triphenylchloromethane, dichlorodiphenylmethane, α,α,α-tribromotoluene, α,α-dibromotoluene, α-bromotoluene, 1,2-di(bromomethyl)benzene, 1,3-di(bromomethyl)benzene, 1,4-di(bromomethyl)benzene, 1,3-bis(tribromomethyl)benzene, 1,3,5-tris(tribromomethyl)benzene, 4-methyl-1-(tribromomethyl)benzene, 3-methyl-1-(tribromomethyl)benzene, 1,3-bis(tribromomethyl)-4-methylbenzene, 1,4-bis(tribromomethyl)-2-methylbenzene, 1-ethyl-3,5-bis(tribromo-methyl)benzene, 1-isopropyl-4-(tribromomethyl)benzene, 1-(bromomethyl)-2-(tribromomethyl)benzene, 1-(bromomethyl)-2,4-bis(tribromomethyl)benzene, 1-(1-bromoethyl)-benzene, 1,2-dibromoethylbenzene, 3,3'-bis(tribromomethyl)biphenyl, 4,4'-bis(tribromomethyl)biphenyl, 2,2'-bis(bromomethyl)biphenyl, 3-(dibromomethyl)biphenyl, 1-(tribromomethyl)naphthalene, 2-(tribromomethyl)naphthalene, 1-(dibromomethyl)-naphthalene, 2-(dibromomethyl)-naphthalene, 1-(bromomethyl)naphthalene, 1,8-bis(bromomethyl)naphthalene, 1-(bromomethyl)-2-(methyl)naphthalene, 1-isobutyl-2-tribromomethyl-naphthalene, 1-methyl-4-tribromomethyl-naphthalene, 1-n-butyl-5-tribromomethyl-naphthalene, 1-(tribromomethyl)anthracene, 2-(dibromomethyl)anthracene, 9-(bromomethyl)anthracene, 9,10-bis(tribromomethyl)anthracene, 9-(tribromomethyl)phenanthrene, triphenylbromomethane, dibromodiphenylmethane, and the like. Mixtures of two or more of the foregoing halohydrocarbons may also be used.

Suitable halohydrocarbons which do not have an aryl group include tert-butyl fluoride (2-methyl-2-fluoropropane), 3-methyl-3-fluoropentane, 3-methyl-3-fluorohexane, 1-methyl-1-fluorocyclohexane, 1,3-difluoro-1,3,5-methylcyclooctane, 2-methyl-2-fluorohexane, 1,2-difluoro-1-methylcyclooctane, 2-methyl-2-chloropropane, tert-butyl chloride, 3-methyl-3-chloropentane, 3-chlorohexane, 3-methyl-3-chlorohexane, 1-methyl-1-chlorocyclohexane, 1,3-dichloro-1,3,5-methylcyclooctane, 2-methyl-2-chloroheptane, 1,2-dichloro-1-methylcyclooctane, 2-methyl-2-bromopropane, tert-butyl bromide, 3-methyl-3-bromopentane, 2-bromohexane, 3-bromohexane, 3-methyl-3-bromohexane, 1-methyl-1-bromocyclohexane, 1,3-dibromo-1,3,5-methylcyclooctane, 2-methyl-2-bromoheptane, 1,2-dibromo-1-methylcyclooctane, and the like. Mixtures of two or of the foregoing halohydrocarbons may also be used.

Suitable halohydrocarbons which have at least two different elements of halogen that may be used include, but are not limited to, 1-chloro-3-fluoro-1,3,5-methylcyclooctane, 2-bromo-1-fluoro-1-methylcyclooctane, 2-chloro-1-fluoro-1-methylcyclooctane, 1-(trichloromethyl)-4-(trifluoromethyl)benzene, 1-(dichloromethyl)-3-(dibromomethyl)-benzene, 1-(bromomethyl)-2-(fluoromethyl)benzene, 1-(chloromethyl)-4-(trifluoromethyl)-benzene, 1-(dichloromethyl)-3-(fluoromethyl)benzene, 1-(bromomethyl)-3,5-bis(trifluoromethyl)benzene, 1-(chloromethyl)-3,5-bis(trifluoromethyl)benzene, 1-(tribromomethyl)-3-(trichloromethyl)-5-(trifluoromethyl)benzene, 1-ethyl-3-(trichloromethyl)-5-(trifluoromethyl)benzene, 1-(chloromethyl)-4-chloro-2-(tribromomethyl)-benzene, 1-(fluoromethyl)-2,4-bis(trichloromethyl)benzene, 1-(1-bromoethyl)-3-(1-fluoroethyl)-benzene, 1-(1,2-dichloroethyl)-4-(1-fluoroethyl)benzene, 1-trichloromethyl-4-trifluoromethyl-2,3,5,6-tetrachlorobenzene, 3-(trichloromethyl)-3'-(trifluoromethyl)biphenyl, 4-(dichloromethyl)-4'(difluoromethyl)-biphenyl, 2-(chloromethyl)-2'-(fluoromethyl)biphenyl, 1-(trichloromethyl)-2-(trifluoromethyl)naphthalene, 1-(difluoromethyl)-2-(dichloromethyl)-naphthalene, 1-(bromomethyl)-8-(fluoromethyl)naphthalene, 9-(trifluoromethyl)-10-(trichloromethyl)anthracene, and the like. Mixtures of two or more of the foregoing halohydrocarbons may also be used.

Preferred halohydrocarbons are tert-butyl fluoride, tert-butyl chloride, tert-butyl bromide, α,α,α-trifluorotoluene, 4-methyl-1-(trifluoromethyl)benzene, 3-methyl-1-(trifluoromethyl)benzene, triphenylfluoromethane, α,α,α-trichlorotoluene, 4-methyl-1-(trichloromethyl)benzene, 3-methyl-1-(trichloromethyl)benzene, triphenylchloromethane, α,α,α-tribromotoluene, 4-methyl-1-(tribromomethyl)benzene, 3-methyl-1-(tribromomethyl)-benzene, and triphenylbromomethane. More preferred are α,α,α-trifluorotoluene, 4-methyl-1-(trifluoromethyl)benzene, α,α,α-trichlorotoluene, triphenylchloromethane, α,α,α-tribromo-toluene, and triphenylbromomethane. The most preferred halohydrocarbons are α,α,α-trifluorotoluene, 4-methyl-1-(trifluoromethyl)benzene, triphenylchloromethane, and α,α,α-tribromotoluene.

Another type of halogenation agent that can be used to form the haloaluminoxanes of this invention is at least one siloxane having at least one labile halogen atom in the molecule, wherein each halogen atom is, independently, fluorine, chlorine, or bromine. These siloxanes have hydrocarbyl groups which preferably contain from about 1 to 30 carbon atoms and include linear and/or branched alkyl groups which contain from about 1 to 24 carbon atoms, cycloalkyl groups which contain from about 3 to 24 carbon atoms, and alkylaryl or aryl groups which contain from about 6 to 30 carbon atoms. At least one hydrocarbyl group of the siloxane contains at least one labile halogen atom. The siloxanes are chosen from disiloxanes and linear or cyclic polysiloxanes. The siloxanes contain the Si—O—Si bond and are substantially free of Si—OH bonds. The siloxanes can contain mixed hydrocarbyl groups. The polysiloxanes have a linear, or branched, or cyclic backbone of alternating silicon and oxygen atoms. If the polysiloxane is acyclic, it can be represented by the empirical formula, $Si_nO_{n-1}$, wherein n is at least 3 (preferably in the range of 3 to 6, and most preferably in the range of 3 to 4), and wherein the oxygen atoms are always individually disposed between and connected to two silicon atoms as a —Si—O—Si— moiety. The cyclic polysiloxanes can be represented by the empirical formula $Si_nO_n$ where n is as defined above, and wherein, as in the case of the acyclic polysiloxanes, the oxygen atoms are always individually disposed between and connected to two silicon atoms as a —Si—O—Si— moiety. Whether cyclic or acyclic, the backbone of a polysiloxane containing 4 or more silicon atoms can be branched on one or more of the silicon atoms of the backbone. In such case, the silicon atom that carries the branch is bonded to three or four separate oxygen atoms, and each such oxygen atom is in turn bonded to an additional separate silicon atom.

Non-limiting examples of siloxanes include (trifluoromethyl)pentamethyldisiloxane, tris(fluoromethyl)trimethyldisiloxane, (2,2-difluoroethyl)pentaethyldisiloxane, bis(1,2-difluoroethyl)triethyldisiloxane, bis(trifluoromethyl)tetramethyldisiloxane, (trifluoromethyl)trimethyldicyclohexyldisiloxane, tetramethylbis(2,2-difluorocyclohexyl)-disiloxane, tetramethylbutyl(4,4,4-trifluorobutyl)disiloxane, bis(p-trifluoromethylphenyl)-tetraphenyldisiloxane, diphenyltrimethyl(difluoromethyl)disiloxane, tetraphenylbis-(fluoromethyl)disiloxane, bis(difluoromethyl)tetramethylcyclotrisiloxane, tetra(fluoromethyl)tetramethyltrisiloxane, 3,3,3-trifluoropropylheptamethyltrisiloxane, bis(3,3,3-trifluoropropyl)hexamethyltrisiloxane, 3,3,3-trifluoropropylheptamethylcyclo-trisiloxane, (trifluoromethyl)heptamethylcyclotetrasiloxane, bis(m-trifluoromethylphenyl)-hexaphenylcyclotetrasiloxane, tri [methyl(3,3,3-trifluoropropyl)cyclopolysiloxane], tetra[methyl(3,3,3-trifluoropropyl)cyclopolysiloxane], poly[methyl(3,3,3-trifluoropropyl)siloxane], poly[dimethylsiloxane-co-methyl(3,3,3-trifluoropropyl)siloxane], (trichloromethyl)pentamethyldisiloxane, tris(chloromethyl)trimethyldisiloxane, 2,2-(dichloroethyl)pentaethyldisiloxane, bis(1,2-dichloroethyl)triethyldisiloxane, bis(trichloromethyl)tetramethyldisiloxane, (trichloromethyl)trimethyldicyclohexyldisiloxane, tetramethylbis(2,2-dichlorocyclohexyl)disiloxane, tetramethylbutyl(4,4,4-trichlorobutyl)disiloxane, bis(p-trichloromethylphenyl)tetraphenyldisiloxane, diphenyltrimethyl(dichloromethyl)disiloxane, tetraphenylbis(chloromethyl)disiloxane, bis(dichloromethyl)tetramethylcyclotrisiloxane, tetra(chloromethyl)tetramethyltrisiloxane, 3,3,3-trichloropropylheptamethyltrisiloxane, bis(3,3,3-trichloropropyl)hexamethyltrisiloxane, 3,3,3-trichloropropylheptamethylcyclotrisiloxane, (trichloromethyl)heptamethylcyclotetra-siloxane, bis(m-trichloromethylphenyl)hexaphenylcyclotetrasiloxane, tri [methyl(3,3,3-trichloropropyl)cyclopolysiloxane], tetra[methyl(3,3,3-trichloropropyl)cyclopolysiloxane], poly[methyl(3,3,3-trichloropropyl)siloxane], poly[dimethylsiloxane-co-methyl(3,3,3-trichloropropyl)siloxane], (tribromomethyl)pentamethyldisiloxane, (2,2-dibromoethyl)pentaethyldisiloxane, tetramethylbis(2,2-dibromocyclohexyl)disiloxane, bis(p-tribromomethylphenyl)tetraphenyldisiloxane, bis(dibromomethyl)tetramethylcyclotrisiloxane, bis(3,3,3-tribromopropyl)hexamethyltrisiloxane, 3,3,3-tribromopropylheptamethyltrisiloxane, 3,3,3-tribromopropylheptamethylcyclotrisiloxane, tri[methyl(3,3,3-tribromopropyl)-cyclopolysiloxane], tetra[methyl(3,3,3-tribromopropyl)cyclopolysiloxane], poly[methyl(3,3,3-tribromopropyl)siloxane], and poly[dimethylsiloxane-co-methyl(3,3,3 -tribromoprophyl)siloxane], and the like. Mixtures of two or more of the foregoing siloxanes may also be used.

Suitable siloxanes having two or more different elements of halogen include, but are not limited to, (fluoromethyl)(chloromethyl)(bromomethyl)trimethyldisiloxane, (2,2-dichloroethyl)(2,2-difluoroethyl)tetraethyldisiloxane, (1,2-dichloroethyl)(1,2-difluoroethyl)triethyldisiloxane, (trichloromethyl)(tribromomethyl)tetramethyldisiloxane, tetramethyl(2,2-dichlorocyclohexyl)(2,2-difluorocyclohexyl)disiloxane, (p-tribromomethylphenyl)(p-trifluoromethylphenyl)tetraphenyldisiloxane, tetraphenyl(chloromethyl) (fluoromethyl)disiloxane, (dichloromethyl)difluoromethyl)tetra-ethylcyclotrisiloxane, bis(chloromethyl)bis(fluoromethyl)tetranethyltrisiloxane, (3,3,3-trichloropropyl)(3,3,3-trifluoropropyl)hexamethyltrisiloxane, (m-trichloromethylphenyl)(m-trifluoromethylphenyl)hexaphenylcyclotetrasiloxane, and the like. Mixtures of two or more of the foregoing siloxanes may also be used.

Preferred siloxanes are trisiloxanes and tricyclosiloxanes. Also preferred are siloxanes with at least one 3,3,3-trihalopropyl group. Preferred siloxanes include 3,3,3-trifluoropropylheptamethyltrisiloxane, 3,3,3-trifluoropropylheptamethylcyclotrisiloxane, tri[methyl(3,3,3-trifluoropropyl)cyclopolysiloxane], tetra[methyl(3,3,3-trifluoropropyl)cyclopolysiloxane], poly[methyl(3,3,3-trifluoropropyl)siloxane], poly[dimethylsiloxane-co-methyl(3,3,3-trifluoropropyl)siloxane]; 3,3,3-trichloropropylheptamethyltrisiloxane, 3,3,3-trichloropropylheptamethylcyclotrisiloxane, tri[methyl(3,3,3-trichloropropyl)cyclopolysiloxane], tetra[methyl(3,3,3-trichloropropyl)cyclopolysiloxane], poly[methyl(3,3,3-trichloropropyl)siloxane], poly[dimethylsiloxane-co-methyl(3,3,3-trichloropropyl)siloxane]; 3,3,3-tribromopropylheptamethyltrisiloxane, 3,3,3-tribromopropylheptamethylcyclotrisiloxane, tri[methyl(3,3,3-tribromopropyl)cyclopolysiloxane], tetra[methyl(3,3,3-tribromopropyl)cyclopolysiloxane], poly[methyl(3,3,3-tribromopropyl)siloxane], and poly[dimethylsiloxane-co-methyl(3,3,3-tribromopropyl)siloxane]. More preferred are 3,3,3-trifluoropropylheptamethyltrisiloxane, 3,3,3-trifluoropropylheptamethylcyclotrisiloxane, poly[methyl(3,3,3-trifluoropropyl)siloxane], 3,3,3-trichloropropylheptamethyltrisiloxane, 3,3,3-trichloropropylheptamethylcyclotrisiloxane, poly[methyl(3,3,3-trichloropropyl)siloxane], 3,3,3-tribromopropylheptamethyltrisiloxane, 3,3,3-tribromopropylheptamethylcyclotrisiloxane, and poly[methyl(3,3,3-tribromopropyl)siloxane]. The most preferred siloxanes are poly[methyl(3,3,3-trifluoropropyl)siloxane], poly[methyl(3,3,3-trichloropropyl)siloxane], and poly[methyl(3,3,3-tribromopropyl)siloxane].

Still another type of halogenation agent that may be used in forming the haloaluminoxanes of the invention is at least one silane of the formula $R'_n SiX_{4-n}$, where n=1-3, X is, independently, fluorine, chlorine or bromine, and where R' is, independently, a hydrocarbyl group having from one to about twenty carbon atoms. Each R' can be a straight chain, branched, cycloalkyl, aryl, or araalkyl group. R' is preferably an aryl group; when R' is an aryl group, it preferably has from six to about twenty carbon atoms; it is more preferred that the aryl group is a phenyl group. More preferably, R' is a straight chain or branched hydrocarbyl group, and when R' is a straight chain or branched hydrocarbyl group, it preferably has from one to about twelve carbon atoms; more preferably, R' has from one to about six carbon atoms; the most preferred straight chain or branched hydrocarbyl group is a methyl group.

Silanes that can be used as halogenation agents include, but are not limited to, trimethylfluorosilane, dimethyldifluorosilane, diethyldifluorosilane, diisopropyldifluorosilane, tert-butyltrifluorosilane, dicyclobutyldifluorosilane, tripentylfluorosilane, dicyclohexyldifluorosilane, triheptylfluorosilane, dicyclooctyldifluorosilane, triphenylfluorosilane, diphenyldifluorosilane, phenyltrifluorosilane, phenyldimethylfluorosilane, diphenylmethylfluorosilane, phenylmethyldifluorosilane, phenyldiisopropylfluorosilane, tritolylfluorosilane, ditolyldifluorosilane, trimethylchlorosilane, dimethyldichlorosilane, methyltrichlorosilane, triethylchlorosilane, diethyldichlorosilane, ethyltrichlorosilane, di-n- propyldichlorosilane, triisopropylchlorosilane, isobutyltrichlorosilane, dipentyldichlorosilane, cyclohexyltrichlorosilane, dicycloheptyldichlorosilane, dodecyltrichlorosilane, tert-butyldimethylchlorosilane, octylmethyldichlorosilane, dimethyloctadecylchlorosilane, chlorodimethyl-tert-hexylsilane, benzyltrichlorosilane, triphenylchlorosilane, diphenyldichlorosilane, phenyltrichlorosilane, phenyldimethylchlorosilane, diphenylmethylchlorosilane, phenylmethyldichlorosilane, phenyldiisopropylchlorosilane, tert-butyldiphenylchlorosilane, tritolylchlorosilane, ditolyldichlorosilane, trimethylbromosilane, dimethyldibromosilane, methyltribromosilane, triethylbromosilane, diisopropyldibromosilane, n-propyltribromosilane, tert-butyltribromosilane, dicyclopentyldibromosilane, trihexylbromosilane, cycloheptyltribromosilane, dioctyldibromosilane, triphenylbromosilane, diphenyldibromosilane, phenyltribromosilane, phenyldimethylbromosilane, tolyltribromosilane, phenylisopropyldibromosilane, naphthyltribromosilane, phenylchlorodifluorosilane, phenyldichlorofluorosilane, phenyldibromochlorosilane, diphenylbromofluorosilane, phenylmethylchlorofluorosilane, diphenylchlorofluorosilane, phenylisopropylchlorofluorosilane, ditolylchlorofluorosilane, tolylbromodichlorosilane, and ditolylbromofluorosilane. Preferred silanes are triphenylfluorosilane, triphenylchlorosilane, and triphenylbromosilane. Highly preferred are silanes of the formula $(CH_3)_n SiX_{4-n}$, where n=1-3, and X is, independently, fluorine, chlorine or bromine; especially preferred of these is trimethylfluorosilane.

Yet another type of halogenation agent that can be used in forming the haloaluminoxanes of this invention is a tin compound of the formula $R'_n SnX_{4-n}$, where n=1-3, X is, independently, fluorine, chlorine or bromine, and where R' is, independently, a hydrocarbyl group having from one to about twenty carbon atoms. R' can be a straight chain, branched, cycloalkyl, aryl, or araalkyl group. Preferably, R' is an aryl group, or, more preferably, a straight chain or branched hydrocarbyl group. When R' is an aryl group, it preferably has from six to about twenty carbon atoms; it is more preferred that the aryl group is a phenyl group. When R' is a straight chain or branched hydrocarbyl group, it preferably has from one to about twelve carbon atoms; more preferably, R' has from one to about six carbon atoms; the most preferred straight chain or branched hydrocarbyl group is a methyl group.

Tin compounds that can be used as halogenation agents include trimethylfluorostannane, diethylfluorostannane, di-n-propyldifluorostannane, tri-n-butyl-fluorostannane, dipentyldifluorostannane, cyclohexyltrifluorostannane, diheptyldifluorostannane, trioctylfluorostannane, didodecyldifluorostannane, dichlorodimethylstannane, trichloromethylstannane, triethylchlorostannane, diisopropyldichlorostannane, dicyclobutyldichlorostannane, cyclopentyltrichlorostannane, trihexylchlorostannane, dicycloheptyldichlorostannane, octyltrichlorostannane, dinonyldichlorostannane, decyltrichlorostannane, dimethyldibromostannane, bromotriethylstannane, tribromoethylstannane, cyclopropyltribromostannane, di-n-butyldibromodstannane, pentyltribromostannane, dihexyldibromostannane, trihepylbromostannane, dicyclooctlydibromostannane, dimethylchlorobromostannane, diethylfluorobromostannane, isopropylfluorodichlorostannane, fluorotriphenylstannane, difluorodiphenylstannane, trifluorophenylstannane, fluorotritolylstannane, chlorotriphenylstannane, dichlorodiphenylstannane, trichlorophenylstannane, dichloroditolylstannane, bromotriphenyl stannane, dibromodiphenylstannane, tribromophenyl stannane, tolyltribromostannane, phenyldichlorobromostannane, diphenylfluorochlorostannane, diphenylfluorobromostannane, and the like. Preferred tin compounds are triphenylfluorostannane, triphenylchlorostannane, dichlorodimethylstannane, and triphenylbromostannane. Highly preferred are tin compounds of the formula $(CH_3)_n SnX_{4-n}$, where n=1-3, and X is, independently, fluorine, chlorine or bromine.

Still another type of halogenation agent that can be used in forming the haloaluminoxanes of this invention include a hydrocarbyl aluminum halide of the formula $R''_m AlX_{3-m}$, where m=1 or 2, where X is, independently, fluorine, chlorine or bromine, and where R'' is, independently, a hydrocarbyl group having from one to about twenty carbon atoms. R'' can be a straight chain, branched, cycloalkyl, aryl, or araalkyl group. Preferably, R'' is a straight chain; the straight chain preferably has from one to about ten carbon atoms.

Hydrocarbyl aluminum halides that can be used as halogenation agents include, but are not limited to, methylaluminum difluoride, dimethylaluminum fluoride, ethylaluminum difluoride, diethylaluminum fluoride, isopropylaluminum difluoride, diisopropylaluminum fluoride, n-butylaluminum difluoride, isobutylaluminum difluoride, diisobutylaluminum fluoride, dipentylaluminum fluoride, cyclohexylaluminum difluoride, diheptylaluminum fluoride, dicyclooctylaluminum fluoride, nonylalumium difluoride, decylaluminum difluoride, diundecylaluminum fluoride, phenylaluminum difluoride, diphenylaluminum fluoride, tolylaluminum difluoride, ditolylaluminum fluoride, methylaluminum dichloride, dimethylaluminum chloride, ethylaluminum dichloride, diethylaluminum chloride, diisopropylaluminum chloride, di-n-butylaluminum chloride, isobutylaluminum dichloride, pentylaluminum dichloride, dicyclohexylaluminum chloride, heptylaluminum dichloride, cyclooctylaluminum chloride, dinonylaluminum chloride, didecylaluminum chloride, undecylaluminum chloride, phenylaluminum dichloride, diphenylaluminum chloride, tolylaluminum dichloride, ditolylaluminum chloride, methylaluminum dibromide, dimethylaluminum bromide, ethylaluminum dibromide, diethylaluminum bromide, isopropylaluminum dibromide, isobutylaluminum dibromide, diisobutylaluminum bromide, pentylaluminum bromide, cyclohexylaluminum bromide, heptylaluminum dibromide, cyclooctylaluminum bromide, dinonylalumium bromide, decylaluminum dibromide, undecylaluminum bromide, phenylaluminum dibromide, diphenylaluminum bromide, tolylaluminum dibromide, and ditolylaluminum bromide.

Preferred hydrocarbyl aluminum halides are methylaluminum difluoride, dimethylaluminum fluoride, methylaluminum dichloride, dimethylaluminum chloride, methylaluminum dibromide, and dimethylaluminum bromide. More preferred are methylaluminum difluoride and dimethylaluminum fluoride.

Finally, as alluded to above, mixtures of two or more halogenation agents may be used. This includes mixtures of different halogenation agents within the same type, mixtures of halogenation agents of different types, and mixtures of at least two different halogenation agents within the same type with at least one halogenation agent of a different type. Mixtures may be used in which the halogen elements in the halogenation agents are the same or different. It may be advantageous to use a mixture of halogenation agents, depending on the desired product haloaluminoxane and the properties thereof (e.g., degree of halogenation, solubility, and stability).

Process for Producing Haloaluminoxanes

The formation of these haloaluminoxane compositions is generally rapid, and the by-products of the formation do not appear to adversely affect the properties of the desired haloaluminoxane composition.

A process for producing the new haloaluminoxanes of this invention comprises mixing, in an inert, anhydrous environment, (a) at least one aluminoxane and (b) at least one halogenation agent which is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or (vi) mixtures of any two or more of (i)-(v), such that a haloaluminoxane composition is formed. The amount of halogen atoms is in the range of about 0.5 mole % to about 15 mole % relative to aluminum atoms.

The aluminoxane and the halogenation agents are as described above for the compositions of this invention.

Typically, the inert, anhydrous environment is an anhydrous liquid hydrocarbon solvent, preferably an aromatic hydrocarbon. The aromatic hydrocarbon is usually one or more of benzene, toluene, xylene, mesitylene, ethylbenzene, diethylbenzene, 1,2,4-triethylbenzene, 1,3,5-triethylbenzene, amylbenzene, tetrahydronaphthalene, and the like. Mixtures of solvents may be used. Toluene is a particularly preferred aromatic solvent.

Reactions of halogenation agents having fluorine atom(s) are more exothermic than those using halogenation agents having chlorine or bromine atom(s). Cooling is not usually necessary even though the reaction is exothermic. Cooling of the reaction medium, e.g., with an ice bath or recirculating coolant, dilution of the aluminoxane solution, and dilution of the halogenation agent, are acceptable methods for absorbing the heat of reaction. A preferred method is dilution of the halogenation agent (e.g., with an anhydrous liquid hydrocarbon solvent); such measures are less preferred when the halogenation agent is a siloxane with labile halogen atom(s) because such reactions tend to be less exothermic than those utilizing halohydrocarbons. Generally, to form the haloaluminoxane complexes, excess heat should be avoided. In preparations of partially halogenated aluminoxanes with a halohydrocarbon as the halogenation agent, the mixture of aluminoxane and halogenation agent is usually heated or aged. When preparing a partially halogenated aluminoxane from a halohydrocarbon, the temperature is preferably in the range of about 30° to about 80° C. Aging or adding heat to the process to form a partially halogenated aluminoxane is usually not necessary when using a siloxane, silane, tin compound, or hydrocarbyl aluminum compound as the halogenation agent.

Generally, it is preferred to add the halogenation agent to the aluminoxane solution. More preferably, the halogenation agent is diluted and then added to the aluminoxane solution; dilution is less preferred when the halogenation agent is a siloxane with labile halogen atom(s). When the halogenation agent is diluted and added to the aluminoxane solution, cooling is not usually necessary.

When the halogenation agent and the aluminoxane are brought together such that the aluminoxane is in an environment of excess halogenation agent (e.g., when the halogenation agent is added to the aluminoxane), it has been found that the reaction can be quite exothermic, causing rapid evaporation of solvent, and possibly ejection of material from the reaction vessel if removal of the heat generated was not rappid enough. Also, when the aluminoxane is in an environment of excess halogenation agent, overhalogenation of the aluminoxane oftenn occurs, producing halogenated aluminoxanes having greater amounts of halogen than the haloaluminoxanes of the present invention.

As mentioned previously, the reaction of the aluminoxane and the halogenation agent can be quite rapid, and is often finished in a few minutes on the laboratory scale. For example, in a lab-scale reaction of methylaluminoxane with α,α,α-trifluorotoluene (δ-64 ppm in $^{19}$F NMR; 2-4 mol % fluorine relative to aluminum) at ambient temperature, the fluorine atoms of the α,α,α-trifluorotoluene became undetectable by $^{19}$F NMR in less than 5 minutes. At larger scales, longer times may be necessary for the reaction to complete, due to the greater length of time needed to achieve thorough mixing of the aluminoxane and halogenation agent. It has been observed on the laboratory scale that siloxanes react more slowly with aluminoxanes than do some of the halohydrocarbons.

As described briefly above, another process for preparing haloaluminoxanes of the invention comprises contacting at least one aluminum hydrocarbyl with at least one halogenation agent during the hydrolysis of the aluminum hydrocarbyl. halogenation agent which is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or (vi) mixtures of any two or more of (i)-(v), such that a haloaluminoxane composition is formed, and the amount of halogen atoms is in the range of about 0.5 mole % to about 15 mole % relative to aluminum atoms.

As described above, methods for hydrolysis of aluminum hydrocarbyls to form aluminoxanes are well known in the art. In the preparation of haloaluminoxane compositions during the hydrolysis of aluminum hydrocarbyls, the preferences for halogenation agents is the same as detailed above.

Aluminum hydrocarbyls that can be used in the hydrolysis include, but are not limited to, trimethylaluminum, ethyldimethylaluminum, triethylaluminum, tri-n-propyl-aluminum, tri-n-butylaluminum, triisobutylaluminum, tri-n-hexylaluminoxane, tri-n-octylaluminum, tridecylaluminum, tridodecylaluminum, tris(tetradecy)laluminum, tri(hexadecyl)aluminum, tri(octadecyl)aluminum, triphenylaluminum, tritolylaluminum, and the like. Mixtures of two or more aluminum hydrocarbyls may be used.

Preferred aluminum hydrocarbyls are those in which the hydrocarbyl groups are saturated, particularly those aluminoxanes in which the hydrocarbyl groups have from one to about twenty carbon atoms. More preferred are aluminum hydrocarbyls in which the saturated hydrocarbyl groups have from one to about six carbon atoms. Even more preferred are trimethylaluminum, triethylaluminum, tri-n-butylaluminum, and triiso-butylaluminum. Highly preferred are trimethylaluminum and triethylaluminum. The most highly preferred aluminum hydrocarbyl is trimethylaluminum.

Supported Compositions and Cocatalysts of this Invention

This invention also provides new supported haloaluminoxanes. These supported haloaluminoxanes include both supported haloaluminoxane complexes and supported partially halogenated aluminoxanes. Instead of isolating the haloaluminoxanes of this invention as particulate solids, the haloaluminoxanes can be deposited on a support.

To produce the new supported haloaluminoxanes of this invention involves a process comprising A) contacting a haloaluminoxane composition with a support material, or B) contacting a support material with (a) and (b), such that a supported haloaluminoxane is formed. Here, (a) is at least one aluminoxane and (b) is at least one halogenation agent which is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R" is, independently, a hydrocarbyl group having from one to about twenty carbon atoms; or (vi) mixtures of any two or more of (i)-(v).

The amount of halogen atoms in either the haloaluminoxane composition or in the ratio of (a) to (b) is in the range of about 0.5 mole % to about 15 mole % relative to aluminum atoms.

Generally, the addition of heat is to be avoided during this process when forming a supported haloaluminoxane complex. Operations for forming a supported partially halogenated aluminoxane may be carried out at temperatures in the range of about 20 to about 80° C., and preferably at temperatures in the range of about 25 to about 60° C. However, suitable temperatures outside these ranges are permissible.

Optionally, these supported haloaluminoxanes (both haloaluminoxane complexes and partially halogenated aluminoxanes) can be recovered from the mixture formed (e.g., by filtration), and if desired, can be washed with a liquid diluent inert to the haloaluminoxane, and also can then be dried, if desired. Thus when a catalyst support material such as silica or a porous polyolefin support is used in forming the supported haloaluminoxane, the liquid diluent used in the formation and the liquid diluent used in the optional subsequent washing of the recovered supported haloaluminoxane can be an aromatic solvent. Other types of diluents such as at least one liquid paraffinic or cycloparaffinic hydrocarbon or a mixture of either or both with an aromatic solvent can be used for such washing, if desired.

Catalyst support materials used in the practice of this invention may be any finely divided inorganic solid support, such as talc, clay, silica, alumina, silica-alumina, or mixtures thereof or a particulate resinous support material such as spheroidal, particulate, or finely-divided polyethylene, polyvinylchloride, polystyrene, or the like. Preferred support materials are inorganic particulate solid catalyst supports or carrier materials such as magnesium halides, or the like, and particularly inorganic oxides, aluminum silicates, or inorganic compositions containing inorganic oxides, such as kaolinite, attapulgite, montmorillonite, illite, bentonite, halloysite, and similar refractory clays. Inorganic oxides that may be employed either alone or in combination with silica, alumina, or silica-alumina are magnesia, titania, zirconia, and the like. The inorganic oxides may be dehydrated to remove water. If desired, the residual surface hydroxyl groups in the inorganic solid porous support may be removed by additional heating or by reaction with chemical dehydrating agents such as lithium alkyl, silylchloride, aluminum alkyls, or preferably with a haloaluminoxane of this invention.

As an alternative, the support material may be chemically dehydrated. Chemical dehydration is accomplished by slurrying the support in an inert low boiling solvent such as, for example, heptane, in the presence of the dehydrating agent such as for example, triethylaluminum in a moisture and oxygen-free atmosphere.

Preferred catalyst support materials are inorganic oxides. More preferred supports are silica, alumina, and silica-alumina. Particularly preferred as the support material is particulate silica, especially porous particulate silica.

The specific particle size, surface area and pore volume of the inorganic support material determine the amount of inorganic support material that is desirable to employ in preparing the catalyst compositions, as well as affecting the properties of polymers formed with the aid of the catalyst compositions. These properties are frequently taken into consideration in choosing an inorganic support material for use in a particular aspect of the invention. A suitable inorganic support such as silica typically will have a particle diameter in the range of 0.1 to 600 microns, preferably in the range of 0.3 to 100 microns; a surface area in the range of 50 to 1000 m²/g, preferably in the range of 100 to 500 m²/g; and a pore volume in the range of about 0.3 to 5.0 cc/g, preferably in the range of 0.5 to 3.5 cc/g. It is also desirable to employ supports with pore diameters in the range of about 50 to about 500 angstroms. To ensure its use in dehydrated form the support material may be heat treated at 100-1000° C. for a period of 1-100 hours, preferably 3-24 hours. The treatment may be carried out in a vacuum or while purging with a dry inert gas such as nitrogen.

Transition Metal Catalyst Compounds

Also provided by this invention are new polymerization catalyst compositions in which the cocatalyst used is a new haloaluminoxane of this invention. These new polymerization catalyst compositions can be used in solution polymerizations or they can be used in supported form in slurry or gas phase polymerizations. These catalytic systems can be used for the polymerization of olefins and/or other monomers which on polymerization result in formation of polymerized ethylene linkages.

Typically unsupported catalysts are formed by mixing or otherwise interacting a haloaluminoxane of this invention with the transition metal catalyst compound in an inert aromatic solvent. The resultant unsupported reaction product, which is an embodiment of this invention and an active olefin polymerization catalyst, can be formed using various proportions of these components. For example, the molar ratio of aluminum to transition metal can be in the range of about 20:1 to about 2000:1, and preferably is in the range of about 20:1 to about 500:1.

One type of the polymerization catalysts of this invention is an unsupported reaction product between (i) at least one catalyst compound or complex of a transition metal of Groups 3 to 10 of the Periodic Table including the lanthanide and actinide series, and (ii) at least one haloaluminoxane of this invention. One way of producing these new catalyst compositions is to form a catalyst in solution by bringing together either in a polymerization reactor or zone or in a separate vessel, at least (i) a catalyst compound or complex of a transition metal of Groups 3 to 10 of the Periodic Table including the lanthanide and actinide series, (ii) a haloaluminoxane of this invention, and (iii) a polymerization solvent. These components can be fed separately in any order or any two of them can be premixed and fed as a mixture, with the other component being fed before, during or after the feeding of such mixture to the polymerization reactor or zone or to the separate vessel. If a separate vessel is used, the catalyst formed therein is promptly delivered into the polymerization reactor or zone. In all cases the customary inert atmospheres and anhydrous polymerization conditions should be observed. The resultant mixture formed in this operation is a solution of a catalyst of this invention in which polymerization of the monomer or combination of monomers is carried out.

For the haloaluminoxane complexes, the complex can be formed and then mixed with the transition metal catalyst compound, or prepared in situ in the presence of the transition metal catalyst compound.

For the partially halogenated aluminoxane, the partially halogenated aluminoxane is normally and preferably prepared and then mixed with the transition metal catalyst compound. Alternatively, the partially halogenated aluminoxane can be formed in the presence of the transition metal catalyst compound, because by-products of the preparation of the partially halogenated aluminoxane generally do not interfere with the polymerization.

The new haloaluminoxanes are so effective as cocatalysts that they can be used with any known transition metal catalyst compound in which the transition metal thereof is a Group 3 to 10 transition metal of the Periodic Table including compounds of a metal of the lanthanide or actinide series. The Periodic Table referred to herein is that appearing on page 27 of the Feb. 4, 1985 issue of *Chemical & Engineering News*. Suitable catalyst compounds can also be described as d- and f-block metal compounds. See, for example, the Periodic Table appearing on page 225 of Moeller, et al., *Chemistry*, Second Edition, Academic Press, copyright 1984. As regards the metal constituent, preferred are compounds of Fe, Co, Ni, Pd, and V. More preferred are compounds of the metals of Groups 4-6 (Ti, Zr, Hf, V, Nb, Ta, Cr, Mo, and W), and most preferred are the Group 4 metals, especially titanium, zirconium, or hafnium.

Thus the transition metal catalyst compounds used in this invention can be one or more of any Ziegler-Natta catalyst compound, any metallocene, any compound of constrained geometry, any late transition metal complex, or any other transition metal compound or complex reported in the literature or otherwise generally known in the art to be an effective catalyst compound when suitably activated, including mixtures of at least two different types of such transition metal compounds or complexes, such as for example a mixture of a metallocene and a Ziegler-Natta olefin polymerization catalyst compound.

Among the transition metal compounds of the metals of Groups 3, 4, 5, and 6 which can be used as the transition metal component of the catalyst compositions of and used in this invention are the compounds of such metals as scandium, titanium, zirconium, hafnium, cerium, vanadium, niobium, tantalum, chromium, molybdenum, tungsten, thorium and uranium often referred to as Ziegler-Natta type olefin polymerization catalysts. Preferred compounds of this type can be represented by the formula $MX_n(OR)_m$ in which M represents the transition metal atom or a transition metal atom cation containing one or two oxygen atoms such as vanadyl, zirconyl, or uranyl, X represents a halogen atom, OR represents a hydrocarbyloxy group having up to about 18 carbon atoms, preferably up to about 8 carbon atoms, and more preferably alkyl of up to about 4 carbon atoms, such as an alkyl, cycloalkyl, cycloalkylalkyl, aryl, or aralkyl, group and n and m are positive integers except that either one of them (but not both) can be zero, and where n+m is the valence state of the transition metal. Illustrative of some of the transition metal compounds which can he used are, for example, titanium dibromide, titanium tribromide, titanium tetrabromide, titanium dichloride, titanium trichloride, titanium tetrachloride, titanium trifluoride, titanium tetrafluoride, titanium diiodide, titanium triiodide, titanium tetraiodide, zirconium dibromide, zirconium tribromide, zirconium tetrabromide, zirconium dichloride, zirconium trichloride, zirconium tetrachloride, zirconium tetrafluoride, zirconium tetraiodide, hafnium tetrafluoride, hafnium tetrachloride, hafnium tetrabromide, hafnium tetraiodide, hafnium trichloride, hafnium tribromide, hafnium triiodide, vanadium dichloride, vanadium trichloride, vanadium tetrachloride, vanadium tetrabromide, vanadium tribromide, vanadium dibromide, vanadium trifluoride, vanadium tetrafluoride, vanadium pentafluoride, vanadium diiodide, vanadium triiodide, vanadium tetraiodide, vanadyl chloride, vanadyl bromide, niobium pentabromide, niobium pentachloride, niobium pentafluoride, tantalum pentabromide, tantalum pentachloride, tantalum pentafluoride, chromous bromide, chromic bromide, chromous chloride, chromic chloride, chromous fluoride, chromic fluoride, molybdenum dibromide, molybdenum tribromide, molybdenum tetrabromide, molybdenum dichloride, molybdenum trichloride, molybdenum tetrachloride, molybdenum pentachloride, molybdenum hexafluoride, lanthanum trichloride, cerous fluoride, cerous chloride, cerous bromide, cerous iodide, ceric fluoride, uranium trichloride, uranium tetrachloride, uranium tribromide, uranium tetrabromide, thorium tetrachloride, thorium tetrabromide, and the like. Among the hydrocarbyloxides and mixed halide/hydrocarbyloxides of the transition metals are Ti(OCH$_3$)$_4$, Ti(OCH$_3$)Cl$_3$, Ti(OCH$_3$)Br$_3$, Ti(OCH$_3$)$_2$I$_2$, Ti(OC$_2$H$_5$)$_4$, Ti(OC$_2$H$_5$)$_3$Cl, Ti(OC$_2$H$_5$)Cl$_3$, Ti(OC$_2$H$_5$)Br$_3$, Ti(OC$_4$H$_9$)Br$_3$, Ti(OC$_2$H$_5$)I$_3$, Ti(OC$_3$H$_7$)$_2$Cl$_2$, Ti(O-iso-C$_3$H$_7$)$_3$Cl, Ti(O-iso-C$_3$H$_7$)$_2$Cl$_2$, Ti(O-iso-C$_3$H$_7$)Cl$_3$, Ti(OC$_4$H$_9$)$_3$Cl, Ti(OC$_4$H$_9$)$_2$Cl$_2$, Ti(OC$_4$H$_9$)Cl$_3$, Ti(OC$_6$H$_5$)Cl$_3$, Ti(O-p-CH$_3$C$_6$H$_4$)Cl$_3$, Ti(OC$_6$H$_{13}$)$_2$Cl$_2$, Ti(OC$_6$H$_{13}$)Cl$_3$, Ti(O-cyclo-C$_6$H$_{11}$)Cl$_3$, Ti(OC$_8$H$_{17}$)$_2$Br$_2$, Ti(O-2-EtHex)$_4$, Ti(OC$_{12}$H$_{25}$)Cl$_3$, Ti(OC$_{17}$H$_{18}$)$_2$Br$_2$, Zr(OC$_2$H$_5$)$_4$, Zr(OC$_4$H$_9$)$_4$, Zr(OC$_5$H$_{11}$)$_4$, ZrCl(OC$_2$H$_5$)$_3$, ZrCl$_2$(OC$_2$H$_5$)$_2$, ZrCl$_3$(OC$_2$H$_5$), ZrCl(OC$_4$H$_9$)$_3$, ZrCl$_2$(OC$_4$H$_9$)$_2$, ZrCl$_3$(OC$_4$H$_9$), Hf(OC$_4$H$_9$)$_4$, Hf(OC$_4$H$_9$)$_3$Cl, VO(OC$_2$H$_5$)$_3$, VOCl(OCH$_3$)$_2$, VOCl(OC$_2$H$_5$)$_2$, VOCl(OC$_3$H$_7$)$_2$, VOCl(O-iso-C$_3$H$_7$)$_2$, VOCl$_2$(OCH$_3$), VOCl$_2$(OC$_2$H$_5$), VOCl$_2$(OC$_3$H$_7$), VOCl$_2$(O-iso-C$_3$H$_7$), VOBr(OCH$_3$)$_2$, VOBr(OC$_2$H$_5$)$_2$, VOBr(O-iso-C$_4$H$_9$)$_2$, VOBr$_2$(OC$_3$H$_7$), VOBr$_2$(O-iso-C$_3$H$_7$), VOBr$_2$(OC$_4$H$_9$), VOBr$_2$(O-iso-C$_4$H$_9$), VOI(OCH$_3$)$_2$, VOI(OC$_2$H$_5$)$_2$, VOI$_2$(OCH$_3$), VOI$_2$(O-cyclo-C$_3$H$_5$), VOI$_2$(OC$_5$H$_{11}$), VOI$_2$(O-cyclo-C$_6$H$_{11}$), Cr(O-iso-C$_4$H$_9$)$_3$, Mo(OC$_2$H$_5$)$_3$, and the like. Carboxylic acid salts and various chelates of the transition metal can also be used but in general are less preferred. A few non-limiting examples of such salts and chelates include zirconyl acetate, uranyl butyrate, chromium acetate, chromium(III) oxy-2-ethylhexanoate, chromium(III) 2-ethylhexanoate, chromium(III) dichloroethylhexanoate, chromium (II) 2-ethylhexanoate, titanium(IV) 2-ethylhexanoate, bis(2,4-pentanedionate)titanium oxide, bis(2,4-pentanedionate) titanium dichloride, bis(2,4-pentanedionate)titanium dibutoxide, vanadyl acetylacetonate, chromium acetylacetonate, niobium acetylacetonate, zirconyl acetylacetonate, chromium octylacetoacetate, and the like. Also, transition metal alkyls such as tetramethyl titanium, methyl titanium trichloride, tetraethyl zirconium, tetraphenyl titanium, and the like can be used.

Preferred transition metal compounds of the well-known Ziegler-Natta catalyst compounds are those of the Group 4 metals, including the alkoxides, halides, and mixed halide/alkoxide compounds. More preferred are TiCl$_4$, ZrCl$_4$, HfCl$_4$, and TiCl$_3$, with TiCl$_4$ being most preferred. Such more preferred compounds can be used in chelated form in order to facilitate solubility. Suitable chelated catalysts of this type are known and reported in the literature.

Metallocenes are another broad class of olefin polymerization catalyst compounds with which the haloaluminoxanes of this invention can be used in forming novel highly effective catalysts of this invention. As used herein, the term "metallocene" includes metal derivatives which contain at least one cyclopentadienyl moiety. Suitable metallocenes are well known in the art and include the metallocenes of Groups 3, 4, 5, 6, lanthanide and actinide metals, for example, the metallocenes which are described in U.S. Pat. Nos. 2,864,843; 2,983,740; 4,665,046; 4,874,880; 4,892,851; 4,931,417; 4,952,713; 5,017,714; 5,026,798; 5,036,034; 5,064,802; 5,081,231; 5,145,819; 5,162,278; 5,245,019; 5,268,495; 5,276,208; 5,304,523; 5,324,800; 5,329,031; 5,329,033; 5,330,948; 5,347,025; 5,347,026; and 5,347,752, whose teachings with respect to such metallocenes are incorporated herein by reference.

Metallocene structures in this specification are to be interpreted broadly, and include structures containing 1, 2, 3 or 4 Cp or substituted Cp rings. Thus metallocenes suitable for use in this invention can be represented by Formula (I):

$$B_aCp_bMX_cY_d \qquad (I)$$

where Cp, independently in each occurrence, is a cyclopentadienyl-moiety-containing group which typically has in the range of 5 to about 24 carbon atoms; B is a bridging group or ansa group that links two Cp groups together or alternatively carries an alternate coordinating group such as alkylaminosilylalkyl, silylamido, alkoxy, siloxy, aminosilylalkyl, or analogous monodentate hetero atom electron donating groups; M is a d- or f-block metal atom; each X and each Y is, independently, a group that is bonded to the d- or f-block metal atom; a is 0 or 1; b is a whole integer from 1 to 3 (preferably 2); c is at least 2; d is 0 or 1. The sum of b, c, and d is sufficient to form a stable compound, and often is the coordination number of the d- or f-block metal atom.

Cp is, independently, a cyclopentadienyl, indenyl, fluorenyl or related group that can π-bond to the metal, or a hydrocarbyl-, halo-, halohydrocarbyl-, hydrocarbylmetalloid-, and/or halohydrocarbylmetalloid-substituted derivative thereof. Cp typically contains up to 75 non-hydrogen atoms. B, if present, is typically a silylene (—SiR$_2$—), benzo (C$_6$H$_4$<), substituted benzo, methylene (—CH$_2$—), substituted methylene, ethylene (—CH$_2$CH$_2$—), or substituted ethylene bridge. M is preferably a metal atom of Groups 4-6, and most preferably is a Group 4 metal atom, especially hafnium, and most especially zirconium. X can be a divalent substituent such as an alkylidene group, a cyclometallated hydrocarbyl group, or any other divalent chelating ligand, two loci of which are singly bonded to M to form a cyclic moiety which includes M as a member. Each X, and if present Y, can be, independently in each occurrence, a halogen atom, a hydrocarbyl group (alkyl, cycloalkyl, alkenyl, cycloalkenyl, aryl, aralkyl, etc.), hydrocarbyloxy, (alkoxy, aryloxy, etc.) siloxy, amino or substituted amino, hydride, acyloxy, triflate, and similar univalent groups that form stable metallocenes. The sum of b, c, and d is a whole number, and is often from 3-5. When M is a Group 4 metal or an actinide metal, and b is 2, the sum of c and d is 2, c being at least 1. When M is a Group 3 or Lanthanide metal, and b is 2, c is 1 and d is zero. When M is a Group 5 metal, and b is 2, the sum of c and d is 3, c being at least 2.

Also useful in this invention are compounds analogous to those of Formula (I) where one or more of the Cp groups are replaced by cyclic unsaturated charged groups isoelectronic with Cp, such as borabenzene or substituted borabenzene, azaborole or substituted azaborole, and various other isoelectronic Cp analogs. See for example Krishnamurti, et al., U.S. Pat. Nos. 5,554,775 and 5,756,611.

In one preferred group of metallocenes, b is 2, i.e., there are two cyclopentadienyl-moiety containing groups in the molecule, and these two groups can be the same or they can be different from each other.

Another sub-group of useful metallocenes which can be used in the practice of this invention are metallocenes of the type described in WO 98/32776 published Jul. 30, 1998. These metallocenes are characterized in that one or more cyclopentadienyl groups in the metallocene are substituted by one or more polyatomic groups attached via a N, O, S, or P atom or by a carbon-to-carbon double bond. Examples of such substituents on the cyclopentadienyl ring include —OR, —SR, —NR$_2$, —CH=, —CR=, and —PR$_2$, where R can be the same or different and is a substituted or unsubstituted $C_1$-$C_{16}$ hydrocarbyl group, a tri-$C_1$-$C_8$ hydrocarbylsilyl group, a tri-$C_1$-$C_8$ hydrocarbyloxysilyl group, a mixed $C_1$-$C_8$ hydrocarbyl and $C_1$-$C_8$ hydrocarbyloxysilyl group, a tri-$C_1$-$C_8$ hydrocarbylgermyl group, a tri-$C_1$-$C_8$ hydrocarbyloxygermyl group, or a mixed $C_1$-$C_8$ hydrocarbyl and $C_1$-$C_8$ hydrocarbyloxygermyl group.

Examples of metallocenes to which this invention is applicable include such compounds as:
bis(cyclopentadienyl)zirconium dimethyl;
bis(cyclopentadienyl)zirconium dichloride;
bis(cyclopentadienyl)zirconium monomethylmonochloride;
bis(cyclopentadienyl)titanium dichloride;
bis(cyclopentadienyl)titanium difluoride;
cyclopentadienylzirconium tri-(2-ethylhexanoate);
bis(cyclopentadienyl)zirconium hydrogen chloride;
bis(cyclopentadienyl)hafnium dichloride;
racemic and meso dimethylsilanylene-bis(methylcyclopentadienyl)hafnium dichloride;
racemic dimethylsilanylene-bis(indenyl)hafnium dichloride;
racemic ethylene-bis(indenyl)zirconium dichloride;
($\eta^5$-indenyl)hafnium trichloride;
($\eta^5$-$C_5Me_5$)hafnium trichloride;
racemic dimethylsilanylene-bis(indenyl)thorium dichloride;
racemic dimethylsilanylene-bis(4,7-dimethyl-1-indenyl)zirconium dichloride;
racemic dimethyl-silanylene-bis(indenyl)uranium dichloride;
racemic dimethylsilanylene-bis(2,3,5-trimethyl-1-cyclopentadienyl)zirconium dichloride;
racemic dimethyl-silanylene(3-methylcyclopentadienyl) hafnium dichloride;
racemic dimethylsilanylene-bis(1-(2-methyl-4-ethyl)indenyl)zirconium dichloride;
racemic dimethylsilanylene-bis(2-methyl-4,5,6,7-tetrahydro-1-indenyl)zirconium dichloride;
bis(pentamethylcyclopentadienyl)thorium dichloride;
bis(pentamethylcyclopentadienyl)uranium dichloride;
(tert-butylamido)dimethyl(tetramethyl-$\eta^5$-cyclopentadienyl)silanetitanium dichloride;
(tert-butylamido)dimethyl(tetramethyl-$\eta^5$-cyclopentadienyl)silane chromium dichloride;
(tert-butylamido)dimethyl(-$\eta^5$-cyclopentadienyl)silanetitanium dichloride;
(tert-butylamido)dimethyl(tetramethyl-$\eta^5$-cyclopentadienyl)silanemethyltitanium bromide;
(tert-butylamido)(tetramethyl-$\eta^5$-cyclopentadienyl)-1,2-ethanediyluranium dichloride;
(tert-butylamido)(tetramethyl-$\eta^5$-cyclopentadienyl)-1,2-ethanediyltitanium dichloride;
(methylamido)(tetramethyl-$\eta^5$-cyclopentadienyl)-1,2-ethanediylcerium dichloride;
(methylamido)(tetramethyl-$\eta^5$-cyclopentadienyl)-1,2-ethanediyltitanium dichloride;
(ethylamido)(tetramethyl-$\eta^5$-cyclopentadienyl)methylenetitanium dichloride;
(tert-butylamido)dibenzyl(tetramethyl-$\eta^5$-cyclopentadienyl)-silanebenzylvanadium chloride;
(benzylamido)dimethyl(indenyl)silanetitanium dichloride;
(phenylphosphido)dimethyl(tetramethyl-$\eta^5$-cyclopentadienyl)silanebenzyltitanium chloride;
rac-dimethylsilylbis(2-methyl-1-indenyl)zirconium dimethyl;
rac-ethylenebis(1-indenyl)zirconium dimethyl;
bis(methylcyclopentadienyl)titanium dimethyl;
bis(methylcyclopentadienyl)zirconium dimethyl;
bis(n-butylcyclopentadienyl)zirconium dimethyl;
bis(dimethylcyclopentadienyl)zirconium dimethyl;
bis(diethylcyclopentadienyl)zirconium dimethyl;
bis(methyl-n-butylcyclopentadienyl)zirconium dimethyl;
bis(n-propylcyclopentadienyl)zirconium dimethyl;
bis(2-propylcyclopentadienyl)zirconium dimethyl;
bis(methylethylcyclopentadienyl)zirconium dimethyl;
bis(indenyl)zirconium dimethyl;
bis(methylindenyl)zirconium dimethyl;
dimethylsilylenebis(indenyl)zirconium dimethyl;
dimethylsilylenebis(2-methylindenyl)zirconium dimethyl;
dimethylsilylenebis(2-ethylindenyl)zirconium dimethyl;
dimethylsilylenebis(2-methyl-4-phenylindenyl)zirconium dimethyl;
1,2-ethylenebis(indenyl)zirconium dimethyl;
1,2-ethylenebis(methylindenyl)zirconium dimethyl;
2,2-propylidenebis(cyclopentadienyl)(fluorenyl)zirconium dimethyl;
dimethylsilylenebis(6-phenylindenyl)zirconium dimethyl;
bis(methylindenyl)zirconium benzyl methyl;
ethylenebis[2-(tert-butyldimethylsiloxy)-1-indenyl]zirconium dimethyl;
dimethylsilylenebis(indenyl)chlorozirconium methyl;
5-(cyclopentadienyl)-5-(9-fluorenyl) 1-hexene zirconium dimethyl;
dimethylsilylenebis(2-methylindenyl)hafnium dimethyl;
dimethylsilylenebis(2-ethylindenyl)hafnium dimethyl;
dimethylsilylenebis(2-methyl-4-phenylindenyl)hafnium dimethyl;
2,2-propylidenebis(cyclopentadienyl)(fluorenyl)hafnium dimethyl;
bis(9-fluorenyl)(methyl)(vinyl)silane zirconium dimethyl,
bis(9-fluorenyl)(methyl)(prop-2-enyl)silane zirconium dimethyl,
bis(9-fluorenyl)(methyl)(but-3-enyl)silane zirconium dimethyl,
bis(9-fluorenyl)(methyl)(hex-5-enyl)silane zirconium dimethyl,
bis(9-fluorenyl)(methyl)(oct-7-enyl)silane zirconium dimethyl,
(cyclopentadienyl)(1-allylindenyl)zirconium dimethyl,
bis(1-allylindenyl)zirconium dimethyl,
(9-(prop-2-enyl)fluorenyl)(cyclopentadienyl)zirconium dimethyl,
(9-(prop-2-enyl)fluorenyl)(pentamethylcyclopentadienyl) zirconium dimethyl,
bis(9-(prop-2-enyl)fluorenyl)zirconium dimethyl,
(9-(cyclopent-2-enyl)fluorenyl)(cyclopentadienyl)zirconium dimethyl,
bis(9-(cyclopent-2-enyl)(fluorenyl)zirconium dimethyl,
5-(2-methylcyclopentadienyl)-5(9-fluorenyl)-1-hexene zirconium dimethyl,
1-(9-fluorenyl)-1-(cyclopentadienyl)-1-(but-3-enyl)-1-(methyl)methane zirconium dimethyl,
5-(fluorenyl)-5-(cyclopentadienyl)-1-hexene hafnium dimethyl,
(9-fluorenyl)(1-allylindenyl)dimethylsilane zirconium dimethyl,
1-(2,7-di(alpha-methylvinyl)(9-fluorenyl)-1-(cyclopentadienyl)-1,1-dimethylmethane zirconium dimethyl,
1-(2,7-di(cyclohex-1-enyl)(9-fluorenyl))-1-(cyclopentadienyl)-1,1-methane zirconium dimethyl,
5-(cyclopentadienyl)-5-(9-fluorenyl)-1-hexene titanium dimethyl,
5-(cyclopentadienyl)-5-(9-fluorenyl)1-hexene titanium dimethyl,
bis(9-fluorenyl)(methyl)(vinyl)silane titanium dimethyl,
bis(9-fluorenyl)(methyl)(prop-2-enyl)silane titanium dimethyl, bis(9-fluorenyl)(methyl)(but-3-enyl)silane titanium dimethyl,
bis(9-fluorenyl)(methyl)(hex-5-enyl)silane titanium dimethyl,
bis(9-fluorenyl)(methyl)(oct-7-enyl)silane titanium dimethyl,
(cyclopentadienyl)(1-allylindenyl)titanium dimethyl,
bis(1-allylindenyl)titanium dimethyl,
(9-(prop-2-enyl)fluorenyl)(cyclopentadienyl)hafnium dimethyl,
(9-(prop-2-enyl)fluorenyl)(pentamethylcyclopentadienyl) hafnium dimethyl,
bis(9-(prop-2-enyl)fluorenyl)hafnium dimethyl,
(9-(cyclopent-2-enyl)fluorenyl)(cyclopentadienyl)hafnium dimethyl,
bis(9-(cyclopent-2-enyl)(fluorenyl)hafnium dimethyl,
5-(2-methylcyclopentadienyl)-5(9-fluorenyl)-1-hexene hafnium dimethyl,
5-(fluorenyl)-5-(cyclopentadienyl)-1-octene hafnium dimethyl,
(9-fluorenyl)(1-allylindenyl)dimethylsilane hafnium dimethyl.
(tert-butylamido)dimethyl(tetramethylcyclopentadienyl)silane titanium(1,3-pentadiene);
(cyclopentadienyl)(9-fluorenyl)diphenylmethane zirconium dimethyl;
(cyclopentadienyl)(9-fluorenyl)diphenylmethane hafnium dimethyl;
dimethylsilanylene-bis(indenyl)thorium dimethyl;
dimethylsilanylene-bis(4,7-dimethyl-1-indenyl)zirconium dimethyl;
dimethylsilanylene-bis(indenyl)uranium dimethyl;
dimethylsilanylene-bis(2-methyl-4-ethyl-1-indenyl)zirconium dimethyl;
dimethylsilanylene-bis(2-methyl-4,5,6,7-tetrahydro-1-indenyl)zirconium dimethyl;
(tert-butylamido)dimethyl(tetramethyl-$\eta^5$-cyclopentadienyl)silane titanium dimethyl;
(tert-butylamido)dimethyl(tetramethyl-$\eta^5$-cyclopentadienyl)silane chromium dimethyl;
(tert-butylamido)dimethyl(tetramethyl-$\eta^5$-cyclopentadienyl)silane titanium dimethyl;
(phenylphosphido)dimethyl(tetramethyl-$\eta^5$-cyclopentadienyl)silane titanium dimethyl; and
[dimethylsilanediylbis(indenyl)]scandium methyl.

In many cases the metallocenes such as referred to above will exist as racemic mixtures, but pure enantiomeric forms or mixtures enriched in a given enantiomeric form can be used.

Other organometallic catalytic compounds with which the haloaluminoxanes of this invention can be used in forming novel catalysts of this invention are the late transition metal catalyst described, for example, in U.S. Pat. No. 5,516,739 to Barborak, et al.; U.S. Pat. No. 5,561,216 to Barborak, et al.; U.S. Pat. No. 5,866,663 to Brookhart, et al; U.S. Pat. No. 5,880,241 to Brookhart, et al; and U.S. Pat. No. 6,114,483 to Coughlin, et al. Such catalysts are sometimes referred to herein collectively as "a Brookhart-type late transition metal catalyst compound or complex".

Other transition metal catalyst compounds and catalyst complexes that can be used in the practice of this invention include catfluoro nickel, palladium, iron, and cobalt complexes containing diimine and bisoxazoline ligands such as described in Johnson et al. WO 96/23010; palladium and nickel catalysts containing selected bidentate phosphorus-containing ligands such as described in EP 381,495; catfluoro α-diimine-based nickel and palladium complexes such as described by Johnson et al. in *J. Am. Chem. Soc.,* 1995, 117, 6414, see also Brown et al. WO 97/17380; nickel complexes such as described by Johnson et al. in U.S. Pat. No. 5,714,556; cobalt(III) cyclopentadienyl catalytic systems such as described by Schmidt et al. in *J. Am. Chem. Soc.,* 1985, 107, 1443, and by Brookhart et al. in *Macromolecules,* 1995, 28, 5378; anfluoro phosphorus, oxygen donors ligated to nickel(II) such as described by Klabunde in U.S. Pat. Nos. 4,716,205, 4,906,754, 5,030,606, and 5,175,326; Group 8-10 transition metal complexes coordinated with a bidentate ligand such as described in WO 98/40374; transition metal complexes with bidentate ligands containing pyridine or quinoline moieties such as described in U.S. Pat. No. 5,637,660; quinolinoxy or pyridinoxy-substituted Group 4 transition metal trihalides such as described in U.S. Pat. No. 6,020,493; nickel complexes such as described by bis(ylide)nickel complexes such as described by Starzewski et al. in *Angew. Chem. Int. Ed. Engl.,* 1987, 26, 63, and U.S. Pat. No. 4,691,036; neutral N, O, P, or S donor ligands in combination with a nickel(0) compound and an acid such as described in WO 97/02298; aminobis(imino)phosphorane nickel catalysts such as described by Fink et al. in U.S. Pat. No. 4,724,273.

Illustrative, non-limiting additional examples of various types of transition metal compounds that can be employed include the following:
2,6-bis-[1-(1-methylphenylimino)ethyl]pyridine iron[II] chloride;
2,6-bis[1-(1-ethylphenylimino)ethyl]pyridine iron[II] chloride;
2,6-bis[1-(1-isopropylphenylimino)ethyl]pyridine iron[II] chloride;
2,6-bis-(1-(2-methylphenylimino)ethyl]pyridine iron(II) chloride;
N,N'-di(trimethylsilyl)benzamidinato copper(II);
tridentate Schiff base complexes of cobalt and iron described by Mashima in *Shokubai* 1999, vol. 41, p. 58;
nickel compounds of the type described in U.S. Pat. No. 5,880,323;
nickel(II) acetylacetonate;
bis(acetonitrile)dichloro palladium(II);
bis(acetonitrile)bis(tetrafluoroborate)palladium(II);
(2,2'-bipyridine)dichloro palladium(II);
bis(cyclooctadienyl)nickel(0);
palladium(II) acetylacetonate;
bis(salicylaldiminato) complexes of the type described by Matsui et. al. in *Chemistry Letters* 2000, pp. 554-555;
cobalt dioctoate;
cobaltocene;
(cyclopentadienyl)(triphenylphosphino)cobalt(II) diiodide; and
nickel compounds of the type described in JP 09-272709.

Preferred transition metal compounds which can be used in forming the catalysts of this invention are transition metal compounds which can be represented by the formula:

$$MX_nY_m$$

where M is a transition metal of Group 4 to 8 including the lanthanide series and actinide series, and preferably of Group 4 to 6, of the Periodic Table, and Y is, independently, a halide or pseudohalide, n is the valence of M, and m is an integer of from 0 to n-1. Of the pseudohalides, preferred are alkoxide or oxyhalide groups. Pseudohalides, which is a term of art, refers to anfluoro moieties which as salt-like anions which are non-halogenides. Non-limiting examples of suitable pseudohalide groups are oxyhalide groups, hydrocarbyloxy groups (—OR groups such as alkoxy, aryloxy, cycloalkoxy, arylalkoxy, etc.), amido groups (—NR$_2$), hydrocarbylthio groups (—SR groups), and the like. Most preferred are compounds of the above formula wherein M is a Group 4 metal. Non-limiting examples of suitable transition metal compounds include, for example, transition metal halides and oxyhalides such as titanium dibromide, titanium tribromide, titanium tetrabromide, titanium dichloride, titanium trichloride, titanium tetrachloride, titanium trifluoride, titanium tetrafluoride, titanium diiodide, titanium tetraiodide, zirconium dibromide, zirconium tribromide, zirconium tetrabromide, zirconium dichloride, zirconium trichloride, zirconium tetrachloride, zirconium tetrafluoride, zirconium tetraiodide, hafnium tetrafluoride, hafnium tetrachloride, hafnium tetrabromide, hafnium tetraiodide, hafnium trichloride, hafnium tribromide, hafnium triiodide, hafnium oxychloride, vanadium dichloride, vanadium trichloride, vanadium tetrachloride, vanadium trifluoride, vanadium tetrafluoride, vanadium pentafluoride, vanadium triiodide, vanadium oxytrichloride, vanadium oxytribromide, niobium pentabromide, niobium pentachloride, niobium pentafluoride, tantalum pentabromide, tantalum pentachloride, tantalum pentafluoride, chromous bromide, chromic bromide, chromous chloride, chromic chloride, chromous fluoride, chromic fluoride, molybdenum dibromide, molybdenum tribromide, molybdenum tetrabromide, molybdenum dichloride, molybdenum trichloride, molybdenum tetrachloride, molybdenum pentachloride, molybdenum hexafluoride, lanthanum trichloride, cerous fluoride, cerous chloride, cerous bromide, cerous iodide, ceric fluoride, uranium trichloride, uranium tetrachloride, uranium tribromide, uranium tetrabromide, thorium tetrachloride, thorium tetrabromide, and the like. Among suitable alkoxides and mixed halide/alkoxides of the transition metals are Ti(OCH$_3$)$_4$, Ti(OC$_2$H$_5$)$_4$, Ti(OC$_2$H$_5$)$_3$Cl, Ti(OC$_2$H$_5$)Cl$_3$, Ti(O-iso-C$_3$H$_7$)Cl$_3$, Ti(OC$_4$H$_9$)$_3$Cl, Ti(OC$_3$H$_7$)$_2$Cl$_2$, Ti(O-iso-C$_3$H$_7$)$_2$Cl$_2$, Ti(OC$_{17}$H$_{18}$)$_2$Br$_2$, Zr(OC$_2$H$_5$)$_4$, Zr(OC$_4$H$_9$)$_4$, Zr(OC$_5$H$_{11}$)$_4$, ZrCl$_3$(OC$_2$H$_5$), ZrCl(OC$_4$H$_9$)$_3$, Hf(OC$_4$H$_9$)$_4$, Hf(OC$_4$H$_9$)$_3$Cl, VO(OC$_2$H$_5$)$_3$, Cr(O-iso-C$_4$H$_9$)$_3$, Mo(OC$_2$H$_5$)$_3$, and the like. Other transition metal compounds which may be used include amides such as Ti(NMe$_2$)$_4$, Zr(NMe$_2$)$_4$, Ti(NEt$_2$)$_4$, Zr(NEt$_2$)$_4$, and Ti(NBu$_2$)$_4$; carboxylic acid salts such as titanium oxalate, cobalt acetate, chromium acetate, nickel formate, thallium oxalate, and uranyl formate. Among the more preferred transition metal compounds are the halides, oxyhalides, alkoxides, and mixed halide-alkoxides of the Group 4 to 6 metals, and more particularly of the metals of Groups 4 and 5. Among especially preferred transition metal compounds are the trivalent or tetravalent Group 4 metal halides, particularly the chlorides, and the vanadium oxyhalides, particularly vanadium oxytrichloride. The Periodic Table referred to is that appearing on page 27 of the Feb. 4, 1985 issue of *Chemical & Engineering News*.

Another type of these new catalyst compositions is a supported catalyst composition of this invention. These compositions are reaction products between (i) a catalyst compound or complex of a transition metal of Groups 3 to 10 of the Periodic Table including the lanthanide and actinide series, (ii) a haloaluminoxane of this invention, and (iii) catalyst support or carrier material. These catalyst compositions can be formed in various ways. Each method is typically conducted in the presence of an inert liquid medium which can be a liquid transition metal compound or complex, but which typically is an inert liquid diluent such as a paraffinic, cycloparaffinic or aromatic hydrocarbon. When the transition metal catalyst compound or complex is itself a liquid, the supported catalyst of this invention can be made for example by contacting or mixing the supported haloaluminoxane of this invention with the liquid transition metal catalyst compound or complex.

One method involves mixing a transition metal catalyst compound with a catalyst support and then contacting the resultant supported transition metal catalyst compound with a haloaluminoxane of this invention. This less preferred method for forming the catalyst composition comprises first contacting the transition metal catalyst compound and the catalyst support material, preferably in the presence of a solvent or diluent. The supported transition metal catalyst compound may then be mixed with the haloaluminoxane. Instead, the haloaluminoxane complex or partially halogenated aluminoxane can be formed in situ by mixing the supported transition metal catalyst compound with the aluminoxane and the halogenation agent. The order in which the aluminoxane and the halogenation agent are mixed with the supported transition metal catalyst compound is not important. It is not preferred to make the partially halogenated aluminoxane in the presence of the supported transition metal catalyst compound.

Another method involves mixing together a transition metal catalyst compound and a haloaluminoxane of this invention and then contacting the resultant mixture with a catalyst support. In this method of forming the catalyst composition, the transition metal compound and a haloaluminoxane of this invention are combined in a first step in a suitable solvent such as an aromatic solvent to produce a solution of the reaction product. In a variation of this method, the haloaluminoxane complex or partially halogenated aluminoxane can be formed in the presence of the transition metal compound. Holding times to allow for the completion of the reaction may range from about 10 seconds to about 60 minutes depending on the reaction variables. The solution produced by combining the transition metal compound and haloaluminoxane of this invention or by forming the haloaluminoxane in the presence of the transition metal compound is then contacted with the support. The method of contact may vary, but it is preferred that the support be added to the catalyst solution with vigorous stirring. Contact times may vary from about 10 seconds to about 60 minutes or longer. The solvent can then be removed, typically by applying a vacuum.

Still another method, a preferred method of forming the catalyst compositions of this invention, involves depositing the haloaluminoxane of this invention on a catalyst support and then mixing the resultant supported aluminoxane with the transition metal catalyst compound. This method comprises contacting a haloaluminoxane of this invention and catalyst support material for example as a slurry in a suitable inert diluent, prior to mixing with the transition metal catalyst compound. For the partially halogenated aluminoxanes and the haloaluminoxane complexes, the aluminoxane and the halogenation agent may be reacted prior to contact with the catalyst support material; alternatively, again for the partially halogenated aluminoxanes and the haloaluminoxane complexes, the aluminoxane may be contacted with the catalyst support material followed by the reaction of the aluminoxane and the halogenation agent. As in their respective syntheses, heat or aging is usually required to make the partially halogenated aluminoxane, and is avoided when making haloaluminoxane complexes. The resultant supported haloaluminoxane of this invention—preferably after recovery and washing with an inert solvent or diluent—is contacted with or in a solution of the transition metal compound in a suitable anhydrous inert solvent, preferably with agitation. In this way the haloaluminoxane and the transition metal compound can interact to produce an active supported catalyst composition.

Suitable solvents and/or diluents include, but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcyclopentane and the like; and aromatic and alkyl-substituted aromatic compounds such as benzene, toluene, xylene and the like. Mixtures of different types of such hydrocarbons can also be used, such as a mixture of one or more acyclic aliphatic hydrocarbons and one or more cycloaliphatic hydrocarbons; a mixture of one or more acyclic aliphatic hydrocarbons and one or more aromatic hydrocarbons; a mixture of one or more cycloaliphatic hydrocarbons and one or more aromatic hydrocarbons; or a mixture of one or more acyclic aliphatic hydrocarbons, one or more cycloaliphatic hydrocarbons, and one or more aromatic hydrocarbons.

Once all of the components for making the supported catalyst are present together, the mixture thereof may be heated. Temperatures in the range of about 20 to about 100° C. are typically used, but higher or lower temperatures can be used if desired.

In all cases, a catalytically-active catalyst composition is formed by interaction between a haloaluminoxane of this invention and one or more transition metal compounds of Groups 3 to 10 including the lanthanide series and the actinide series, and this catalyst composition is supported on the catalyst support or carrier used. The catalyst support or carrier material used in this process can be any particulate material useful as a catalyst support or carrier such as a porous spheroidal or particulate organic resinous support or a porous inorganic support, and preferably is a particulate inorganic catalyst support such as an inorganic oxide or an inorganic material comprised of one or more oxides. Various ratios of supported haloaluminoxane of this invention to the liquid transition metal catalyst compound or complex can be used. For example these components can be proportioned such that the mole ratio of aluminum to transition metal is in the range of about 20:1 to about 2000:1, and preferably in the range of about 20:1 to about 200:1.

It is preferred that the catalyst components as well as the resultant catalyst compositions be handled in an inert, moisture-free, oxygen free environment such as argon, nitrogen or helium because of the sensitivity of the catalyst components and catalyst compositions to moisture and oxygen.

Regardless of the method used in the preparation, the active supported catalyst can be recovered by evaporation of the solvent to obtain a free-flowing solid or alternatively, the active supported catalyst can be maintained in its slurry state for direct use. Another variant is to replace the original solvent/diluent with another inert liquid diluent such as a paraffinic hydrocarbon to thereby provide a slurry of active catalyst for use in the polymerization.

Modified supported catalysts of this invention can be prepared by combining in any order at least one transition metal compound, at least one haloaluminoxane of this invention, at least one modifier, and the support in one or more suitable solvents or diluents. A modifier may be defined as a compound containing a Lewis acid or basic functionality, such as, for example, tetraethoxysilane, phenyltri(ethoxy)silane, bis-tert-butylhydroxytoluene (BHT), N,N-dimethylaniline and the like. Suitable solvents and/or diluents are the same as those described above. It is preferred that these catalyst components be handled in an inert, moisture-free, oxygen-free environment such as argon, nitrogen or helium because of the sensitivity of the catalyst components to moisture and oxygen.

In one method of forming a modified supported catalyst, the haloaluminoxane of this invention and the modifier are combined in a first step in a suitable solvent such as an aromatic solvent to produce a solution or slurry. The transition metal compound is then added to this solution. When the haloaluminoxane is a partially halogenated aluminoxane, these combined steps may be carried out in the temperature range of about −100 to about 300° C., and preferably in the range of about 0 to about 100° C. Holding times to allow for the completion of the reaction may range from about 10 seconds to about 60 minutes depending on the reaction variables. The solution produced by combining the transition metal compound, the haloaluminoxane of this invention, and the modifier can then be contacted with the support, or preferably the haloaluminoxane of this invention is in the presence of the support as formed and thus is supported on the inorganic catalyst support ab initio. This supported haloaluminoxane of this invention is then treated with the modifier and then with the transition metal compound in a suitable inert organic medium such as an aromatic solvent to produce a slurry of active modified catalyst of this invention. For the partially halogenated aluminoxanes, in these operations contact temperatures may range from about 0 to about 100° C. depending upon the solvents used. Contact times may vary from about 10 seconds to about 60 minutes or longer.

Regardless of the method used in forming the modified catalyst, the solvent or diluent can be removed, typically by applying a vacuum, in order to isolate the catalyst. The solution may or may not be heated in order to aid in the removal of the solvent. Alternatively the active catalyst slurry, with some of the solvent/diluent stripped away if desired, can be used as a component in conducting the polymerization. Another variant is to replace the original solvent/diluent with another inert liquid diluent such as a paraffinic hydrocarbon to thereby provide a slurry of active catalyst for use in the polymerization.

In accordance with this invention, optimum results are generally obtained wherein the molar ratio of haloaluminoxane of this invention to transition metal compound is from about 1.1 to about 20,000:1, preferably from about 10:1 to about 1000:1, and the molar ratio of haloaluminoxane of this invention to modifier is from about 1:1 to about 20,000:1, preferably from about 10:1 to about 1000:1. The concentration of transition metal compound on the support is typically between 0.01 wt % to about 100 wt %, preferably about 0.1 wt % to about 20 wt % based upon the weight of the support.

The supported catalyst systems of this invention are useful in producing olefin polymers and especially ethylene polymers, propylene polymers, ethylene/α-olefin copolymers, styrene polymers and copolymers and the like.

In conducting the polymerizations pursuant to this invention, the catalyst components can be used in solution or deposited on a solid support. When used in solution polymerization, the solvent can be, where applicable, a large excess quantity of the liquid olefinic monomer. Typically, however, an ancillary inert solvent, typically a liquid paraffinic or aromatic hydrocarbon solvent is used, such as heptane, isooctane, decane, toluene, xylene, ethylbenzene, mesitylene, or mixtures of liquid paraffinic hydrocarbons and/or liquid aromatic hydrocarbons.

Polymers can be produced pursuant to this invention by homopolymerization of olefins, typically 1-olefins (also known as α-olefins) such as ethylene, propylene, 1-butene, styrene, or copolymerization of two or more copolymerizable monomers, at least one of which is typically a 1-olefin. The other monomer(s) used in forming such copolymers can be one or more different 1-olefins and/or a diolefin, and/or a acetylenic monomer. Olefins that can be polymerized in the presence of the catalyst compositions of this invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Normally, the hydrocarbon monomers used, such as 1-olefins, diolefins and/or acetylene monomers, will contain up to about 10 carbon atoms per molecule. Preferred 1-olefin monomers for use in the process include ethylene, propylene, 1-butene, 3-methyl-1-butene, 4-methyl-1-pentene, 1-hexene, and 1-octene. It is particularly preferred to use supported or unsupported catalysts of this invention in the polymerization of ethylene, or propylene, or ethylene and at least one $C_3$-$C_8$ 1-olefin copolymerizable with ethylene. Typical diolefin monomers which can be used to form terpolymers with ethylene and propylene include butadiene, hexadiene, norbornadiene, and similar copolymerizable diene hydrocarbons. 1-Heptyne and 1-octyne are illustrative of suitable acetylenic monomers which can be used.

Often the monomer used is a 1-alkene monomer whereby a homopolymer is prepared. In other frequent cases a mixture of a 1-alkene monomer such as ethylene and at least one monomer copolymerizable therewith is used whereby a copolymer is produced.

Polymerization of ethylene or copolymerization with ethylene and an α-olefin having 3 to 10 carbon atoms may be performed in either the gas or liquid phase (e.g., in a solvent, such as toluene, or heptane). The polymerization can be conducted at conventional temperatures (e.g., 0° to 120° C.) and pressures (e.g., ambient to 50 kg/cm$^2$) using conventional procedures as to molecular weight regulations and the like.

The heterogeneous catalysts of this invention can be used in polymerizations conducted as slurry processes or as gas phase processes. By "slurry" in this connection is meant that the particulate catalyst is used as a slurry or dispersion in a suitable liquid reaction medium which may be composed of one or more ancillary solvents (e.g., liquid aliphatic or aromatic hydrocarbons, etc.) or an excess amount of liquid monomer to be polymerized in bulk. Generally speaking, these polymerizations are conducted at one or more temperatures in the range of about 0 to about 160° C. and under atmospheric, subatmospheric, or superatmospheric conditions. Preferably polymerizations conducted in a liquid reaction medium containing a slurry or dispersion of a catalyst of this invention are conducted at temperatures in the range of about 40 to about 110° C. Typical liquid diluents for such processes include isobutane, pentane, isopentane, hexane, heptane, toluene, and like materials. Typically, when conducting gas phase polymerizations, superatmospheric pressures are used, and the reactions are conducted at temperatures in the range of about 50 to about 160° C. These gas phase polymerizations can be performed in a stirred or fluidized bed of catalyst in a pressure vessel adapted to permit the separation of product particles from unreacted gases. Thermostated ethylene, comonomer, hydrogen and an inert diluent gas such as nitrogen can be introduced or recirculated to maintain the particles at the desired polymerization reaction temperature. An aluminum alkyl such as triethylaluminum may be added as a scavenger of water, oxygen and other impurities. In such cases the aluminum alkyl is preferably employed as a solution in a suitable dry liquid hydrocarbon solvent such as toluene or xylene. Concentrations of such solutions in the range of about $5 \times 10^{-5}$ molar are conveniently used. But solutions of greater or lesser concentrations can be used, if desired. Polymer product can be withdrawn continuously or semi-continuously at a rate that maintains a constant product inventory in the reactor.

In general, the polymerizations and copolymerizations conducted pursuant to this invention are carried out using a catalytically effective amount of a novel catalyst composition of this invention, which amount may be varied depending upon such factors such as the type of polymerization being conducted, the polymerization conditions being used, and the type of reaction equipment in which the polymerization is being conducted. In many cases, the amount of the catalyst of this invention used will be such as to provide in the range of about 0.000001 to about 0.01 percent by weight of transition, lanthanide, or actinide metal based on the weight of the monomer(s) being polymerized.

After polymerization and deactivation of the catalyst in a conventional manner, the product polymer can be recovered from the polymerization reactor by any suitable means. When conducting the process with a slurry or dispersion of the catalyst in a liquid medium the product typically is recovered by a physical separation technique (e.g., decantation, etc.). The recovered polymer is usually washed with one or more suitably volatile solvents to remove residual polymerization solvent or other impurities, and then dried, typically under reduced pressure with or without addition of heat. When conducting the process as a gas phase polymerization, the product after removal from the gas phase reactor is typically freed of residual monomer by means of a nitrogen purge, and may possibly be used without further catalyst deactivation or catalyst removal.

When preparing polymers pursuant to this invention conditions may be used for preparing unimodal or multimodal polymer types. For example, mixtures of catalysts of this invention formed from two or more different metallocenes having different propagation and termination rate constants for ethylene polymerizations can be used in preparing polymers having broad molecular weight distributions of the multimodal type.

The foregoing operations described herein are conducted under conventional inert atmospheres using suitably anhydrous materials.

The following examples are presented for purposes of illustration, and are not intended to impose limitations on the scope of this invention. All experiments of these Examples were carried out under inert atmosphere conditions, using Schlenk glassware and vacuum line, in conjunction with a nitrogen drybox. Solvents were dried using standard methods. Filtration and vacuum distillation were done inside the nitrogen drybox and distillates collected in a trap at −78° C. The samples for $^{19}$F NMR analysis were either in THF-d8 or in toluene-d8, each typically containing 0.05-0.4 wt % fluorine. Aluminoxanes were obtained from stock solutions manufactured by Albemarle Corporation.

In the Examples, methylaluminoxane is sometimes abbreviated as MAO; the product of a reaction between MAO and a halohydrocarbon containing fluorine is sometimes abbreviated as F-MAO. Similarly, the product of a reaction between MAO and a halohydrocarbon containing chlorine is sometimes abbreviated as CL-MAO, and a product of a reaction between MAO and a halohydrocarbon containing bromine is sometimes abbreviated as Br-MAO. The product of a reaction between MAO and either a fluorosilicone (fluorosiloxane) or a polyfluorosilicone (polyfluorosiloxane) is sometimes abbreviated as FSi-MAO. TMA is an abbreviation for trimethylaluminum; PE is sometimes used as an abbreviation for polyethylene.

EXAMPLE 1

Synthesis of a Fluoroaluminoxane Complex and F-MAO from Neat MAO

In the drybox, solid MAO (0.20 g) was dissolved in $C_6D_6$ (0.80 g) in a 4 mL vial and $C_6H_5CF_3$ (0.0120 g) was mixed with 0.80 g $C_6D_6$ in another vial. The $C_6H_5CF_3$ (0.20 g; based on 2 mol % F on Al) in $C_6D_6$ was dropwise added to the MAO $C_6D_6$ solution with vigorous shaking. The colorless solution changed to brown, then quickly changed to deep blue. The blue material was transferred to an NMR tube for NMR analysis. The NMR tube was then placed in an 86° C. oil bath for 1 min. The blue-colored substance in the NMR tube became colorless. THF-d8 was added for better resolution. No new species formed after heat treatment except with THF-d8 giving sharpened peaks of Al-Me species and better resolution. Some chemical shifts also changed due to the addition of THF-d8 in $C_6D_6$ solution. $^1$H NMR (THF-d8, 25° C., 400 MHz): δ −0.5 ppm (broad, C$\underline{H}_3$ of MAO); δ −0.8 ppm (s, Al(C$\underline{H}_3$)$_3$); δ 1.4 ppm (s, $C_6H_5$C(C$\underline{H}_3$)$_3$); δ 1.7-1.8 ppm (multi-singlet, p-, m-, and o-$CH_3C_6H_4$C(C$\underline{H}_3$)$_2C_6H_5$); δ 2.3 ppm (s, C$\underline{H}_3C_6H_5$); δ 7.0-7.5 ppm (m, $CH_3C_6\underline{H}_5$, $C_6\underline{H}_5$C(CH$_3$)$_3$) p-, m- and o-$CH_3C_6\underline{H}_4$C(CH$_3$)$_2C_6\underline{H}_5$). $^{19}$F NMR (THF-d8, 25° C., 400 MHz): δ −140 ppm (broad, F—Al of F-MAO). The side products of the reaction were $C_6H_5C(CH_3)_3$, p-, m-, and o-$CH_3C_6H_4C(CH_3)_2C_6H_5$.

EXAMPLE 2

Synthesis of F-MAO with 0.5 Mol % F Relative to Aluminum $C_6H_5CF_3$ was degassed with $N_2$ for 30 min before it was taken into the drybox. In the drybox with $N_2$ atmosphere, a 20 mL vial was charged with $C_6H_5CF_3$ (0.46 g) and toluene (10.02 g) to make a 4.4 wt % stock solution of $C_6H_5CF_3$. MAO (30% in toluene; 20.3 g) was placed in an 4 oz reaction bottle. Some of the $C_6H_5CF_3$ stock solution (0.493 g) was added dropwise to the vigorously stirring MAO solution. The resultant deep blue slurry was heated to 84° C. and stirred for 9 min, resulting in an almost colorless, clear solution. Yield: 19.75 g. $^1$H NMR (THF-d8, 25° C., 400 MHz): δ −0.5 ppm (broad, C$\underline{H}_3$ of MAO); δ −0.8 ppm (s, Al(C$\underline{H}_3$)$_3$); δ 1.4 ppm (s, $C_6H_5$C(C$\underline{H}_3$)$_3$); δ 1.7-1.8 ppm (multi-singlet, p-, m-, and o-$CH_3C_6H_4$C(C$\underline{H}_3$)$_2C_6H_5$); δ 2.3 ppm (s, C$\underline{H}_3C_6H_5$); δ 7.0-7.5 ppm (m, $CH_3C_6\underline{H}_5$, $C_6\underline{H}_5$C(CH$_3$)$_3$), p-, m-, and o-$CH_3C_6\underline{H}_4$C(CH$_3$)$_2C_6\underline{H}_5$). $^{19}$F NMR (THF-d8, 25° C., 400 MHz): δ −140 ppm (broad, F—Al of F-MAO). The side products of the reaction were $C_6H_5C(CH_3)_3$, p-, m-, and o-$CH_3C_6H_4C(CH_3)_2C_6H_5$.

EXAMPLE 3

Synthesis of F-AMO with 2 Mol % F Relative to Aluminum

In the drybox with $N_2$ atmosphere, MAO (30% in toluene; 20.0 g) was placed in an 4 oz reaction bottle. Some of the $C_6H_5CF_3$ stock solution made in Example 2 (2.0 g) was added dropwise to the vigorously stirring MAO solution. The resultant deep blue slurry was stirred for 20 min then heated to 84° C. and stirred for 10 mins, resulting in an almost colorless, clear solution. Yield: 21.3 g. $^1$H NMR (THF-d8, 25° C., 400 MHz): δ −0.5 ppm (broad, C$\underline{H}_3$ of MAO); δ −0.8 ppm (s, Al(C$\underline{H}_3$)$_3$); δ 1.4 ppm (s, $C_6H_5$C(C$\underline{H}_3$)$_3$); δ 1.7-1.8 ppm (multi-singlet, p-, m-, and o-$CH_3C_6H_4$C(C$\underline{H}_3$)$_2C_6H_5$); δ 2.3 ppm (s, C$\underline{H}_3C_6H_5$); δ 7.0-7.5 ppm (m, $CH_3C_6\underline{H}_5$, $C_6\underline{H}_5$C(CH$_3$)$_3$),p-, m-, and o-$CH_3C\underline{H}_6\underline{H}_4$C(CH$_3$)$_2C_6H_5$). $^{19}$F NMR (THF-d8, 25° C., 400 MHz): δ −140 ppm (broad, F—Al of F-MAO). The side products of the reaction were $C_6H_5C(CH_3)_3$, p-, m-, and o-$CH_3C_6H_4C(CH_3)_2C_6H_5$, and this was confirmed by GC-MS.

EXAMPLE 4

Synthesis of F-MAO with 4 Mol % F Relative to Aluminum

In the drybox with $N_2$ atmosphere, MAO (30% in toluene; 20.0 g) was placed in an 4 oz reaction bottle. Some of the $C_6H_5CF_3$ stock solution made in Example 2 (4.1 g) was added dropwise to the vigorously stirring MAO solution. The resultant deep blue slurry was stirred for 28 min then heated to 84° C. and stirred for 9 mins, resulting in a light yellow, clear solution. Yield: 22.9 g. $^1$H NMR (THF-d8, 25° C., 400 MHz): δ −0.5 ppm (broad, C$\underline{H}_3$ of MAO); δ −0.8 ppm (s, Al(C$\underline{H}_3$)$_3$); δ 1.4 ppm (s, $C_6H_5$C(C$\underline{H}_3$)$_3$); δ 1.7-1.8 ppm (multi-singlet, p-, m-, and o-$CH_3C_6H_4$C(C$\underline{H}_3$)$_2C_6H_5$); δ 2.3 ppm (s, C$\underline{H}_3C_6H_5$); δ 7.0-7.5 ppm (m, $CH_3C_6\underline{H}_5$, $C_6\underline{H}_5$C(CH$_3$)$_3$), p-, m-, and o-$CH_3C_6\underline{H}_4$C(CH$_3$)$_2C_6\underline{H}_5$). $^{19}$F NMR (THF-d8, 25° C., 400 MHz): δ −140 ppm (broad, F—Al of F-MAO). The side products of the reaction were $C_6H_5C(CH_3)_3$, p-, m-, and o-$CH_3C_6H_4C(CH_3)_2C_6H_5$.

EXAMPLE 5

Synthesis of F-MAO with 6 Mol % F Relative to Aluminum

In the drybox with $N_2$ atmosphere, MAO (30% in toluene; 30.0 g) was placed in an 8 oz reaction bottle. A $C_6H_5CF_3$ toluene solution (4.44 g; 10%; 1.76 g $C_6H_5CF_3$+15.84 g toluene) was added dropwise to the vigorously stirring MAO solution. The resultant deep blue slurry was stirred for 20 min then heated to 84° C. and stirred for 20 mins, resulting in a light green, clear solution. Yield: 33.3 g. $^1$H NMR (THF-d8, 25° C. 400 MHz): δ −0.5 ppm (broad, C$\underline{H}_3$ of MAO); δ −0.8 ppm (s, Al(C$\underline{H}_3$)$_3$); δ 1.4 ppm (s, $C_6H_5$C(C$\underline{H}_3$)$_3$); δ 1.7-1.8 ppm (multi-singlet, p-, m-, and o-$CH_3C_6H_4$C(C$\underline{H}_3$)$_2C_6H_5$); δ 2.3 ppm (s, C$\underline{H}_3C_6H_5$); δ 7.0-7.5 ppm (m, $CH_3C_6\underline{H}_5$, $C_6\underline{H}_5$C(CH$_3$)$_3$), p-, m-, and o-$CH_3C_6\underline{H}_4$C(CH$_3$)$_2C_6\underline{H}_5$). $^{19}$F NMR(THF-d8, 25° C., 400 MHz): δ −140 ppm (broad, F—Al of F-MAO). The side products of the reaction were $C_6H_5C(CH_3)_3$, and p-, m-, and o-$CH_3C_6H_4C(CH_3)_2C_6H_5$.

EXAMPLE 6

Synthesis of a Fluoroaluminoxane Complex and F-MAO with 12 Mol % F Relative to Al In the drybox with $N_2$ atmosphere, MAO (30% in toluene; 30.1 g) was placed in an 8 oz reaction bottle. A toluene solution of $C_6H_5CF_3$ (4.6%; 0.925 g $C_6H_5CF_3$+18.0 g toluene) was added dropwise to the vigorously stirring MAO solution through a dropping funnel. The resultant deep blue slurry was divided in two portions: 29.0 g was set aside; the rest was stirred for 20 min then heated to 84° C. and stirred for 30 mins, resulting in a light green, clear solution with colorless solid material at the bottom. NMR analysis for the solution phase showed similar $F^{19}$ and $H^1$ spectra to those containing 0.5-6-mol % F relative to aluminum. The fluorine content in solution phase was much lower than 12 mol % F charge, i.e., the 29.0 g F-MAO slurry (without heat treatment) for supported catalyst preparation contained only 10.5 mol % F and the solution from the rest of the F-MAO after heat treatment contained only 8.1 mol % F. The side products of the reaction were $C_6H_5C(CH_3)_3$, and p-, m-, and o-$CH_3C_6H_4C(CH_3)_2C_6H_5$, and this was confirmed by GC-MS.

EXAMPLE 7

Supporting of a Fluoroaluminoxane Complex with 2 Mol % F Relative to Al on Silica In the drybox with $N_2$ atmosphere, MAO (30% in toluene; 3.2 g) was placed in a 20 mL vial with a magnetic stirring bar. Silica (2.2 g) was added at once to the vigorously stirring MAO solution. Then a toluene solution of $C_6H_5CF_3$ (0.050 g $C_6H_5CF_3$ in 3.0 g toluene) was added dropwise to the vigorously stirring MAO/silica slurry. The resultant deep blue slurry was allowed to stir for 15 min. The slurry was then filtered through a coarse frit. The filtrate was colorless and clear. The deep blue solids were dried under vacuum for one hour. The deep blue color changed to purple blue. Yield: 3.2 g.

EXAMPLE 8

Supporting of a Fluoroaluminoxane Complex with 2 Mol % F Relative to Al on Silica In the drybox, the oven dried 300 mL flask, condenser, overhead stirrer and septum were assembled. 30.0 g MAO (30% in toluene) was weighed into a 4 oz reaction bottle with a magnetic stirring bar. $C_6H_5CF_3$ (0.147 g in 3.1 g toluene) was then dropwise added to the vigorously stirring MAO solution. Some of this blue slurry material (19.0 g) was weighed into a beaker and transferred to the 300 mL flask. The beaker was washed with 35 g toluene, which was added to the deep blue slurry. While the overhead stirrer was turned on, 10.0 g silica was added at once and the resultant slurry was allowed to stir at room temperature for 60 min. The mixture still retained a deep blue color.

EXAMPLE 9

Supporting of a Fluoroaluminoxane Complex with 6 Mol % F Relative to Al on Silica In the drybox, the oven dried 300 mL flask, condenser, overhead stirrer and septum were assembled. 30.0 g MAO (30% in toluene) was weighed into a 4 oz reaction bottle with a magnetic stirring bar. $C_6H_5CF_3$ solution (0.441 g in 9.2 g toluene) was then dropwise added to the vigorously stirring MAO solution. Some of this blue slurry material (19.0 g) was weighed into a beaker and transferred to the 300 mL flask. The beaker was washed with 40 g toluene, which was added to the deep blue slurry. While the overhead stirrer was turned on, 10.0 g silica was added at once and the resultant slurry was allowed to stir at room temperature for 60 min. The mixture still retained a deep blue color.

EXAMPLE 10

Supporting of a Fluoroaluminoxane Complex with 12 Mol % F Relative to Al on Silica In the drybox, the oven dried 300 mL flask, condenser, overhead stirrer and septum were assembled and placed in an oil bath. This experiment used the fluoroaluminoxane complex from Example 6. Because significant precipitate formed, the blue solution phase was sampled for NMR analysis to quantify the F content. Quantitative $F^{19}$ NMR analysis showed only 10.5 mol % F relative to Al. The blue slurry (29.0 g) was weighed into a beaker and transferred to the flask. The beaker was washed with 40 g toluene, which was added to the deep blue slurry. While the overhead stirrer was turned on, 10.0 g silica was added at once and the resultant slurry was allowed to stir at room temperature for 60 min. The mixture still retained its deep blue color.

EXAMPLE 11

Supporting of F-MAO with 2 Mol % and 4 Mol % F Relative to Al on Silica

In the drybox, the oven dried 300 mL flask, condenser, overhead stirrer and septum were assembled and placed in an oil bath. F-MAO with 2 mol % F relative to aluminum (30% in toluene; 18.0 g) made according to Example 3 was weighed into a beaker then transferred to the 300 mL flask. The beaker was washed with 45 g toluene, which was added to the F-MAO solution. While the overhead stirrer was turned on, 10.0 g silica was added at once and the resultant slurry was allowed to stir at room temperature for 60 min.

The same procedure was followed, using F-MAO with 4 mol % F relative to aluminum (30% in toluene; 20.5 g) made according to Example 4. The amount of wash toluene was 32 g, and 10.2 g of silica were used.

EXAMPLE 12

Supporting of F-MAO with 6 Mol % F Relative to Al on Silica

In the drybox, the oven dried 300 mL flask, condenser, overhead stirrer and septum were assembled and placed in an oil bath. MAO (30% in toluene; 18.5 g) was weighed into a beaker then transferred to the 300 mL flask. The beaker was washed with 40 g toluene, which was added to the MAO solution. While the overhead stirrer was turned on, $C_6H_5CF_3$ (0.288 g, in 3 g toluene) was slowly added to the MAO solution with a glass pipette. Then the blue mixture was heated to 80° C. for 30 min. The resultant solution was light green. The solution was allowed to cool to below 50° C. Then 10.0 g silica was added at once and the resultant slurry was allowed to stir at room temperature for 60 min.

EXAMPLE 13

Stability Tests of F-MAO

The stability of some fluoroaluminoxanes prepared according to the methods described in Examples 2-6 were tested and compared to a regular MAO sample. Results are summarized in Table 1. All samples were stored in carbon steel containers. Indoor conditions were about 25° C. in the drybox; outdoor conditions were between approximately 20 and 50° C. (typical Southern U.S. summer weather) in a metal cabinet. The MAO content of all solutions was 30% when reacted with $CF_3C_6H_5$. For comparison, note that fresh (non-fluorinated) MAO has a gel content of 1.5 wt %. The fluorine content in Table 1 is mole percent relative to aluminum.

TABLE 1

| Substance | F content | Day 18, indoor Gel content | Day 30, outdoor Gel content | Day 60, outdoor Gel content | Day 75, outdoor Gel content | Day 110, outdoor Gel content |
| --- | --- | --- | --- | --- | --- | --- |
| MAO | 0.0 mol % | 13.7 wt % | solidified | — | — | — |
| F-MAO | 2.0 mol % | 1.3 wt % | 4.4 wt % | 11.0 wt % | 22.9 wt % | — |
| F-MAO | 4.0 mol % | 0.9 wt % | 0.8 wt % | 1.5 wt % | 1.9 wt % | 1.6 wt % |

EXAMPLE 14

Stability Test of MAO Toluene Solution with $C_6H_5C(CH_3)_3$ and p-, m-, o-$CH_3C_6H_4C(CH_3)_2C_6H_5$ To verify whether the side products $C_6H_5C(CH_3)_3$ and p-, m-, o-$CH_3C_6H_4C(CH_3)_2C_6H_5$ also play roles in the MAO gel reduction, a MAO 30% toluene solution was mixed with the F-MAO side products $C_6H_5C(CH_3)_3$ and p-, m-, o-$CH_3C_6H_4C(CH_3)_2C_6H_5$ from the reaction of MAO with $(CF_3)C_6H_5$.

$(CF_3)C_6H_5$ (27.3 g) in toluene (26.2 g) was added dropwise to a vigorously stirring MAO solution (30 wt %, 124.5 g) in toluene. The resulting slurry was filtered. The filtrate containing $C_6H_5C(CH_3)_3$ and p-, m-, o-$CH_3C_6H_4C(CH_3)_2C_6H_5$ was treated with silica (12 g) for 30 min. $^1H$ NMR showed about 0.2 wt % F-MAO/MAO. More silica (4 g) was added. After stirring for 15 minutes, $^1H$ NMR showed no detectable F-MAO/MAO. The silica-treated filtrate (5 g) was added to the MAO solution (11 g), concentrated from 16 g MAO 30% solution to make a 30% MAO solution containing the amount of $C_6H_5C(CH_3)_3$ and p-, m-, o-$CH_3C_6H_4C(CH_3)_2C_6H_5$ similar to the amount present in a F-MAO solution with 2 mol % F per Al from the reaction of MAO with $(CF_3)C_6H_5$. This MAO solution formed gel after a week and completely solidified after a month, similar to a regular 30% MAO toluene solution

EXAMPLE 15

NMR Scale Synthesis of F-MAO from hexafluoro-p-xylene and from hexafluoro-m-xylene In the drybox, solid MAO (0.10 g) was dissolved in $C_6D_6$ (0.5 mL) in a 4 mL vial. To this MAO solution was dropwise added hexafluoroparaxylene (p-$(CF_3)_2C_6H_4$, 0.012 g). The resultant deep blue slurry was shaken well. Then small portion of this blue slurry was transferred to another 4 mL vial containing few drops of THF-d8. The deep blue color immediately disappeared. All solids dissolved, resulting in a light yellow solution. Major $^1H$ NMR peaks (THF-d8, 25° C., 400 MHz): δ −0.5 (broad, MAO); δ −0.8 (s, Al(C$\underline{H}_3$)$_3$); δ 2.3 (s, C$\underline{H}_3$C$_6$H$_5$); δ 7.2-7.5 (m, aromatic protons). $^{19}F$ NMR (THF-d8, 25° C., 400 MHz): δ −140 (broad, $\underline{F}$—Al of F-MAO). The side products have not been completely identified. The same procedure was followed to prepare F-MAO from the reaction of MAO (30% in toluene, 0.20 g) with hexafluorometaxylene (m-$(CF_3)_2C_6H_4$, 0.012 g). $^1H$ NMR peaks for major components were the same as with hexafluoroparaxylene. The side products have not been completely identified. $^{19}F$ NMR showed −140 ppm broad peak ($\underline{F}$—Al of F-MAO) as the sole fluorinated species.

EXAMPLE 16

Synthesis of F-MAO from 4-methyl-α,α,α-trifluorotoluene (MTFT)

In the drybox, a 4 mL vial was charged with MTFT p-$(CF_3)(CH_3)C_6H_4$, 0.016 g) and toluene (0.16 g). MAO (30% in toluene; 1.5 g) was placed in a 20 mL vial with a magnetic stirring bar. The MTFT solution was then dropwise added to the vigorously stirring MAO solution. Next, the resulting deep blue slurry was heated in an 84° C. oil bath for 12 min to obtain an almost colorless, clear solution. Yield: 1.5 g. $^1H$ NMR (THF-d8, 25° C., 400 MHz): δ −0.5 (broad, MAO); δ −0.8 (s, Al(C$\underline{H}_3$)$_3$); δ 1.4 (s, 4-CH$_3$C$_6$H$_4$C(C$\underline{H}_3$)$_3$); δ 1.7-1.9 (multi-singlet, (4-CH$_3$C$_6$H$_4$)$_2$C(C$\underline{H}_3$)$_2$ and isomers); δ 2.2 (multi-singlet, (4-C$\underline{H}_3$C$_6$H$_4$)$_2$C(CH$_3$)$_2$ and isomers); δ 2.3 (s, C$\underline{H}_3$C$_6$H$_5$); δ 7.0-7.7 (m, aromatic protons). $^{19}F$ NMR (THF-d8, 25° C., 400 MHz): δ −140 (broad, $\underline{F}$—Al of F-MAO). The major side product of the reaction was 4-CH$_3$C$_6$H$_4$C(CH$_3$)$_3$.

EXAMPLE 17

Synthesis of F-MAO from $(C_6H_5)_3$SiF

In the drybox, a 4 mL vial was charged with triphenylsilyl fluoride (0.012 g) and MAO (30% in toluene, 0.2 g) and shaken well, resulting in a colorless, clear solution. Yield: 0.212 g. H1 NMR (THF-d8, 25° C., 400 MHz): δ −0.5 (broad, MAO); δ −0.8 (s, Al(C$\underline{H}_3$)$_3$); δ 0.8 (s, $(C_6H_5)_3$SiC$\underline{H}_3$); δ 2.3 (s, C$\underline{H}_3$C$_6$H$_5$); δ 7.2-7.5 (m, CH$_3$C$_6$H$_5$, and $(C_6\underline{H}_5)_3$SiCH$_3$). F$^{19}$ NMR (THF-d8, 25° C., 400 MHz): δ −140 (broad, 1F, —Al(F)—O—). The side product of the reaction was $(C_6H_5)_3$SiCH$_3$.

EXAMPLE 18

Synthesis of F-MAO from Octafluorotoluene

In the drybox, a 4 mL vial was charged with MAO (30% in toluene; 0.2 g). To this MAO solution was dropwise added octafluorotoluene (0.012 g). The mixture was shaken well, resulting in a pink solution with small amount of crystal-like solids. The pink color became more intense with time. A small amount of this pink slurry was added to THF-d8 in a 4 mL vial. The pink color faded immediately, resulting in a colorless solution. The rest of the pink slurry changed to colorless solution as well after one hour. Major $^1H$ NMR peaks (THF-d8, 25° C., 400 MHz): δ −0.5 (broad, MAO); δ −0.8 (s, Al(C$\underline{H}_3$)$_3$); δ 2.3 (s, C$\underline{H}_3$C$_6$H$_5$); δ 7.2-7.5 (m, aromatic protons). $^{19}F$ NMR (THF-d8, 25° C., 400 MHz): δ −140 (broad, $\underline{F}$—Al of F-MAO). The side products have not been completely identified.

EXAMPLE 19

Synthesis of Cl-MAO from α,α,α-trichlorotoluene

In the drybox, a 20 mL vial was charged with 14 g MAO (30% in toluene) and $C_6H_5CCl_3$ (0.185 g) and shaken well, resulting in a deep blue slurry. The blue color faded completely overnight. Yield: 14.2 g. $^1$H NMR (THF-d8, 25°, 400 MHz): δ −0.5 (broad, MAO); δ −0.8 (s, TMA); δ 1.4 (s, $C_6H_5C(CH_3)_3$); δ 1.8 (s, 4-$CH_3C_6H_4C(CH_3)_2C_6H_5$); δ 2.2 (s, 4-$CH_3C_6H_4C(CH_3)_2C_6H_5$); δ 2.3 (s, $CH_3C_6H_5$); δ 7.0-7.7 (m, aromatic protons). The major side products of the reaction were $C_6H_5C(CH_3)_3$ and p-, m-, and o-$CH_3C_6H_4C(CH_3)_2C_6H_5$.

EXAMPLE 20

Synthesis of Cl-MAO from Benzylchloride

In the drybox, ¼ pipette of MAO (30% in toluene) was placed in a 4 mL vial. One drop of $C_6H_5CH_2Cl$ was added to the MAO solution. The exothermic reaction took place at once, resulting in a red-orange slurry. The color faded very fast. After about 5 min, the color slurry became an almost colorless solution. $^1$H NMR (THF-d8, 25°, 400 MHz): δ −0.5 (broad, MAO); δ −0.8 (s, TMA); δ 2.2-2.3 (multi-singlet, p-, m-, and o-$CH_3C_6H_4CH_2C_6H_5$); δ 2.3 (s, $CH_3C_6H_5$); δ 3.8 (m, p-, m-, and o-$CH_3C_6H_4CH_2C_6H_5$, $C_6H_5CH_2C_6H_5$); δ 7.0-7.7 (m, aromatic protons). The side products of the reaction p-, m-, and o-$CH_3C_6H_4CH_2C_6H_5$ and $C_6H_5CH_2C_6H_5$ were confirmed by GC-MS.

EXAMPLE 21

Synthesis of Br-MAO from Benzylbromide

In the drybox, MAO (30% in toluene, 0.4 g) was placed in a 4 mL vial. One drop of $C_6H_5CH_2Br$ was added to the MAO solution. The exothermic reaction took place at once, resulting a red-orange slurry. The color faded very fast. After about 5 min, the color slurry became a light brown solution. $^1$H NMR (THF-d8, 25°, 400 MHz): δ −0.5 (broad, MAO); δ −0.8 (s, TMA); δ 2.2-2.3 (multi-singlet, p-, m-, and o-$CH_3C_6H_4CH_2C_6H_5$); δ 2.3 (s, $CH_3C_6H_5$); δ 3.8 (m, p-, m-, and o-$CH_3C_6H_4CH_2C_6H_5$, $C_6H_5CH_2C_6H_5$); δ 7.0-7.7 (m, aromatic protons). The side products of the reaction p-, m-, and o-$CH_3C_6H_4CH_2C_6H_5$ and $C_6H_5CH_2C_6H_5$ were confirmed by GC-MS.

EXAMPLE 22

Synthesis of Cl-MAO from Trityl Chloride

In the drybox, ¼ pipette of MAO (30% in toluene) was placed in a 4 mL vial. One drop of $(C_6H_5)_3CCl$ was added to the MAO solution. The exothermic reaction took place at once, resulting a red slurry. The color faded very fast. After about 20 min, the color slurry became an almost colorless solution. $^1$H NMR (THF-d8, 25°, 400 MHz): δ −0.5 (broad, MAO); δ −0.8 (s, TMA); δ 2.2 (s, $(C_6H_5)_3CCH_3$); δ 2.3 (s, $CH_3C_6H_5$); δ 7.0-7.7 (m, aromatic protons). The side product of the reaction, $(C_6H_5)_3CCH_3$, was confirmed by GC-MS.

EXAMPLE 23

Synthesis of Cl-MAO from $(CH_3)_2SnCl_2$

In the drybox, ¼ pipette of MAO (30% in toluene) was placed in a 4 mL vial. One drop of $(CH_3)_2SnCl_2$ was added to the MAO solution. The exothermic reaction took place at once, resulting a colorless solution. $^1$H NMR (THF-d8, 25°, 400 MHz): δ −0.5 (broad, MAO); δ −0.8 (s, TMA); δ 0.0 (s, $Sn(CH_3)_4$, very intense $^{119}$Sn satellites were observed); δ 2.3 (s, $CH_3C_6H_5$); δ 7.0-7.7 (m, aromatic protons). The side product of the reaction was $Sn(CH_3)_4$.

EXAMPLE 24

Synthesis of Partially Fluorinated Modified Methylaluminoxane from α,α,α-trifluorotoluene In the drybox, 2,6-di($^t$butyl)-4-methylphenol (BHT, 0.33 g; 10 mol %) in toluene (0.65 g) was added dropwise to MAO solution (30% in toluene; 3.0 g) in a 20 mL vial. The solution was stirred for 1 min. Next, $CF_3C_6H_5$ (0.044 g; 6 mol % F relative to aluminum) was added at once to the modified MAO solution. A greenish brown slurry was immediately obtained. The resultant slurry was placed in an 86° C. oil bath for 10 min. The greenish brown slurry became a clear brown solution. Major $^1$H NMR peaks (THF-d8, 25° C., 400 MHz): δ −0.5 ppm (broad, $CH_3$ of MAO); δ −0.8 (s, Al($CH_3$)$_3$); δ 1.4 (s, $C_6H_5C(CH_3)_3$); δ 1.7-1.8 (multi-singlet, $^t$Bu of BHT, p-, m-, and o-$CH_3C_6H_4C(CH_3)_2C_6H_5$); δ 2.2-2.3 (multi-singlet, $CH_3C_6H_5$ and Me of BHT); δ 7.0-7.5 (m, aromatic protons). $^9$F NMR (THF-d8, 25° C., 400 MHz): δ −140 (broad, F—Al of F-MAO).

COMPARATIVE EXAMPLE 1

Attempted Synthesis of Cl-MAO from 1,2-dichlorobenzene

In the drybox, a 4 mL vial was charged with MAO solids (0.2 g), toluene (0.5 g), and 1,2-dichlorobenzene (0.04 g). The mixture was shaken well, resulting in a colorless, clear solution. The solution was allowed to sit at room temperature for 12 days. Both on the day the reaction was initially mixed and at the end of 12 days, no significant reaction between 1,2-dichlorobenzene and MAO was detected based on $^1$H NMR spectra. The solution was almost completely gelled after 12 days.

Attempted syntheses of fluorinated aluminoxane, F-MAO, at ambient conditions as described in Example 2, using $C_6H_5F$, 1,4-$C_6F_2H_4$, $C_6F_6$, or $CF_3(CF_2)_4CF_3$ instead of $CF_3C_6H_5$ did not result in any observable reaction.

EXAMPLE 25

Polymerization with Unsupported F-MAO as Cocatalyst

For homogeneous ethylene polymerizations, tests were carried out in a 2 L autoclave using cyclohexane as the solvent. The reaction temperature was maintained at 135° C., and the pressure was maintained at 140 psig. The F-MAO was prepared from MAO and $CF_3C_6H_5$ according to the procedure similar to Example 2. The metallocene, rac-1,2-bis[indenyl]-ethylene-zirconium dichloride toluene solution and F-MAO solution, through separated inlets, were simultaneously added to the autoclave, following by the introduction of high pressure ethylene gas. Polymerization was conducted for 30 minutes. Results are summarized in Table 2.

TABLE 2

| Run | Activator | F content (relative to Al) | Al content | Zr content | Activity (1000 kg PE/g Zr/hr) |
|---|---|---|---|---|---|
| comparative | MAO | 0 mol % | 0.981 mmol | 2.15 µmol | 1.1 |
| 1a | F-MAO | 0.5 mol % | 0.966 mmol | 2.15 µmol | 1.0 |
| 1b | F-MAO | 0.5 mol % | 0.980 mmol | 2.15 µmol | 1.1 |
| 2a | F-MAO | 1.0 mol % | 0.962 mmol | 2.15 µmol | 1.0 |
| 2b | F-MAO | 1.0 mol % | 0.964 mmol | 2.15 µmol | 1.1 |
| 3a | F-MAO | 2 mol % | 0.998 mmol | 2.15 µmol | 1.3 |
| 3b | F-MAO | 2 mol % | 0.962 mmol | 2.15 µmol | 1.4 |
| 4a | F-MAO | 4 mol % | 0.958 mmol | 2.15 µmol | 1.3 |
| 4b | F-MAO | 4 mol % | 0.976 mmol | 2.15 µmol | 1.4 |
| 5a | F-MAO | 6 mol % | 0.944 mmol | 2.15 µmol | 1.5 |
| 5b | F-MAO | 6 mol % | 0.994 mmol | 2.15 µmol | 1.5 |
| 6a | F-MAO | 12 (8.1) mol %* | 0.964 mmol | 2.15 µmol | 1.4 |
| 6b | F-MAO | 12 (8.1) mol %* | 0.959 mmol | 2.15 µmol | 1.4 |

*A precipitate formed; the solution did not contain expected Al or F products. The number in parentheses is the amount of fluorine in the solution phase, as determined by NMR.

EXAMPLE 26

Polymerization with Unsupported F-MAO as Cocatalyst

For homogeneous ethylene polymerizations, tests were carried out in a 2 L autoclave using cyclohexane as the solvent. The reaction temperature was maintained at 70° C., and the pressure was maintained at 50 psig. The F-MAO was synthesized from MAO and $CF_3C_6H_5$ according to the procedure similar to Example 2. The metallocene, rac-1,2-bis[indenyl]-ethylene-zirconium dimethyl toluene solution and F-MAO solution, through separated inlets, were simultaneously added to the autoclave, followed by the introduction of high pressure ethylene gas. Polymerization was conducted for 30 minutes, except for Run 3a, which was stopped after 16 minutes due to too rapid reaction that froze the stirrer. Results are summarized in Table 3.

TABLE 3

| Run | Activator | F content (relative to Al) | Al content | Zr content | Activity (kg PE/g Zr/hr) |
|---|---|---|---|---|---|
| comparative | MAO | 0 mol % | 0.931 mmol | 2.15 µmol | 603 |
| comparative | MAO | 0 mol % | 0.895 mmol | 2.15 µmol | 709 |
| 1a | F-MAO | 2 mol % | 0.901 mmol | 2.15 µmol | 759 |
| 1b | F-MAO | 2 mol % | 0.895 mmol | 2.15 µmol | 681 |
| 2a | F-MAO | 4 mol % | 0.862 mmol | 1.08 µmol | 1336 |
| 3a | F-MAO | 6 mol % | 0.935 mmol | 2.16 µmol | 2088* |
| 3b | F-MAO | 6 mol % | 1.02 mmol | 1.08 µmol | 1456 |

*Too active to control reaction temperature; the stirrer was frozen after 16 minutes.

EXAMPLE 27

Polymerization with Unsupported Cl-MAO as Cocatalyst

Homogeneous ethylene polymerization tests were carried out in a 2 L autoclave using cyclohexane as the solvent. The reaction temperature was maintained at 70° C., and the pressure was maintained at 140 psig. The Cl-MAO was synthesized from MAO and $CCl_3C_6H_5$ in Example 19. The metallocene, rac-1,2-bis[indenyl]-ethylene-zirconium dichloride as a toluene solution and the Cl-MAO solution, were added simultaneously to the autoclave, through separate inlets, followed by the introduction of high pressure ethylene gas. A run using F-MAO in place of the Cl-MAO was also performed for comparison between the two (F-MAO and Cl-MAO). Results are summarized in Table 4.

TABLE 4

| Run | Activator | X content (relative to Al) | Al content | Zr content | Activity (kg PE/g Zr/hr) |
|---|---|---|---|---|---|
| comparative | MAO | 0 mol % | 0.841 mmol | 2.15 µmol | 479.4 |
| 1 | F-MAO | 4 mol % | 0.890 mmol | 2.15 µmol | 883.3 |
| 2 | Cl-MAO | 4 mol % | 0.867 mmol | 2.15 µmol | 518.2 |
| 3 | Cl-MAO | 4 mol % | 0.847 mmol | 2.15 µmol | 486.5 |

EXAMPLE 28

Synthesis of FSi-MAO with 2 Mol % F Relative to Aluminum

Methylaluminoxane (MAO) solution in toluene (30%, 40.4 g, 214.1 mmol Al) was placed in a reaction bottle. Poly[methyltrifluoropropylsiloxane] (PMTFPS, 0.24 g, 4.28 mmol F) was slowly added to the bottle at room temperature. Initially, the silicone was insoluble or rather immiscible. Dissolution slowly occurred with an exothermic reaction. The solution turned yellowish. The mixture was stirred at room temperature overnight. The resulting solution was colorless and remained gel-free in the drybox for over six months.

EXAMPLE 29

Synthesis of FSi-MAO with 4 Mol % F Relative to Aluminum

MAO in toluene (30%, 40.5 g, 214.6 mmol Al) was treated with fluorosilicone (PMTFPS, 0.49 g, 8.58 mmol F) as described in Example 28. After stirring overnight at room temperature, the mixture remained only slightly yellowish. The yellow color disappeared after about 2 days. The solution remained colorless and gel-free for over six months at room temperature in the drybox under a nitrogen atmosphere.

EXAMPLE 30

Synthesis of FSi-MAO with 6 Mol % F Relative to Aluminum

MAO in toluene (30%, 41.7 g, 221.01 mmol Al) was treated with fluorosilicone (PMTFPS, 0.75 g, 6 mole % F) as described in Example 28. The yellow color remained for a couple of days, after which the product remained colorless and gel-free for over six months.

EXAMPLE 31

Synthesis of FSi-MAO with 10 Mol % F Relative to Aluminum

MAO in toluene (30%, 39.8 g, 210.9 mmol Al) was allowed to react with fluorosilicone (PMTFPS, 1.2 g, 10 mole % F) as described in Example 28.

EXAMPLE 32

Synthesis of FSi-MAO with 12 Mol % F Relative to Aluminum

MAO in toluene (30%, 38.9 g, 206.2 mmol Al) and fluorosilicone (PMTFPS, 1.4 g, 12 mole % F) were allowed to react to produce a bright yellow solution product.

EXAMPLE 33

Synthesis of FSi-MAO with 6 Mol % F Relative to Aluminum

MAO in toluene (30%, 76.9 g, 384.5 mmol Al) was treated with monomeric fluorosilicone, trifluoropropylheptamethyltrisiloxane (TFPHMTS, 2.45 g, 6 mole % F). The exothermic reaction produced a yellowish solution product. The yellow solution was heated at 80° C. and then allowed to cool to room temperature overnight. The resulting colorless solution was filtered through a medium frit.

EXAMPLE 34

Synthesis of FSi-MAO with 4.5 Mol % F Relative to Aluminum

MAO in toluene (30%, 85.5 g, 442.9 mmol Al) was allowed to react with a cyclic fluorosilicone, methyltrifluoropropylcyclotrisiloxane (MTFPCTS, 1.04 g, 4.5 mole % F). The resulting yellow solution was heated at 80° C. for 4 hours and then allowed to cool to RT overnight. The resulting colorless solution was filtered through a medium frit.

EXAMPLE 35

Supporting of FSi-MAO on Silica

Silica was calcined at 600° C. An FSi-MAO solution from each of Examples 27 to 31 was used to prepare silica supported cocatalyst systems. Silica (2 g) was suspended in toluene (20 g). FSi-MAO solution (17 mmol Al) was added to the slurry in a reaction bottle. The bottle was placed on a shaker for about 2 hours. The mixture was filtered. The solid residue was washed with toluene and cyclohexane. The supported FSi-MAO was vacuum dried in the under $N_2$ in the drybox overnight at room temperature.

EXAMPLE 36

Synthesis of FSi-MAO with 1.5 Mol % F Relative to Aluminum

MAO in toluene (60 g, 30 wt %; 300 mmol Al) was placed in a 250 mL reaction bottle. Poly[methyl(3,3,3-trifluoropropyl)siloxane] (0.9 g, 4.5 mmol, 1.5 mol % F per Al) was added at once. Slowly, the reaction became exothermic. Initially the silicone was insoluble in toluene and caused the cloudy look of the solution. The mixture was allowed to stir overnight. It then became slightly yellow but clear. The mixture was then heated at 80° C. for 2 hours with vigorous stirring. The light yellow color became lighter and lighter. The mixture was then cooled to room temperature and filtered through a medium frit, resulting a foamy filtrate.

EXAMPLE 37

Supporting of FSi-MAO with 12 Mol % F Relative to Al on Silica

In the drybox, MAO (30%; 59.9 g) was weighed into an 8 oz bottle with a magnetic stirring bar. Poly[methyl(3,3,3-trifluoropropyl)siloxane] (1.20 g) was added to the MAO solution at once. The resultant cloud solution was allowed to stir overnight at room temperature. After overnight stirring, the cloudy solution had turned light yellow and clear. The reaction bottle was then placed in an oil bath set at 80° C. for 120 min with vigorous stirring. The yellowish solution became almost colorless. The reaction bottle was then removed from the oil bath and allowed to cool to room temperature. The solution was filtered through a medium frit glass filter. An oven dried 300 mL flask, condenser, overhead stirrer and septum were assembled and placed in the oil bath. The FSi-MAO (17.7 g), silica (10.1 g), and toluene (45 g) were charged into the flask; the mixture was stirred at room temperature for 60 min.

EXAMPLE 38

Polymerization with Unsupported FSi-MAO as Cocatalyst

For homogeneous ethylene polymerizations, tests were carried out in a 2 L autoclave using cyclohexane as the solvent. The reaction temperature was maintained at 135° C., and the pressure was maintained at 140 psig. The FSi-MAO was synthesized from MAO and poly[methyl(3,3,3-trifluoropropyl)siloxane] according to the procedure of Example 34. The metallocene, rac-1,2-bis[indenyl]-ethylene-zirconium dichloride toluene solution and FSi-MAO solution, through separated inlets, were simultaneously added to the autoclave, followed by the introduction of high pressure ethylene gas. Polymerization was conducted for 30 minutes. Results are summarized in Table 5.

TABLE 5

| Run | Activator | F content (relative to Al) | Al content | Zr content | Activity (1000 kg PE/g Zr/hr) |
|---|---|---|---|---|---|
| comparative | MAO | 0 mol % | 0.981 mmol | 2.15 µmol | 1.1 |
| 1a | FSi-MAO | 2 mol % | 0.961 mmol | 2.15 µmol | 1.4 |
| 1b | FSi-MAO | 2 mol % | 0.959 mmol | 2.15 µmol | 1.4 |

EXAMPLE 39

Synthesis of F-MAO with 10 Mol % from (CH$_3$)$_2$AlF

Potassium fluoride (KF, 15.7 g, 270 mmol) was suspended in toluene (50 g). Dimethylaluminum chloride (50 g of 50 wt % solution in toluene, 270 mmol Al) was slowly added in aliquots over 50 minutes. Addition was controlled such that the reaction temperature (isotherm) was kept at about 50° C. After addition, the mixture was stirred for another one hour. The reaction was monitored by H-1 NMR by the disappearance of Me-AlCl peak and appearance of Me-AlF peak. The product, dimethylaluminum fluoride in toluene, was used as stock solution.

MAO in toluene (45 g, 225 mmol Al) was treated at room temperature with enough of the stock solution of dimethylaluminum fluoride in toluene(2.08 g, 11.25 mmol Al) to add 5 mol % (CH$_3$)$_2$AlF to the MAO. The amount of toluene solution of(CH$_3$)$_2$AlF added depends on the concentration of (CH$_3$)$_2$AlF. The mixture is stirred at room temperature for about two hours. A broad Al—F peak in F-19 NMR is indicative of the desired product. Clarification of gelled MAO was observed during this process. It is advisable however to use fresh MAO in order to assure better solution stability. This procedure was repeated, using enough of the stock solution of (CH$_3$)$_2$AlF in toluene to add 10 mol % (CH$_3$)$_2$AlF to the MAO.

COMPARATIVE EXAMPLE 2

Synthesis of Cl-MAO from CH$_2$Cl$_2$

A 30 wt % solution of MAO in toluene (5.0 g; 25 mmol Al) was placed in a 20 mL vial with a stirring bar. Neat CH$_2$Cl$_2$ (0.0845 g; 1.0 mmol Cl) was added at once and stirred at room temperature for 30 minutes; the temperature of the mixture increased. $^1$H NMR (400 MHz, 25° C., THF-d8) showed incomplete reaction to Cl-MAO, with unreacted CH$_2$Cl$_2$ (5.3 ppm). The solution was light yellow. A complicated mixture of organic by-products was observed. The TMA (−0.8 ppm) present in the MAO reacted faster with the CH$_2$Cl$_2$ than MAO did. Applying heat did not drive the reaction to the desired product.

COMPARATIVE EXAMPLE 3

Attempted Synthesis of F-MAO via Addition of MAO to α,α,α-trifluorotoluene

To a 20 mL vial were charged Cp$_2$ZrCl$_2$ (64.3 mg, 0.22 mmol, Aldrich), α,α,α-trifluorotoluene, (10.7 mg, Aldrich, Zr:F=1:1), and toluene (1.0 g). Then a 10 wt % solution of MAO in toluene (6.6 g, 11 mmol, 4.5 Al %, Albemarle, Al:Zr=50:1) was added dropwise to the mixture in the vial with stirring. After 3 drops of MAO had been added, a violent reaction was observed; a blue slurry material shot out of the vial. The addition of MAO was stopped.

Without wishing to be bound by theory, it is believed that very fast boiling of the solvent due to the exothermicity of the reaction caused the material to shoot out of the vial. It is also believed, again without wishing to be bound by theory, that a localized high concentration of α,α,α-trifluorotoluene overfluorinated some of the MAO to form species with a high number of Al—F units, while leaving the remainder of the MAO unhalogenated.

Further embodiments of the invention include:

aa) A haloaluminoxane composition wherein the halogen is fluorine, chlorine, and/or bromine, and wherein the amount of halogen atoms present in said composition is in the range of about 0.5 mole % to about 15 mole % relative to aluminum atoms, which composition is formed from components comprising (a) at least one aluminoxane and (b) at least one halogenation agent which is a halohydrocarbon which can be represented by the formula:

ArG$_n$ where Ar is an aromatic hydrocarbon ring system, G is —CX$_3$, —CX$_2$R, or —CXR$_2$, in which X is, independently, a fluorine atom, chlorine atom, or bromine atom, and in which R is, independently, a hydrogen atom or C$_{1-4}$ alkyl group; and n is 1 to 5.

ab) A composition as in aa) wherein said haloaluminoxane is a partially halogenated aluminoxane.

ac) A composition as in aa) wherein said aromatic compound is α,α,α-trichlorotoluene.

ad) A composition as in ac) wherein said haloaluminoxane is a partially chlorinated aluminoxane.

ae) A composition as in aa) wherein said haloaluminoxane is a partially halogenated aluminoxane.

af) A haloaluminoxane composition wherein the halogen is fluorine, chlorine, and/or bromine, and wherein the amount of halogen atoms present in said composition is in the range of about 0.5 mole % to about 15 mole % relative to aluminum atoms, which composition is formed from components comprising (a) at least one aluminoxane and (b) at least one halogenation agent which is a siloxane with at least one 3,3,3-trihalopropyl group, wherein said haloaluminoxane is a partially halogenated aluminoxane.

ag) A composition as in af) wherein said 3,3,3-trihalopropyl group is a 3,3,3-trifluoropropyl group.

ah) A composition as in aa)-aj) wherein said aluminoxane is methylaluminoxane, ethylaluminoxane, n-butylaluminoxane, or isobutylaluminoxane.

ai) A composition as in aa) wherein said aluminoxane is methylaluminoxane; wherein G is —CX$_3$; and wherein said haloaluminoxane composition is a partially halogenated aluminoxane.

aj) A composition as in am) wherein X is fluorine.

ak) A composition as in aa) wherein said aluminoxane is methylaluminoxane; wherein (b) is α,α,α-trichlorotoluene or triphenylchloromethane; and wherein said haloaluminoxane composition is a partially chlorinated aluminoxane.

al) A composition as in any of aa) to ak) wherein the amount of halogen atoms present in said composition is in the range of about 2 mole % to about 10 mole % relative to aluminum atoms.

am) A composition as in any of aa) to ak) wherein the amount of halogen atoms present in said composition is in the range of about 2 mole % to about 6 mole % relative to aluminum atoms.

an) A supported haloaluminoxane composition which is formed from components comprising (a) at least one aluminoxane and
(b) at least one halogenation agent which is
  (i) at least one halohydrocarbon of the formula R$_n$CX$_4$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms, or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or (vi) mixtures of any two or more of (i)-(v), and (c) a support or carrier which is an inorganic oxide.

ao) A composition as in an) wherein (b) is a halohydrocarbon which can be represented by the formula:

$$ArG_n$$

where Ar is an aromatic hydrocarbon ring system, G is —$CX_3$, —$CX_2R$, or —$CXR_2$, in which X is, independently, a fluorine atom, chlorine atom, or bromine atom, and in which R is, independently, a hydrogen atom or $C_{1-4}$ alkyl group; and n is 1 to 5.

ap) A composition as in ao) wherein said haloaluminoxane is a partially halogenated aluminoxane.

aq) A composition as in an) wherein said aromatic compound is α,α,α-trichlorotoluene or triphenylchloromethane.

ar) A composition as in aq) wherein said haloaluminoxane is a partially chlorinated aluminoxane.

as) A composition as in an) wherein said haloaluminoxane is a partially halogenated aluminoxane.

at) A composition as in as) wherein (b) is a siloxane with at least one 3,3,3-trihalopropyl group.

au) A composition as in at) wherein said 3,3,3-trihalopropyl group is a 3,3,3-trifluoropropyl group.

av) A composition as in an)-au) wherein said aluminoxane is methylaluminoxane, ethylaluminoxane, n-butylaluminoxane, or isobutylaluminoxane.

aw) A composition as in at) wherein said aluminoxane is methylaluminoxane; wherein G is —$CX_3$; and wherein said haloaluminoxane composition is a partially halogenated aluminoxane.

ax) A composition as in aw) wherein X is fluorine.

ay) A composition as in any of an)-ax) wherein said inorganic oxide is silica.

az) A composition as in an) wherein said aluminoxane is methylaluminoxane; wherein (b) is α,α,α-trichlorotoluene ortriphenylchloromethane; wherein said inorganic oxide is silica; and wherein said haloaluminoxane composition is a partially chlorinated aluminoxane.

ba) A process which comprises mixing, in an inert, anhydrous environment, (a) at least one aluminoxane and (b) at least one halogenation agent which is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently, a hydrocarbyl group having from one to about twenty carbon atoms, or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or (vi) mixtures of any two or more of (i)-(v), wherein the amount of halogen atoms is in the range of about 0.5 mole % to about 15 mole % relative to aluminum atoms, such that a haloaluminoxane composition is formed.

bb) A process according to ba) wherein (b) is a halohydrocarbon which can be represented by the formula:

$$ArG_n$$

where Ar is an aromatic hydrocarbon ring system, G is —$CX_3$, —$CX_2R$, or —$CXR_2$, in which X is, independently, a fluorine atom, chlorine atom, or bromine atom, and in which R is, independently, a hydrogen atom or $C_{1-4}$ alkyl group; and n is 1 to 5.

bc) A process according to bb) wherein said haloaluminoxane is a partially halogenated aluminoxane.

bd) A process according to bb) wherein said aromatic compound is α,α,α-trichlorotoluene.

be) A process according to ba) wherein said haloaluminoxane is a partially halogenated aluminoxane.

bf) A process according to be) wherein (b) is a siloxane with at least one 3,3,3 -trihalopropyl group.

bg) A process according to bo) wherein said 3,3,3-trihalopropyl group is a 3,3,3-trifluoropropyl group.

bh) A process according to bb)-bg) wherein said aluminoxane is methylaluminoxane, ethylaluminoxane, n-butylaluminoxane, or isobutylaluminoxane.

bi) A process according to bb) wherein said aluminoxane is methylaluminoxane; wherein G is —$CX_3$; and wherein said haloaluminoxane composition is a partially halogenated aluminoxane.

bj) A process according to bi) wherein X is fluorine.

bk) A process according to any of ba)-bj) wherein said inert, anhydrous environment is an aromatic hydrocarbon.

bx) A process according to bk) wherein said aromatic hydrocarbon is toluene.

by) A process according to bb) wherein said inert, anhydrous environment is toluene; wherein said aluminoxane is methylaluminoxane; wherein G is —$CX_3$; and wherein said haloaluminoxane composition is a partially chlorinated aluminoxane.

bz) A process according to ba) wherein said inert, anhydrous environment is toluene; wherein said aluminoxane is methylaluminoxane; wherein (b) is α,α,α-trichlorotoluene or triphenylchloromethane; and wherein said haloaluminoxane composition is a partially chlorinated aluminoxane.

ca) A process according to ba) further comprising forming a supported haloaluminoxane by
A) contacting a support or carrier which is an inorganic oxide with (a) and (b), or
B) contacting said haloaluminoxane composition with a support or carrier which is an inorganic oxide,
such that a supported haloaluminoxane is formed.

cb) A process according to ca) wherein (b) is a halohydrocarbon which can be represented by the formula:

$ArG_n$ where Ar is an aromatic hydrocarbon ring system, G is $-CX_3$, $-CX_2R$, or $-CXR_2$, in which X is, independently, a fluorine atom, chlorine atom, or bromine atom, and in which R is, independently, a hydrogen atom or $C_{1-4}$ alkyl group; and n is 1 to 5.

cd) A process according to cb) wherein said haloaluminoxane is a partially halogenated aluminoxane.

ce) A process according to cb) wherein said aromatic compound is α,α,α-trichlorotoluene.

cf) A process according to ce) wherein said haloaluminoxane is a partially chlorinated aluminoxane.

cg) A process according to ca) wherein said haloaluminoxane is a partially halogenated aluminoxane.

ch) A process according to cg) wherein (b) is a siloxane with at least one 3,3,3-trihalopropyl group.

ci) A process according to ch) wherein said 3,3,3-trihalopropyl group is a 3,3,3-trifluoropropyl group.

cj) A process according to cb)-ci) wherein said aluminoxane is methylaluminoxane, ethylaluminoxane, n-butylaluminoxane, or isobutylaluminoxane.

ck) A process according to cb) wherein said aluminoxane is methylaluminoxane; wherein G is $-CX_3$; and wherein said haloaluminoxane composition is a partially halogenated aluminoxane.

cl) A process according to cj) or ck) wherein X is fluorine.

cm) A process according to any of ca)-cl) wherein said inert, anhydrous environment is an aromatic hydrocarbon.

cn) A process according to cm) wherein said aromatic hydrocarbon is toluene.

co) A process as in any of ca)-cn) wherein said inorganic oxide is silica.

cp) A process according to ca) wherein said inert, anhydrous environment is toluene; wherein said aluminoxane is methylaluminoxane; wherein G is $-CX_3$; wherein said inorganic oxide is silica; and wherein said haloaluminoxane composition is a partially halogenated aluminoxane.

cq) A process according to ca) wherein said inert, anhydrous environment is toluene; wherein said aluminoxane is methylaluminoxane; wherein (b) is α,α,α-trichlorotoluene or triphenylchloromethane; wherein said inorganic oxide is silica; and wherein said haloaluminoxane composition is a partially chlorinated aluminoxane.

cr) A composition formed from interaction between components comprising
(I) either a haloaluminoxane wherein the amount of halogen atoms is in the range of about 0.5 mole % to about 15 mole % relative to aluminum atoms, or
(a) at least one aluminoxane and (b) at least one halogenation agent which is
  (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or
  (ii) at least one siloxane having at least one labile halogen atom in the molecule, wherein each halogen atom is, independently, fluorine, chlorine, or bromine; or
  (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or
  (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or
  (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or
  (vi) mixtures of any two or more of (i)-(v),
  wherein the amount of halogen atoms is in the range of about 0.5 mole % to about 15 mole % relative to aluminum atoms; and
(II) at least one catalyst compound or complex of a transition metal of Groups 3 to 11 including the lanthanide series and the actinide series.

cs) A composition as in cr) wherein (b) is a halohydrocarbon which can be represented by the formula:

$ArG_n$ where Ar is an aromatic hydrocarbon ring system, G is $-CX_3$, $-CX_2R$, or $-CXR_2$, in which X is, independently, a fluorine atom, chlorine atom, or bromine atom, and in which R is, independently, a hydrogen atom or $C_{1-4}$ alkyl group; and n is 1 to 5.

ct) A composition as in cs) wherein said haloaluminoxane is a partially halogenated aluminoxane.

cu) A composition as in cs) wherein said aromatic compound is α,α,α-trichlorotoluene.

cv) A composition as in cu) wherein said haloaluminoxane is a partially chlorinated aluminoxane.

cw) A composition as in cr) wherein said haloaluminoxane is a partially halogenated aluminoxane.

cx) A composition as in cw) wherein (b) is a siloxane with at least one 3,3,3-trihalopropyl group.

cy) A composition as in cr) wherein said 3,3,3-trihalopropyl group is a 3,3,3-trifluoropropyl group.

cz) A composition as in cr)-cy) wherein said aluminoxane is methylaluminoxane, ethylaluminoxane, n-butylaluminoxane, or isobutylaluminoxane.

da) A composition as in cs) wherein said aluminoxane is methylaluminoxane; wherein G is $-CX_3$; and wherein said haloaluminoxane composition is a partially halogenated aluminoxane.

db) A composition as in da) wherein X is fluorine.

de) A composition as in cr) wherein said aluminoxane is methylaluminoxane; wherein (b) is α,α,α-trichlorotoluene or triphenylchloromethane; and wherein said haloaluminoxane composition is a partially chlorinated aluminoxane.

df) A composition as in any of cr)-de) supported on a catalyst support or carrier.

dg) A composition as in df) wherein said catalyst support or carrier is an inorganic oxide.

dh) A composition as in dg) wherein said inorganic oxide is silica, alumina, or silica-alumina.
di) A composition as in any of cr)-dh) wherein said transition metal compound is comprised of a halide of a transition metal of Group 4.
dj) A composition as in di) wherein said transition metal is zirconium.
dk) A process for forming a catalyst composition which comprises interacting, in an inert aromatic solvent, components comprising
(I) either a haloaluminoxane wherein the amount of halogen atoms is in the range of about 0.5 mole % to about 15 mole % relative to aluminum atoms, or
(a) at least one aluminoxane and (b) at least one halogenation agent which is
  (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or
  (ii) at least one siloxane having at least one labile halogen atom in the molecule, wherein each halogen atom is, independently, fluorine, chlorine, or bromine; or
  (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or
  (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or
  (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or
  (vi) mixtures of any two or more of (i)-(v), wherein the amount of halogen atoms is in the range of about 0.5 mole % to about 15 mole % relative to aluminum atoms; and
(II) at least one catalyst compound or complex of a transition metal of Groups 3 to 11 including the lanthanide series and the actinide series.
dl) A process according to dk) wherein (b) is a halohydrocarbon which can be represented by the formula:

$$ArG_n$$

where Ar is an aromatic hydrocarbon ring system, G is —$CX_3$, —$CX_2R$, or —$CXR_2$, in which X is, independently, a fluorine atom, chlorine atom, or bromine atom, and in which R is, independently, a hydrogen atom or $C_{1-4}$ alkyl group; and n is 1 to 5.
dm) A process according to dl) wherein said haloaluminoxane is a partially halogenated aluminoxane.
dn) A process according to dl) wherein said aromatic compound is α,α,α-trichlorotoluene.
do) A process according to dn) wherein said haloaluminoxane is a partially chlorinated aluminoxane.
dp) A process according to dk) wherein said haloaluminoxane is a partially halogenated aluminoxane.
dq) A process according to dp) wherein (b) is a siloxane with at least one 3,3,3-trihalopropyl group.
dr) A process according to dq) wherein said 3,3,3-trihalopropyl group is a 3,3,3-trifluoropropyl group.
ds) A process according to any of dl)-dr) wherein said aluminoxane is methylaluminoxane, ethylaluminoxane, n-butylaluminoxane, or isobutylaluminoxane.
dt) A process according to dl) wherein said aluminoxane is methylaluminoxane; wherein G is —$CX_3$; and wherein said haloaluminoxane composition is a partially halogenated aluminoxane.
du) A process according to dt) wherein X is fluorine.
dv) A process according to dk) wherein said aluminoxane is methylaluminoxane; wherein (b) is α,α,α-trichlorotoluene or triphenylchloromethane; and wherein said haloaluminoxane composition is a partially chlorinated aluminoxane.
dw) A process according to any of dk)-dv) wherein said transition metal compound is comprised of a halide of a transition metal of Group 4.
dx) A process according to dw) wherein said transition metal is zirconium.
dy) A process according to dk) further comprising forming a supported catalyst composition by
  A) contacting a support material with (I) and (II),
  B) contacting (I) with a support material,
  C) contacting (II) with a support material, or
  D) contacting said catalyst composition with a support material, such that a supported haloaluminoxane is formed.
dz) A process according to dy) wherein (b) is a halohydrocarbon which can be represented by the formula:

$$ArG_n$$

where Ar is an aromatic hydrocarbon ring system, G is —$CX_3$, —$CX_2R$, or —$CXR_2$, in which X is, independently, a fluorine atom, chlorine atom, or bromine atom, and in which R is, independently, a hydrogen atom or $C_{1-4}$ alkyl group; and n is 1 to 5.
ea) A process according to dz) wherein said haloaluminoxane is a partially halogenated aluminoxane.
eb) A process according to dz) wherein said aromatic compound is α,α,α-trichlorotoluene.
ec) A process according to eb) wherein said haloaluminoxane is a partially chlorinated aluminoxane.
ed) A process according to dy) wherein said haloaluminoxane is a partially halogenated aluminoxane.
ee) A process according to ed) wherein (b) is a siloxane with at least one 3,3,3-trihalopropyl group.
ef) A process according to ee) wherein said 3,3,3-trihalopropyl group is a 3,3,3-trifluoropropyl group.
eg) A process according to dz)-ef) wherein said aluminoxane is methylaluminoxane, ethylaluminoxane, n-butylaluminoxane, or isobutylaluminoxane.
eh) A process according to dy) wherein said aluminoxane is methylaluminoxane; wherein G is —$CX_3$; and wherein said haloaluminoxane composition is a partially halogenated aluminoxane.
ei) A process according to eh) wherein the halogen is fluorine.
ej) A process according to dy) wherein said aluminoxane is methylaluminoxane; wherein (b) is α,α,α-trichlorotoluene or triphenylchloromethane; and wherein said haloaluminoxane composition is a partially chlorinated aluminoxane.
ek) A process according to any of dy)-ej) wherein said transition metal compound is comprised of a halide of a transition metal of Group 4.
el) A process according to ek) wherein said transition metal is zirconium.

em) A process according to any of dy)-el) wherein said inert, anhydrous environment is an aromatic hydrocarbon.

en) A process according to em) wherein said aromatic hydrocarbon is toluene.

eo) A process as in any of dy)-en) wherein said catalyst support or carrier is an inorganic oxide.

ep) A process as in eo) wherein said inorganic oxide is a silica, alumina, or silica-alumina catalyst support or carrier.

eq) A process as in ep) wherein said inorganic oxide is silica.

er) A process of producing a polyolefin polymer, which process comprises polymerizing at least one polymerizable olefinic monomer in the presence of a catalyst composition comprised of (I) either a haloaluminoxane, wherein the amount of halogen atoms is in the range of about 0.5 mole % to about 15 mole % relative to aluminum atoms, or (a) at least one aluminoxane and (b) at least one halogenation agent which is
  (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or
  (ii) at least one siloxane having at least one labile halogen atom in the molecule, wherein each halogen atom is, independently, fluorine, chlorine, or bromine; or
  (iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or
  (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or
  (v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or
  (vi) mixtures of any two or more of (i)-(v),
  wherein the amount of halogen atoms is in the range of about 0.5 mole % to about 15 mole % relative to aluminum atoms; and (II) at least one catalyst compound or complex of a transition metal of Groups 3 to 11 including the lanthanide series and the actinide series.

es) A process according to er) wherein (b) is a halohydrocarbon which can be represented by the formula:

$ArG_n$ where Ar is an aromatic hydrocarbon ring system, G is —$CX_3$, —$CX_2R$, or —$CXR_2$, in which X is, independently, a fluorine atom, chlorine atom, or bromine atom, and in which R is, independently, a hydrogen atom or $C_{1-4}$ alkyl group; and n is 1 to 5.

et) A process according to es) wherein said haloaluminoxane is a partially halogenated aluminoxane.

eu) A process according to es) wherein said aromatic compound is α,α,α-trichlorotoluene.

ev) A process according to eu) wherein said haloaluminoxane is a partially chlorinated aluminoxane.

ew) A process according to er) wherein said haloaluminoxane is a partially halogenated aluminoxane.

ex) A process according to ew) wherein (b) is a siloxane with at least one 3,3,3-trihalopropyl group.

ey) A process according to ex) wherein said 3,3,3-trihalopropyl group, is a 3,3,3-trifluoropropyl group.

ez) A process according to any of es)-ey) wherein said aluminoxane is methylaluminoxane, ethylaluminoxane, n-butylaluminoxane, or isobutylaluminoxane.

fa) A process according to es) wherein said aluminoxane is methylaluminoxane; wherein G is —$CX_3$; and wherein said haloaluminoxane composition is a partially halogenated aluminoxane.

fb) A process according to fa) wherein the halogen is fluorine.

fc) A process according to er) wherein said aluminoxane is methylaluminoxane; wherein (b) is α,α,α-trichlorotoluene or triphenylchloromethane; and wherein said haloaluminoxane composition is a partially chlorinated aluminoxane.

fd) A process according to any of er)-fc) wherein said transition metal compound is comprised of a halide of a transition metal of Group 4.

fe) A process according to fd) wherein said transition metal is zirconium.

ff) A process as in any of er)-fe) wherein ethylene or propylene is subjected to homopolymerization.

fg) A process as in any of er)-fe) wherein ethylene and at least one alpha-olefin having in the range of 3 to about 8 carbon atoms are subjected to copolymerization.

fh) A process as in any of er)-fz) wherein said catalyst composition is supported on a catalyst support or carrier.

fi) A process as in fh) wherein said catalyst support or carrier is an inorganic oxide.

fj) A process as in fi) wherein said inorganic oxide is silica, alumina, or silica-alumina.

fk) A process as in ff) wherein said catalyst composition is supported on an inorganic oxide.

fl) A process as in fk) wherein said inorganic oxide is silica, alumina, or silica-alumina.

fm) A process as in fg) wherein said catalyst composition is, supported on an inorganic oxide.

fn) A process as in fm) wherein said inorganic oxide is silica, alumina, or silica-alumina.

fo) A composition as in ah) wherein said halogenation agent is a silane, and wherein said silane has the formula $(CH_3)_nSiX_{4-n}$, where n=1-3, and X is, independently, fluorine, chlorine or bromine.

fp) A composition as in fo) wherein said aluminoxane is methylaluminoxane, ethylaluminoxane, n-butylaluminoxane, or isobutylaluminoxane.

fq) A composition as in as) wherein said halogenation agent is a silane, and wherein said silane has the formula $(CH_3)_nSiX_{4-n}$, where n=1-3, and X is, independently, fluorine, chlorine or bromine.

fr) A composition as in fq) wherein said aluminoxane is methylaluminoxane, ethylaluminoxane, n-butylaluminoxane, or isobutylaluminoxane.

fs) A process as in be) wherein said halogenation agent is a silane, and wherein said silane has the formula $(CH_3)_nSiX_{4-n}$, where n=1-3, and X is, independently, fluorine, chlorine or bromine.

ft) A process as in fs) wherein said aluminoxane is methylaluminoxane, ethylaluminoxane, n-butylaluminoxane, or isobutylaluminoxane.

fu) A process as in cg) wherein said halogenation agent is a silane, and wherein said silane has the formula $(CH_3)_n SiX_{4-n}$, where n=1-3, and X is, independently, fluorine, chlorine or bromine.

fv) A process as in fu) wherein said aluminoxane is methylaluminoxane, ethylaluminoxane, n-butylaluminoxane, or isobutylaluminoxane.

fw) A composition as in df) wherein said halogenation agent is a silane, and wherein said silane has the formula $(CH_3)_n SiX_{4-n}$, where n=1-3, and X is, independently, fluorine, chlorine or bromine.

fx) A composition as in fw) wherein said aluminoxane is methylaluminoxane, ethylaluminoxane, n-butylaluminoxane, or isobutylaluminoxane.

fy) A process as in do) wherein said halogenation agent is a silane, and wherein said silane has the formula $(CH_3)_n SiX_{4-n}$, where n=1-3, and X is, independently, fluorine, chlorine or bromine.

fz) A process as in fy) wherein said aluminoxane is methylaluminoxane, ethylaluminoxane, n-butylaluminoxane, or isobutylaluminoxane.

ga) A process as in ed) wherein said halogenation agent is a silane, and wherein said silane has the formula $(CH_3)_n SiX_{4-n}$, where n=1-3, and X is, independently, fluorine, chlorine or bromine.

gb) A process as in ga) wherein said aluminoxane is methylaluminoxane, ethylaluminoxane, n-butylaluminoxane, or isobutylaluminoxane.

gc) A process as in ew) wherein said halogenation agent is a silane, and wherein said silane has the formula $(CH_3)_n SiX_{4-n}$, where n=1-3, and X is, independently, fluorine, chlorine or bromine.

gd) A process as in gc) wherein said aluminoxane is methylaluminoxane, ethylaluminoxane, n-butylaluminoxane, or isobutylaluminoxane.

gz) A haloaluminoxane composition wherein the halogen is fluorine, chlorine, and/or bromine, and wherein the amount of halogen atoms present in said composition is in the range of about 0.5 mole % to about 15 mole % relative to aluminum atoms, which composition is formed from components comprising
(a) at least one aluminum hydrocarbyl and
(b) at least one halogenation agent which is
  (i) at least one halohydrocarbon of the formula $R_n CX_{4-n}$, where n=1-3, X is, independently, fluorine, chlorine or bromine, and where R is, independently, a hydrogen atom or a hydrocarbyl group having from one to about twenty carbon atoms; or
  (ii) at least one siloxane having at least one labile halogen atom in the molecule, wherein each halogen atom is, independently, fluorine, chlorine, or bromine; or
  (iii) at least one silane of the formula $R'_n SiX_4 n$, where n=1-3, X is, independently, fluorine, chlorine or bromine, and where R' is, independently, a hydrocarbyl group having from one to about twenty carbon atoms, or
  (iv) at least one tin compound of the formula $R'_n SnX_{4-n}$, where n=1-3, X is, independently, fluorine, chlorine or bromine, and where R' is, independently, a hydrocarbyl group having from one to about twenty carbon atoms; or
  (v) at least one hydrocarbyl aluminum halide of the formula $R''_m AlX_{3-m}$, where m=1 or 2, where X is, independently, fluorine, chlorine or bromine, and where R" is, independently, a hydrocarbyl group having from one to about twenty carbon atoms; or
  (vi) mixtures of any two or more of (i)-(v). and
(c) a source of water.

ha) A composition as in gz) wherein (b) is a halohydrocarbon which can be represented by the formula:

$ArG_n$ where Ar is an aromatic hydrocarbon ring system, G is $-CX_3$, $-CX_2R$, or $-CXR_2$, in which X is, independently, a fluorine atom, chlorine atom, or bromine atom, and in which R is, independently, a hydrogen atom or $C_1$-4 alkyl group; and n is 1 to 5.

hb) A composition as in ha) wherein said haloaluminoxane is a partially halogenated aluminoxane.

hc) A composition as in ha) wherein said aromatic compound is α,α,α-trichlorotoluene.

hd) A composition as in hc) wherein said haloaluminoxane is a partially chlorinated aluminoxane.

he) A composition as in gz) wherein said halgenation agent is a halohydrocarbon, and wherein said halohydrocarbon is one in which at least one R is an aryl group.

hf) A composition as in he) wherein said halohydrocarbon is α,α,α-trifluorotoluene.

hg) A composition as in gz) wherein said haloaluminoxane is a partially halogenated aluminoxane.

hh) A composition as in hg) wherein (b) is at least one siloxane, silane, tin compound, or hydrocarbyl aluminum halide.

hi) A composition as in hh) wherein said halogenation agent is a silane.

hj) A composition as in hh) wherein said halogenation agent is a silane, and wherein said silane is triphenylfluorosilane or trimethylfluorosilane.

hk) A composition as in hh) wherein said halogenation agent is a siloxane, and wherein said siloxane is a trisiloxane or a tricyclosiloxane.

hl) A composition as in hh) wherein said halogenation agent is a siloxane, and wherein said siloxane is 3,3,3-trifluoropropylheptamethyltrisiloxane, 3,3,3-trifluoropropylheptamethylcyclotrisiloxane, or poly[methyl(3,3,3-trifluoropropyl)siloxane].

hm) A composition as in hh) wherein (b) is a siloxane with at least one 3,3,3-trihalopropyl group.

hn) A composition as in hm) wherein said 3,3,3-trihalopropyl group is a 3,3,3-trifluoropropyl group.

ho) A composition as in ha)-hn) wherein said aluminum hydrocarbyl is trimethylaluminum, triethylaluminum, tri-n-butylaluminum, or triisobutylaluminum.

hp) A composition as in ha) wherein said aluminoxane is methylaluminoxane; wherein G is $-CX_3$; and wherein said haloaluminoxane composition is a partially halogenated aluminoxane.

hq) A composition as in hp) wherein X is fluorine.

hr) A composition as in gz) wherein said aluminum hydrocarbyl is trimethylaluminum; wherein (b) is α,α,α-trichlorotoluene or triphenylchloromethane; and wherein said haloaluminoxane composition is a partially chlorinated aluminoxane.

hs) A composition as in any of gz) to hr) wherein the amount of halogen atoms present in said composition is in the range of about 2 mole % to about 10 mole % relative to aluminum atoms.

ht) A composition as in any of gz) to hr) wherein the amount of halogen atoms present in said composition is in the range of about 2 mole % to about 6 mole % relative to aluminum atoms.

hu) A composition as in gz) wherein the amount of halogen atoms present in said composition is in the range of about 2 mole % to about 10 mole % relative to aluminum atoms.

hv) A composition as in gz) wherein the halogen is fluorine.

hw) A composition as in gz) wherein the hydrocarbyl groups of said aluminoxane are saturated, and have from one to about twenty carbon atoms.

hx) A composition as in gz) wherein said aluminum hydrocarbyl is trimethylaluminum, triethylaluminum, tri-n-butylaluminum, or triisobutylaluminum.

hy) A composition which comprises a haloaluminoxane composition as in gz) supported on a catalyst support or carrier.

hz) A composition as in gz) wherein said haloaluminoxane composition is supported on a catalyst support or carrier, and wherein said inorganic support or carrier is silica, alumina, or silica-alumina.

ia) A composition as in hz) wherein said aluminum hydrocarbyl is trimethylaluminum, triethylaluminum, tri-n-butylaluminum, or triisobutylaluminum.

ib) A composition as in hz) wherein (b) is at least one halohydrocarbon, and wherein said halohydrocarbon is one in which at least one R is an aryl group.

ic) A composition as in hz) wherein said aluminum hydrocarbyl is trimethylaluminum, triethylaluminum, tri-n-butylaluminum, or triisobutylaluminum, wherein (b) is at least one halohydrocarbon, and wherein said halohydrocarbon is one in which at least one R is an aryl group.

id) A composition as in ic) wherein said halohydrocarbon is α,α,α-trifluorotoluene, and wherein said catalyst support or carrier is silica.

ie) A composition as in hz) wherein said haloaluminoxane composition is a partially halogenated aluminoxane.

if) A composition as in ie) wherein said aluminum hydrocarbyl is trimethylaluminum, triethylaluminum, tri-n-butylaluminum, or triisobutylaluminum, and wherein said inorganic support or carrier is silica, alumina, or silica-alumina.

ij) A composition as in ie) wherein said aluminum hydrocarbyl is trimethylaluminum, triethylaluminum, tri-n-butylaluminum, or triisobutylaluminum; wherein said halogenation agent is a siloxane; and wherein said siloxane is a trisiloxane or a tricyclosiloxane.

ik) A composition as in ie) wherein said halogenation agent is a siloxane, and wherein said siloxane is 3,3,3-trifluoropropylheptamethyltrisiloxane, 3,3,3-trifluoropropylheptamethylcyclotrisiloxane, or poly[methyl(3,3,3-trifluoropropyl)siloxane].

il) A composition as in ie) wherein said aluminum hydrocarbyl is trimethylaluminum, triethylaluminum, tri-n-butylaluminum, or triisobutylaluminum.

im) A composition as in ie) wherein said aluminum hydrocarbyl is trimethylaluminum; wherein said halogenation agent is a siloxane, wherein said siloxane is poly[methyl(3,3,3-trifluoropropyl)siloxane], and wherein said support is silica.

io) A process which comprises mixing, in an inert environment,
(a) at least one aluminum hydrocarbyl and
(b) at least one halogenation agent which is
   (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or
   (ii) at least one siloxane having at least one labile halogen atom in the molecule, wherein each halogen atom is, independently, fluorine, chlorine, or bromine; or
   (iii) at least one silane of the formula $R'_nSiX_{4-n}$, where n=1-3, X is, independently, fluorine, chlorine or bromine, and where R' is, independently, a hydrocarbyl group having from one to about twenty carbon atoms, or
   (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or
   (v) at least one hydrocarbyl aluminum halide of the formula $R''_mAlX_{3-m}$, where m=1 or 2, where X is, independently, fluorine, chlorine or bromine, and where R" is, independently, a hydrocarbyl group having from one to about twenty carbon atoms; or
   (vi) mixtures of any two or more of (i)-(v), and
(c) a source of water,
wherein the amount of halogen atoms is in the range of about 0.5 mole % to about 15 mole % relative to aluminum atoms, such that a haloaluminoxane composition is formed.

ip) A process according to io) wherein (b) is a halohydrocarbon which can be represented by the formula:

$$ArG_n$$

where Ar is an aromatic hydrocarbon ring system, G is $-CX_3$, $-CX_2R$, or $-CXR_2$, in which X is, independently, a fluorine atom, chlorine atom, or bromine atom, and in which R is, independently, a hydrogen atom or $C_{1-4}$ alkyl group; and n is 1 to 5.

iq) A process according to ip) wherein said haloaluminoxane is a partially halogenated aluminoxane.

ir) A process according to ip) wherein said aromatic compound is α,α,α-trifluorotoluene or α,α,α-trichlorotoluene.

is) A process according to ir) wherein said haloaluminoxane is a partially halogenated aluminoxane.

it) A process according to io) wherein said halogenation agent is a halohydrocarbon, and wherein at least one R is an aryl group.

iu) A process according to io) wherein said haloaluminoxane is a partially halogenated aluminoxane.

iv) A process according to io) wherein said halogenation agent is a siloxane; and wherein siloxane is a trisiloxane or a tricyclosiloxane.

iw) A process according to iv) wherein said siloxane is 3,3,3-trifluoropropylheptamethyltrisiloxane, 3,3,3-trifluoropropylheptamethyl-cyclotrisiloxane, or poly[methyl(3,3,3-trifluoropropyl)siloxane].

ix) A process according to iu) wherein (b) is a siloxane with at least one 3,3,3-trihalopropyl group.

iy) A process according to ix) wherein said 3,3,3-trihalopropyl group is a 3,3,3-trifluoropropyl group.

iz) A process according to ip)-iy) wherein said aluminum hydrocarbyl is trimethylaluminum, triethylaluminum, tri-n-butylaluminum, or triisobutylaluminum.

ja) A process according to ip) wherein said aluminum hydrocarbyl is trimethylaluminum; wherein G is $-CX_3$; and wherein said haloaluminoxane composition is a partially halogenated aluminoxane.

jb) A process according to ip) wherein said aluminum hydrocarbyl is trimethylaluminum; wherein G is —CX$_3$; and wherein said haloaluminoxane composition is a partially chlorinated aluminoxane.

jc) A process according to io) wherein said aluminoxane is methylaluminoxane; wherein (b) is α,α,α-trichlorotoluene or triphenylchloromethane; and wherein said haloaluminoxane composition is a partially chlorinated aluminoxane.

jd) A process according to io) wherein said halogenation agent is a silane, and wherein said silane is triphenylfluorosilane or trimethylfluorosilane.

jj) A process according to io) further comprising forming a supported haloaluminoxane by
A) contacting a support or carrier which is an inorganic oxide with (a) and (b), or
B) contacting said haloaluminoxane composition with a support or carrier which is an inorganic oxide,
such that a supported haloaluminoxane is formed.

jk) A process according to jj) wherein (b) is a halohydrocarbon which can be represented by the formula:

where Ar is an aromatic hydrocarbon ring system, G is —CX$_3$, —CX$_2$R, or —CXR$_2$, in which X is, independently, a fluorine atom, chlorine atom, or bromine atom, and in which R is, independently, a hydrogen atom or C$_{1-4}$ alkyl group; and n is 1 to 5.

jl) A process according to jk) wherein said haloaluminoxane is a partially halogenated aluminoxane.

jm) A process according to jk) wherein said aromatic compound is α,α,α-trifluortoluene or α,α,α-trichlorotoluene.

jn) A process according to jm) wherein said haloaluminoxane is a partially halogenated aluminoxane.

jo) A process according to jj) wherein said haloaluminoxane is a partially halogenated aluminoxane.

jp) A process according to jo) wherein (b) is a siloxane with at least one 3,3,3-trihalopropyl group.

jq) A process according to jp) wherein said 3,3,3-trihalopropyl group is a 3,3,3-trifluoropropyl group.

jr) A process according to jk)-jq) wherein said aluminum hydrocarbyl is trimethylaluminum, triethylaluminum, tri-n-butylaluminum, or triisobutylaluminum.

js) A process according to jk) wherein said aluminum hydrocarbyl is trimethylaluminum; wherein G is —CX$_3$; and wherein said haloaluminoxane composition is a partially halogenated aluminoxane.

jt) A process according to jv) wherein X is fluorine.

ju) A process as in any of jj)-jt) wherein said inorganic oxide is silica.

jv) A process according to jj) wherein said aluminum hydrocarbyl is trimethylaluminum; wherein G is —CX$_3$; wherein said inorganic oxide is silica; and wherein said haloaluminoxane composition is a partially halogenated aluminoxane.

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Except as may be expressly otherwise indicated, the article "a" or "an" if and as used herein is not intended to limit, and should not be construed as limiting, the description to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

The invention claimed is:

1. A process which comprises mixing, in an inert, anhydrous environment,
(a) at least one aluminoxane and
(b) at least one halogenation agent which is
    (i) at least one halohydrocarbon of the formula R$_n$CX$_{4-n}$, where n=1-3, X is, independently, fluorine, chlorine or bromine, and where R is, independently, a hydrogen atom or a hydrocarbyl group having from one to about twenty carbon atoms; or
    (ii) at least one siloxane having at least one labile halogen atom in the molecule, wherein each halogen atom is, independently, fluorine, chlorine, or bromine; or
    (iii) at least one silane of the formula R'$_n$SiX$_{4-n}$, where n=1-3, X is, independently, fluorine, chlorine or bromine, and where R' is, independently, a hydrocarbyl group having from one to about twenty carbon atoms; or
    (iv) at least one tin compound of the formula R'$_n$SnX$_{4-n}$, where n=1-3, X is, independently, fluorine, chlorine or bromine, and where R' is, independently, a hydrocarbyl group having from one to about twenty carbon atoms; or
    (v) at least one hydrocarbyl aluminum halide of the formula R"$_m$AlX$_{3-m}$, where m=1 or 2, where X is, independently, fluorine, chlorine or bromine, and where R" is, independently, a hydrocarbyl group having from one to about twenty carbon atoms; or
    (vi) mixtures of any two or more of (i)-(v);
wherein the amount of halogen atoms is in the range of about 0.5 mole % to about 15 mole % relative to aluminum atoms, such that a haloaluminoxane composition is formed.

2. A process according to claim 1 wherein (b) is at least one halohydrocarbon.

3. A process according to claim 1 wherein the amount of halogen atoms present in said haloaluminoxane composition is in the range of about 2 mole % to about 10 mole % relative to aluminum atoms.

4. A process according to claim 3 wherein (b) is at least one siloxane, silane, tin compound, or hydrocarbyl aluminum halide.

5. A process according to claim 1 wherein said inert, anhydrous environment is an anhydrous liquid hydrocarbon solvent.

6. A process according to claim 5 wherein said anhydrous liquid hydrocarbon solvent is an aromatic hydrocarbon.

7. A process according to claim 6 wherein said aromatic hydrocarbon is toluene.

8. A process according to claim 1 wherein the hydrocarbyl groups of said aluminoxane are saturated, and have from one to about twenty carbon atoms.

9. A process according to claim 1 wherein said aluminoxane is methylaluminoxane, ethylaluminoxane, n-butylaluminoxane, or isobutylaluminoxane.

10. A process according to claim 2 wherein said halohydrocarbon is one in which at least one R is an aryl group.

11. A process according to claim 2 wherein said aluminoxane is methylaluminoxane, ethylaluminoxane, n-butylaluminoxane, or isobutylaluminoxane, and wherein said halohydrocarbon is one in which at least one R is an aryl group.

12. A process according to claim 2 wherein said aluminoxane is methylaluminoxane, ethylaluminoxane, n-butylaluminoxane, or isobutylaluminoxane, and wherein said halohydrocarbon is α,α,α-trifluorotoluene.

13. A process according to claim 2 wherein said aluminoxane is methylaluminoxane; wherein said halohydrocarbon is α,α,α-trifluorotoluene; and wherein said inert, anhydrous environment is toluene.

14. A process according to claim 13 wherein the amount of halogen atoms present in said haloaluminoxane composition is in the range of about 2 mole % to about 10 mole % relative to aluminum atoms.

15. A process according to claim 13 wherein the amount of halogen atoms present in said haloaluminoxane composition is in the range of about 2 mole % to about 6 mole % relative to aluminum atoms.

16. A process according to claim 4 wherein said aluminoxane is methylaluminoxane, ethylaluminoxane, n-butylaluminoxane, or isobutylaluminoxane; wherein said halogenation agent is a siloxane; and wherein siloxane is a trisiloxane or a tricyclosiloxane.

17. A process according to claim 4 wherein said halogenation agent is a siloxane, and wherein said siloxane is 3,3,3-trifluoropropylheptamethyltrisiloxane, 3,3,3-trifluoropropylheptamethylcyclotrisiloxane, or poly[methyl(3,3,3-trifluoropropyl)siloxane].

18. A process according to claim 17 wherein said aluminoxane is methylaluminoxane, ethylaluminoxane, n-butylaluminoxane, or isobutylaluminoxane.

19. A process according to claim 4 wherein said aluminoxane is methylaluminoxane; wherein said halogenation agent is a siloxane, wherein said siloxane is poly[methyl(3,3,3-trifluoropropyl)siloxane]; and wherein said inert, anhydrous environment is toluene.

20. A process according to claim 4 wherein said halogenation agent is a silane.

21. A process according to claim 4 wherein said halogenation agent is a silane, and wherein said silane is triphenylfluorosilane or trimethylfluorosilane.

22. A process according to claim 1 further comprising forming a supported haloaluminoxane by
A) contacting said haloaluminoxane composition with a support material, or
B) contacting a support material with (a) and (b)
such that a supported haloaluminoxane is formed.

23. A composition formed from interaction between components comprising
(I) either a haloaluminoxane wherein the amount of halogen atoms is in the range of about 0.5 mole % to about 15 mole % relative to aluminum atoms, or
(a) at least one aluminoxane and
(b) at least one halogenation agent which is
(i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or
(ii) at least one siloxane having at least one labile halogen atom in the molecule, wherein each halogen atom is, independently, fluorine, chlorine, or bromine; or
(iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or
(iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or
(v) at least one hydrocarbyl aluminum halide of the formula $R''_mAlX_{3-m}$, where m=1 or 2, where X is, independently, fluorine, chlorine or bromine, and where R'' is, independently, a hydrocarbyl group having from one to about twenty carbon atoms; or
(vi) mixtures of any two or more of (i)-(v),
wherein the amount of halogen atoms is in the range of about 0.5 mole % to about 15 mole % relative to aluminum atoms; and
(II) at least one catalyst compound or complex of a transition metal of Groups 3 to 11 including the lanthanide series and the actinide series.

24. A process for forming a catalyst composition which comprises interacting, in an inert aromatic solvent, components comprising
(I) either a haloaluminoxane wherein the amount of halogen atoms is in the range of about 0.5 mole % to about 15 mole % relative to aluminum atoms, or
(a) at least one aluminoxane and
(b) at least one halogenation agent which is
(i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or
(ii) at least one siloxane having at least one labile halogen atom in the molecule, wherein each halogen atom is, independently, fluorine, chlorine, or bromine; or
(iii) at least one silane of the formula $R'_nSiX_{4-n}$, where n=1-3, X is, independently, fluorine, chlorine or bromine, and where R' is, independently, a hydrocarbyl group having from one to about twenty carbon atoms; or
(iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or
(v) at least one hydrocarbyl aluminum halide of the formula $R''_mAlX_{3-m}$, where m=1 or 2, where X is, independently, fluorine, chlorine or bromine, and where R" is, independently, a hydrocarbyl group having from one to about twenty carbon atoms; or (vi) mixtures of any two or more of (i)-(v), wherein the amount of halogen atoms is in the range of about 0.5 mole % to about 15 mole % relative to aluminum atoms; and (II) at least one catalyst compound or complex of a transition metal of Groups 3 to 11 including the lanthanide series and the actinide series.

25. A process according to claim 24 further comprising forming a supported catalyst composition by A) contacting a support material with (I) and (II), or B) contacting (I) with a support material, or C) contacting (II) with a support material, or D) contacting said catalyst composition with a support material, such that a supported catalyst composition is formed.

26. A process of producing a polyolefin polymer, which process comprises polymerizing at least one polymerizable olefinic monomer in the presence of a catalyst composition formed from interaction between components comprising (I) either a haloaluminoxane wherein the amount of halogen atoms is in the range of about 0.5 mole % to about 15 mole % relative to aluminum atoms, or (a) at least one aluminoxane and (b) at least one halogenation agent which is (i) at least one halohydrocarbon of the formula $R_nCX_{4-n}$, where n=1-3, X is, independently, fluorine, chlorine or bromine, and where R is, independently, a hydrogen atom or a hydrocarbyl group having from one to about twenty carbon atoms; or (ii) at least one siloxane having at least one labile halogen atom in the molecule, wherein each halogen atom is, independently, fluorine, chlorine, or bromine; or (iii) at least one silane of the formula $R'_nSiX_{4-n}$, where n=1-3, X is, independently, fluorine, chlorine or bromine, and where R' is, independently a hydrocarbyl group having from one to about twenty carbon atoms; or (iv) at least one tin compound of the formula $R'_nSnX_{4-n}$, where n=1-3, X is, independently, fluorine, chlorine or bromine, and where R' is, independently, a hydrocarbyl group having from one to about twenty carbon atoms; or (v) at least one hydrocarbyl aluminum halide of the formula $R''_mAlX_{3-m}$, where m=1 or 2, where X is, independently, fluorine, chlorine or bromine, and where R" is, independently, a hydrocarbyl group having from one to about twenty carbon atoms; or (vi) mixtures of any two or more of (i)-(v), wherein the amount of halogen atoms is in the range of about 0.5 mole % to about 15 mole % relative to aluminum atoms; and (II) at least one catalyst compound or complex of a transition metal of Groups 3 to 11 including the lanthanide series and the actinide series.

* * * * *